(12) United States Patent  
Kwak et al.

(10) Patent No.: US 7,879,850 B2  
(45) Date of Patent: Feb. 1, 2011

(54) ORGANIC COMPOUNDS

(75) Inventors: Young-Shin Kwak, Lexington, MA (US); Gary Mark Coppola, Budd Lake, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/239,029

(22) Filed: Sep. 26, 2008

(65) Prior Publication Data

US 2009/0186891 A1    Jul. 23, 2009

Related U.S. Application Data

(60) Provisional application No. 60/976,064, filed on Sep. 28, 2007.

(51) Int. Cl.
```
A61K 31/5377   (2006.01)
A61K 31/4184   (2006.01)
A61K 31/422    (2006.01)
A61K 31/427    (2006.01)
A61K 31/423    (2006.01)
A61K 31/428    (2006.01)
A61K 31/4245   (2006.01)
C07D 417/14    (2006.01)
C07D 413/14    (2006.01)
C07D 401/14    (2006.01)
```
(52) U.S. Cl. .............. 514/234.2; 514/236.8; 514/322; 514/367; 514/365; 514/364; 514/374; 514/375; 514/385; 514/394; 544/138; 546/199; 546/152; 548/131; 548/143; 548/181; 548/217; 548/235; 548/304.7

(58) Field of Classification Search .................. None  
See application file for complete search history.

(56) References Cited

U.S. PATENT DOCUMENTS

| | | | |
|---|---|---|---|
| 7,091,228 B2 | 8/2006 | Smith | |
| 7,132,456 B2 | 11/2006 | Gillig | |
| 7,402,696 B2 * | 7/2008 | Suzuki et al. | 564/86 |
| 2005/0070545 A1 | 3/2005 | Fox | |
| 2007/0123504 A1 | 5/2007 | Bolin | |
| 2009/0076275 A1 | 3/2009 | Bolin | |
| 2009/0093497 A1 | 4/2009 | Bolin | |
| 2009/0105273 A1 | 4/2009 | Bolin | |
| 2009/0170864 A1 | 7/2009 | Bolin | |

FOREIGN PATENT DOCUMENTS

| | | |
|---|---|---|
| EP | 882718 | 9/1998 |
| WO | 02072549 | 9/2002 |
| WO | 03015773 | 2/2003 |
| WO | 2004047755 | 6/2004 |
| WO | 2004069158 | 8/2004 |
| WO | 2004100881 | 11/2004 |
| WO | 2005007647 | 1/2005 |
| WO | 2005035526 | 4/2005 |
| WO | 2005080371 | 9/2005 |
| WO | WO2005108370 A1 * | 11/2005 |
| WO | 2005121132 | 12/2005 |
| WO | 2006004200 | 1/2006 |
| WO | 2006044775 | 4/2006 |
| WO | 2006/064189 | 6/2006 |
| WO | 2006060109 | 6/2006 |
| WO | 2006082952 | 8/2006 |
| WO | 2006113919 | 10/2006 |
| WO | 2006120125 | 11/2006 |
| WO | 2006134317 | 12/2006 |
| WO | 2007016538 | 2/2007 |
| WO | 2007022269 | 2/2007 |
| WO | 2007/056155 | 5/2007 |
| WO | 2007060140 | 5/2007 |
| WO | 2007071966 | 6/2007 |
| WO | 2007137103 | 11/2007 |
| WO | 2007137107 | 11/2007 |
| WO | 2007138304 | 12/2007 |
| WO | 2007138311 | 12/2007 |
| WO | 2007141502 | 12/2007 |
| WO | 2007141517 | 12/2007 |
| WO | 2007141538 | 12/2007 |
| WO | 2007141545 | 12/2007 |
| WO | 2007144571 | 12/2007 |
| WO | 2008011130 | 1/2008 |
| WO | 2008011131 | 1/2008 |
| WO | 2008059026 | 5/2008 |
| WO | 2008067257 | 6/2008 |
| WO | 2008099221 | 8/2008 |
| WO | 2008129319 | 10/2008 |
| WO | 2008134690 | 11/2008 |
| WO | 2008134693 | 11/2008 |

(Continued)

OTHER PUBLICATIONS

Serrano-Wu, et al, "Antisense and small-molecule modulation of diacylglycerol acyltransferase" Expert Opin. Ther. Patents (2007) 17(11), pp. 1331-1339.

(Continued)

*Primary Examiner*—Kamal A Saeed  
*Assistant Examiner*—Michael Barker  
(74) *Attorney, Agent, or Firm*—Theresa Devlin

(57) ABSTRACT

The present invention provides compounds of the following structure;

A-Q-B—C-D that are useful for treating conditions or disorders associated with DGAT1 activity in animals, particularly humans.

18 Claims, No Drawings

FOREIGN PATENT DOCUMENTS

| | | |
|---|---|---|
| WO | 2008141976 | 11/2008 |
| WO | 2008148840 | 12/2008 |
| WO | 2008148849 | 12/2008 |
| WO | 2008148851 | 12/2008 |
| WO | 2008148868 | 12/2008 |
| WO | 2009011285 | 1/2009 |
| WO | 2009016462 | 2/2009 |
| WO | 2009024821 | 2/2009 |
| WO | 2009071483 | 6/2009 |
| WO | 2009081195 | 7/2009 |
| WO | 2009119534 | 10/2009 |
| WO | 2009147170 | 12/2009 |

OTHER PUBLICATIONS

King, et al, "Inhibitors of diacylglycerol acyltransferase; a review of 2008 patents" Expert Opin. Ther. Patents (2010) 20(1), pp. 19-29.

U.S. Appl. No. 12/295,534, filed on Mar. 28, 2007, in the name of Novartis AG.

U.S. Appl. No. 12/446,088, filed on Oct. 17, 2007, in the name of Novartis AG.

U.S. Appl. No. 12/518,551, filed on Dec. 10, 2007, in the name of Novartis AG.

U.S. Appl. No. 12/502,669, filed on Jul. 14, 2009, in the name of Novartis AG.

Zhao, et al, "Validation of diacyl glycerolacyltransferase I as a novel target for the treatment of obesity and dyslipidemia using a potent and selective small molecule inhibitor," J Med Chem. Feb. 14, 2008;51(3):380-3. .

Birch, et al, "Discovery of a Potent, Selective, and Orally Efficacious Pyrimidinooxazinyl Bicyclooctaneacetic Acid Diacylglycerol Acyltransferase-1 Inhibitor," J. Med Chem. (2009), 52(6), 1558-1568.

Cheng, et al, "Acylation of Acylglycerols by Acyl Coenzyme A:Diacylglycerol Acyltransferase 1 ( DGAT1 ): functional importance of DGAT1 in the intestinal fat absorption," J. Biol. Chem. (2008), 283(44), 29802-29811.

Dow, et al, Discovery and Preclinical Pharmacology of PF-04620110: A Selective Inhibitor of DGAT-1 for the Treatment of Type-2 Diabetes, Gordon Conference on Medicinal Chemistry, Aug. 2009.

King, et al, "Diacylglycerol acyltransferase 1 inhibition lowers serum triglycerides in the Zucker fatty rat and the hyperlipidemic hamster," J. Pharm. Exp. Ther., (2009), 330(2), 526-531.

Linders, et al, "Discovery, synthesis and in vivo activity of phenylpiperazine DGAT-1 inhibitors for the treatment of metabolic syndrome," (Poster from 238th Amer. Chem Soc meeting), Aug. 2009.

Yun, et al, "Discovery and optimization of oxazole based DGAT1 inhibitors for the treatment of obesity," (Poster at American Diabetes Association, Jun. 2009).

Fox, et al, "Discovery of pyrrolophyridazines as novel DGAT1 inhibitors," (Abstracts of Papers, 237th ACS National Meeting, Salt Lake City, UT, United States, Mar. 22-26, 2009).

\* cited by examiner

ORGANIC COMPOUNDS

This application claims benefit under 35 U.S.C. §119(e) of U.S. Provisional Application No. 60/976,064, filed Sep. 28, 2007, the contents of which is incorporated herein by reference in its entirety.

Obesity can be viewed as an energy balance disorder, arising when energy input exceeds energy output, with most of the excess calories converted into triglycerides and stored in the adipose tissue. Medications currently approved for the treatment of obesity attempt to restore energy balance primarily by decreasing energy input by either suppressing appetite or interfering with lipid absorption in the small intestine. Because of the rapid increase in the prevalence of obesity worldwide and the lack of efficacy of current medical therapies, novel pharmacologic therapies for obesity are required.

One potential therapeutic strategy involves inhibiting triglyceride synthesis. Although triglycerides are essential for normal physiology, excess triglyceride accumulation results in obesity and, particularly when it occurs in nonadipose tissues, is associated with insulin resistance. DGAT is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1, see Cases et al, Proc. Natl. Acad. Sci. 95:13018-13023, 1998) and DGAT2 (acyl coA-diacylglycerol acyl transferase 2, see Cases et al, J. Biol. Chem. 276:38870-38876, 2001). DGAT1 and DGAT2 do not share significant protein sequence homology. Importantly, DGAT1 knockout mice are protected from high fat diet-induced weight gain and insulin resistance (Smith et al, Nature Genetics 25:87-90, 2000). The phenotype of the DGAT1 knockout mice suggest that a DGAT1 inhibitor has utility for the treatment of obesity and obesity-associated complications.

The present invention provides compounds that are useful for treating or preventing conditions or disorders associated with DGAT activity, especially DGAT1 activity in animals, particularly humans.

A compound having the following structure

A-Q-B—C-D and pharmaceutically acceptable salts, and prodrugs thereof,
wherein
A is a substituted or unsubstituted alkyl substituted or unsubstituted alkoxy, substituted or unsubstituted cycloalkyl, optionally substituted amino, substituted or unsubstituted aryl, substituted or unsubstituted heteroaryl or a substituted or unsubstituted heterocyclyl;
Q is a divalent or trivalent cycloalkyl, aryl, heterocycle or heteroaryl;
B is a substituted or unsubstituted divalent heteroaryl group selected from one of the groups below:

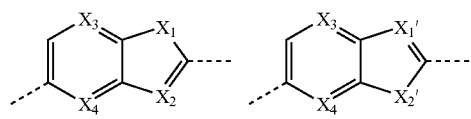

-continued

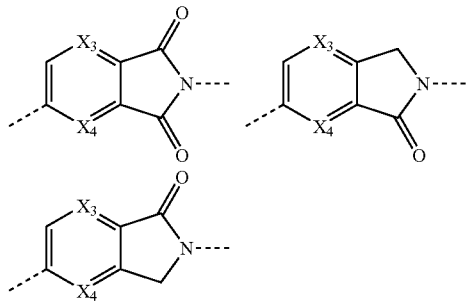

wherein
$X_1$ and $X_2'$ are independently selected from O, NH, $NR_9$ or S, wherein $R_9$ is selected from lower alkyl, lower alkylamino, lower alkoxyalkyl, lower hydroxyalkyl,
$X_1'$, $X_2$, $X_3$ and $X_4$ are independently selected from N, or CH,
C is

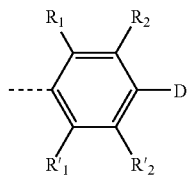

wherein
$R_1$ is selected from hydrogen, cyano, lower alkylsulfonylamino, alkanoylamino, halogen, lower alkyl, trifluoromethyl, lower alkoxy, lower alkylamino, lower dialkylamino, and $NO_2$,
$R'_1$, $R_2$ and $R'_2$ are independently selected from hydrogen, halogen, trifluoromethyl, aryloxy, lower alkyl, lower alkoxy, lower alkylamino, lower dialkylamino, and $NO_2$,
or
C may also be a substituted or unsubstituted bicyclic aryl or heteroaryl group,
D is selected from hydrogen, halogen, hydroxyl, cyano, alkanoylamino, carboxy, carbamoyl, —O-$L_2$-E, —S— $L_2$-E', —C(O)—O— $L_2$-E, -$L_2$-E" and —$NR_6$-$L_2$-E',
$L_2$ is —$(CH_2)_{n'}$—$(CR_5R_{5'})_{p'}$—$(CH_2)_{m'}$—
E is alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, —$SO_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido,
E' is alkyl, acyl, alkoxycarbonyl, cycloalkoxycarbonyl, aryloxycarbonyl, heterocyclyloxycarbonyl, carboxy, carbamoyl, sulfonylcarbamoyl, sulfonyl, —$SO_2$—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E" is alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, sulfamoyl, sulfonyloxy, sulfonamido, —SO$_2$—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, preferably 0, 1, 2, 3 or 4, R$_5$ and R$_{5'}$ are, independently from each other, hydrogen, halogen, hydroxyl, lower alkoxy, or lower alkyl or R$_5$ and R$_{5'}$ are joined together to form a spiro residue of the formula

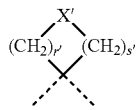

wherein
X' is NR$_x$, O, S or CR$_x$R$_{x''}$
r' and s' are, independently from each other, zero or an integer from 1 to 3,
R$_x$ is hydrogen or lower alkyl,
R$_{x'}$ is hydrogen, halogen, hydroxyl, alkoxy, or lower alkyl,
R$_{x''}$ is hydrogen or lower alkyl; or a stereoisomer, enantiomer or tautomer thereof, a pharmaceutically acceptable salt thereof, or a prodrug thereof.

Unless otherwise indicated, the compounds provided in the formula above are meant to include all pharmaceutically acceptable salts, prodrugs, stereoisomers, crystalline forms, or polymorphs thereof.

The present invention also provides pharmaceutical compositions comprising the compound as defined above and a pharmaceutically acceptable carrier or excipient.

The present invention also provides methods for treating or preventing conditions or disorders associated with DGAT activity preferably DGAT1 activity in animals, particularly humans. Preferably, the disorder is selected from the following: metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, and non-alcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris. In yet another aspect, the present invention provides methods of using a compound or composition of the invention as an anorectic.

The present invention also provides the use of a compound as described above.

The treatment of prevention of the DGAT or DGAT1-related disorders or conditions listed above consists of administering to subject in need thereof a therapeutically effective amount of a compound described in this invention. The treatment may also include co-administration with additional therapeutic agents.

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group.

In general, whenever an alkyl group is referred to as a part of the structure, an optionally substituted alkyl is also intended.

The term "substituted or unsubstituted alkyl" refers to straight- or branched-chain hydrocarbon groups having 1-20 carbon atoms, preferably 1-10 carbon atoms, containing 0 to 3 substituents. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, alkanoyl, alkoxy, alkoxycarbonyl, alkoxycarbonyloxy, alkanoyloxy, thiol, alkylthio, alkylthiono, alkylsulfonyl, sulfamoyl, sulfonamido, carbamoyl, cyano, carboxy, acyl, aryl, alkenyl, alkynyl, aralkyl, aralkanoyl, aralkylthio, arylsulfonyl, arylthio, aroyl, aroyloxy, aryloxycarbonyl, aralkoxy, guanidino, optionally substituted amino, heterocyclyl.

The term "lower alkyl" refers to those alkyl groups as described above having 1-7, preferably 2-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 4-6 carbon atoms connected by single bonds, e.g., —(CH$_2$)$_x$—, wherein x is 4-6, which may be interrupted with one or more heteroatoms selected from O, S, S(O), S(O)$_2$ or NR, wherein R may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

The term "carboxamide" refers to —C(O)—NHR$_□$, wherein R$_□$ is selected from hydrogen, a C$_1$-C$_8$ alkyl group, a substituted or unsubstituted cycloalkyl group, a substituted or unsubstituted aryl group, a substituted or unsubstituted heterocyclyl group, and carboxamide is preferably —C(O)—NH$_2$.

Exemplary monocyclic hydrocarbon groups include, but are not limited to, cyclopropyl, cyclobutyl, cyclopentyl, cyclopentenyl, cyclohexyl, and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "cycloalkanoyl" refers to cycloalkyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)—, heterocyclyl-NHC(O)—, cycloalkyl-NHC(O)—, and the like.
The term "sulfamoyl" refers to H$_2$NS(O)$_2$—, alkyl-NHS(O)$_2$—, (alkyl)$_2$NS(O)$_2$—, aryl-NHS(O)$_2$, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonylcarbamoyl" refers to sulfonyl-NHC(O)— or HO—SO$_2$—NHC(O)—.
The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.
The term "sulfonyl" refers to alkylsulfonyl, arylsulfonyl, heteroarylsulfonyl, aralkylsulfonyl, heteroaralkylsulfonyl cycloalkylsulfonyl and the like.
The term "sulfonate" or "sulfonyloxy" refers to alkyl-S(O)$_2$—O—, aryl-S(O)$_2$—O—, aralkyl-S(O)$_2$—O—, heteroaryl-S(O)$_2$—O—, heteroaralkyl-S(O)$_2$—O— and the like.
The term "optionally substituted amino" refers to a primary or secondary amino group which may optionally be substituted by a substituent such as alkyl, aryl, cycloalkyl, heterocyclyl, heteroaryl, acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.
The term "aryl" refers to monocyclic or bicyclic aromatic hydrocarbon groups having 6-14 or 6-12 carbon atoms in the ring portion, such as phenyl, biphenyl, naphthyl, anthryl, and tetrahydronaphthyl, each of which may optionally be substituted by 1-4 substituents, such as optionally substituted alkyl, trifluoromethyl, optionally substituted cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like.

The term "monocyclic aryl" refers to optionally substituted phenyl as described under aryl.

The term "aralkyl" refers to an aryl group bonded directly through an alkyl group, such as benzyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.
The term "cycloalkoxycarbonyl" refers to cycloalkyl-O—C(O)—.
The term "heterocyclyloxycarbonyl" refers to heterocyclyl-O—C(O)—.

The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2, 3 or 4 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridyl, pyridyl N-oxide, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents. Exemplary substituents include, but are not limited to, the following: optionally substituted alkyl, including trifluormethyl; hydroxyl (or protected hydroxyl); halo (halogen) e.g. Cl, F, Br; oxo, i.e., =O; optionally substituted amino; alkoxy;

cycloalkyl; carboxy; heterocyclooxy; alkoxycarbonyl, such as unsubstituted lower alkoxycarbonyl; mercapto; nitro; cyano; sulfamoyl; alkanoyloxy; aroyloxy; arylthio; aryloxy; alkylthio; formyl; carbamoyl; aralkyl; or aryl optionally substituted with alkyl, cycloalkyl, alkoxy, hydroxyl, amino, acylamino, alkylamino, dialkylamino or halo.

The term "heterocyclooxy" denotes a heterocyclic group bonded through an oxygen bridge.

The terms "saturated or unsaturated heterocycloalkyl" or "heterocycloalkyl" refers to nonaromatic heterocyclic or heterocyclyl groups as described above.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, tetrazol, isothiazolyl, furyl, thienyl, 2-pyridyl, 3-puridyl, 4-pyridyl, pyridyl N-oxide, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy, trifluormethyl, methoxy or halo.

The term "heteroarylsulfonyl" refers to heteroaryl-S$(O)_2$—.

The term "phosphonic acid" refers to —$P(O_2)$—OH

The term "phosphonate" refers to —$P(O_2)$—R, wherein R is selected from a $C_1$-$C_8$ alkyl group, a cycloalkyl group, a substituted or unsubstituted aryl group, preferably a substituted or unsubstituted phenyl, a substituted or unsubstituted heterocyclyl group, or a carboxylic acid ester group. Preferably the phenyl group R is unsubstituted or substituted by a halogen or a lower alkyl (e.g. 4-Me-phenyl-).

The term "heteroaroyl" refers to heteroaryl-C(O)—. The term "heteroaroylamino" refers to heteroaryl-C(O)NH—. The term "heteroaralkyl" refers to a heteroaryl group bonded through an alkyl group. The term "heteroaralkanoyl" refers to heteroaralkyl-C(O)—. The term "heterocyclyloyl" refers to heterocyclyl-C(O)—. The term "heteroaralkanoylamino" refers to heteroaralkyl-C(O)NH—.

The term "acyl" refers to alkanoyl, cycloalkanoyl, aroyl, heteroaroyl, aralkanoyl, heteroaralkanoyl, heterocyclyloyl and the like. The term "acylamino" refers to alkanoylamino, aroylamino, heteroaroylamino, aralkanoylamino, heteroaralkanoylamino and the like.

The term "divalent" refers to a residue linked to at least two residues and optionally having further substituents. As an example, within the context of the present invention the expression "substituted or unsubstituted divalent phenyl residue" is considered to be equivalent to the expression "substituted or unsubstituted phenylene residue".

For the carboxyl group derivatives —C(O)—O—R—PRO, the term "R—PRO" refers to the common ester derivatives that can serve as a prodrug. Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

The present invention provides a compound having the following structure

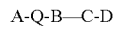

and pharmaceutically acceptable salts, and prodrugs thereof, wherein

A is a substituted or unsubstituted alkyl, substituted or unsubstituted alkoxy, substituted or unsubstituted cycloalkyl, optionally substituted amino, substituted or unsubstituted aryl, substituted or unsubstituted heteroaryl or a substituted or unsubstituted heterocyclyl;

Q is a divalent or trivalent cycloalkyl, aryl, heterocycle or heteroaryl;

B is a substituted or unsubstituted divalent heteroaryl group selected from one of the groups below:

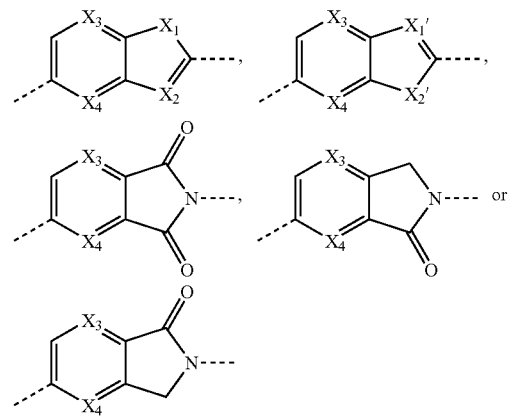

wherein;

$X_1$ and $X_2'$ are independently selected from O, NH, $NR_9$ or S, wherein $R_9$ is selected from lower alkyl, lower alkylamino, lower alkoxyalkyl, lower hydroxyalkyl, $X_1'$, $X_2$, $X_3$ and $X_4$ are independently selected from N, or CH, C is

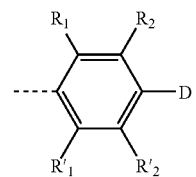

wherein $R_1$ is selected from hydrogen, cyano, lower alkylsulfonylamino, alkanoylamino, halogen, lower alkyl, trifluoromethyl, lower alkoxy, lower alkylamino, lower dialkylamino, and $NO_2$, $R'_1$, $R_2$ and $R'_2$ are independently selected from hydrogen, halogen, trifluoromethyl, aryloxy, lower alkyl, lower alkoxy, lower alkylamino, lower dialkylamino, and $NO_2$, or C may also be a substituted or unsubstituted bicyclic aryl or heteroaryl group, D is selected from hydrogen, halogen, hydroxyl, cyano, alkanoylamino, carboxy, carbamoyl, —O-L$_2$-E, —S— L$_2$-E', —C(O)—O— L$_2$-E, -L$_2$-E", and —NR$_6$-L$_2$-E', L$_2$ is —(CH$_2$)$_{n'}$—(CR$_5$R$_{5'}$)$_{p'}$, —(CH$_2$)$_{m'}$—

E is alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, —SO$_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido, E' is alkyl, acyl, alkoxycarbonyl, cycloalkoxycarbonyl, aryloxycarbonyl, heterocyclyloxycarbonyl, carboxy, carbamoyl, sulfonylcarbamoyl, sulfonyl, —SO$_2$—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E" is alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, sulfamoyl, sulfonyloxy, sulfonamido, —SO$_2$—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, preferably 0, 1, 2, 3 or 4, R$_5$ and R$_{5'}$ are, independently from each other, hydrogen, halogen, hydroxyl, lower alkoxy, or lower alkyl, or R$_5$ and R$_{5'}$ are joined together to form a spiro residue of the formula

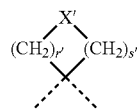

wherein

X' is NR$_x$, O, S or CR$_x$R$_{x''}$, r' and s' are, independently from each other, zero or an integer from 1 to 3, R$_x$ is hydrogen or lower alkyl, R$_{x'}$ is hydrogen, halogen, hydroxyl, alkoxy, or lower alkyl, R$_{x''}$ is hydrogen or lower alkyl; or a stereoisomer, enantiomer or tautomer thereof, a pharmaceutically acceptable salt thereof, or a prodrug thereof.

Another embodiment has the present invention represented by a compound having the following structure

A-Q-B—C-D wherein

A is a substituted or unsubstituted alkyl substituted or unsubstituted alkoxy, substituted or unsubstituted cycloalkyl, optionally substituted amino, substituted or unsubstituted aryl, substituted or unsubstituted heteroaryl or a substituted or unsubstituted heterocyclyl;

Q is a divalent or trivalent five membered heterocycle or heteroaryl;

B is a substituted or unsubstituted divalent heteroaryl group selected from one of the groups below:

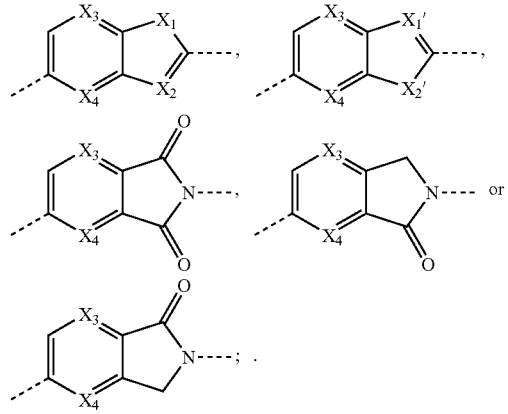

wherein

X$_1$ and X$_2$' are independently selected from O, NH, NR$_9$ or S, wherein R$_9$ is selected from lower alkyl lower alkylamino, lower alkoxyalkyl, lower hydroxyalkyl, X$_1$', X$_2$, X$_3$ and X$_4$ are independently selected from N, or CH, C is

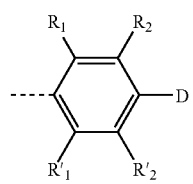

wherein

R$_1$ is selected from hydrogen, cyano, lower alkylsulfonylamino, alkanoylamino, halogen, lower alkyl, trifluoromethyl, lower alkoxy, lower alkylamino, lower dialkylamino, and NO$_2$, R'$_1$, R$_2$ and R'$_2$ are independently selected from hydrogen, halogen, trifluoromethyl, aryloxy, lower alkyl, lower alkoxy, lower alkylamino, lower dialkylamino, and NO$_2$, or C may also be a substituted or unsubstituted bicyclic aryl or heteroaryl group, D is selected from hydrogen, halogen, hydroxyl, cyano, alkanoylamino, carboxy, carbamoyl, —O-L$_2$-E, —S— L$_2$-E', —C(O)—O— L$_2$-E, -L$_2$-E" and —NR$_6$-L$_2$-E', L$_2$ is —(CH$_2$)$_{n'}$—(CR$_5$R$_{5'}$)$_{p'}$—(CH$_2$)$_{m'}$—

E is alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, —SO$_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido, E' is alkyl, acyl, alkoxycarbonyl, cycloalkoxycarbonyl, aryloxycarbonyl, heterocyclyloxycarbonyl, carboxy, carbamoyl, sulfonylcarbamoyl, sulfonyl, —SO$_2$—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E'' is alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, sulfamoyl, sulfonyloxy, sulfonamido, —SO$_2$—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

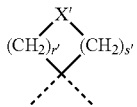

wherein

X' is $NR_x$, O, S or $CR_xR_{x''}$— r' and s' are, independently from each other, zero or an integer from 1 to 3, $R_x$ is hydrogen or lower alkyl, $R_{x'}$ is hydrogen, halogen, hydroxyl, alkoxy, or lower alkyl, $R_{x''}$ is hydrogen or lower alkyl; or a stereoisomer, enantiomer or tautomer thereof, a pharmaceutically acceptable salt thereof, or a prodrug thereof.

Unless otherwise indicated, the compounds provided in the formula above are meant to include all pharmaceutically acceptable salts, prodrugs, stereoisomers, crystalline forms, or polymorphs thereof.

In a preferred embodiment, the moiety A is selected from the group consisting of $C_{1-4}$alkyl, a substituted or unsubstituted $C_6$ monocyclic aryl group, a substituted or unsubstituted 6-membered monocyclic heteroaryl group, a substituted or unsubstituted 9 or 10-membered bicyclic aryl group, a substituted or unsubstituted biphenyl, a substituted or unsubstituted 5 or 6-membered monocyclic heterocyclyl, an optionally substituted amino or a 9 or 10-membered bicyclic heterocyclyl group.

When the moiety A is a substituted or unsubstituted alkyl group it is in a first preferred embodiment lower alkyl group.

When the moiety A is a substituted or unsubstituted alkoxy group it is in a first preferred embodiment lower alkoxy group.

When the moiety A is a substituted or unsubstituted cycloalkyl group it is in a first preferred embodiment a substituted or unsubstituted 5 or 6-membered monocyclic cycloalkyl group or substituted or unsubstituted adamantyl group.

In a preferred embodiment, the moiety A is selected from the group consisting of a substituted or unsubstituted aryl group preferably phenyl, or naphthyl, and a substituted or unsubstituted monocyclic or bicyclic heterocyclyl group.

Preferred substituents of the moiety A are halogen, alkyl, phenyl, cycloalkyl, cyano, trifluoromethyl, alkoxy, hydroxyl, optionally substituted amino, acyl, alkanoyloxy, aryloxy, alkylthio, arylthio, oxo, nitro, carboxy, alkoxycarbonyl, carbamoyl, alkylthiono, sulfonyl, sulfonamido, and heterocyclyl. More preferably, the substituents of moiety A are selected from halogen, unsubstituted or substituted lower alkyl, alkanoyl, —C(O)—NHalkyl, —C(O)—N(alkyl)$_2$, —C(O)—NHphenyl, cycloalkyl, cyano, oxo, trifluoromethyl, unsubstituted or substituted lower alkoxy, unsubstituted or substituted phenyl, unsubstituted or substituted phenoxy, aryloxy, hydroxyl, unsubstituted or substituted 5-membered monocyclic heteroaryl, 5 or 6-membered monocyclic heterocyclyloyl, carbamoyl, optionally substituted amino.

When the moiety A is a substituted or unsubstituted aryl group, it is in a first preferred embodiment a substituted or unsubstituted phenyl, a substituted or unsubstituted naphthyl or a substituted or unsubstituted biphenyl.

Other substituents of moiety A are independently from each other selected from, hydrogen, optionally substituted alkyl; hydroxyl (or protected hydroxyl); halo (halogen) e.g. Cl, F, Br; oxo, i.e. =O; optionally substituted amino; alkoxy; cycloalkyl; carboxy; heterocyclooxy; alkoxycarbonyl, such as unsubstituted lower alkoxycarbonyl; mercapto; nitro; cyano; sulfamoyl; alkanoyloxy; aroyloxy; arylthio; aryloxy; alkylthio; formyl; carbamoyl; aralkyl; or aryl optionally substituted with alkyl, cycloalkyl, alkoxy, hydroxyl, amino, acylamino, alkylamino, dialkylamino or halo, trifluoromethyl, acyl, alkanoyl, thiol, alkylthio, arylthio, carbamoyl, alkylthiono, sulfonyl, sulfonamido, heterocyclyl and the like.

When the moiety A is a monocyclic heterocyclyl, it is in a first preferred embodiment a substituted or unsubstituted 5 or 6-membered monocyclic heteroaryl.

When the moiety A is a monocyclic heteroaryl, it preferably is a substituted or unsubstituted imidazole, pyrazole, triazole, thiazole, pyridine, pyridine N-oxide, pyridazine, pyrimidine, triazine or pyrazine residue.

When the moiety A is a 6-membered monocyclic heteroaryl, it preferably is a substituted or unsubstituted pyridine, pyrimidine, pyridazine, pyridine N-oxide or pyrazine residue.

When the moiety A is a bicyclic heterocyclyl, it preferably is a substituted or unsubstituted 9 or 10-membered bicyclic heterocyclyl, preferably selected from substituted or unsubstituted benzimidazole, benzopyrrole, benzoxazole, benzothiazole, oxazolopyridine, thiazolopyridine, imidazolopyridine, indole, quinoline, isoquinoline, benzofuran, benzothiophene, indazole, cinnoline, quinazoline, coumarin, quinoxaline or phthalazine residue. More preferably, the bicyclic heterocyclyl group is selected from a substituted or unsubstituted benzimidazole, benzoxazole, quinoline, isoquinoline, benzothiazole, oxazolopyridine, thiazolopyridine or imidazolopyridine group.

In a further preferred embodiment, the moiety A is a substituted or unsubstituted phenyl.

In a preferred embodiment, the moiety A is a substituted or unsubstituted aryl group, or a substituted or unsubstituted monocyclic or bicyclic heterocyclyl group, selected from the group consisting of:

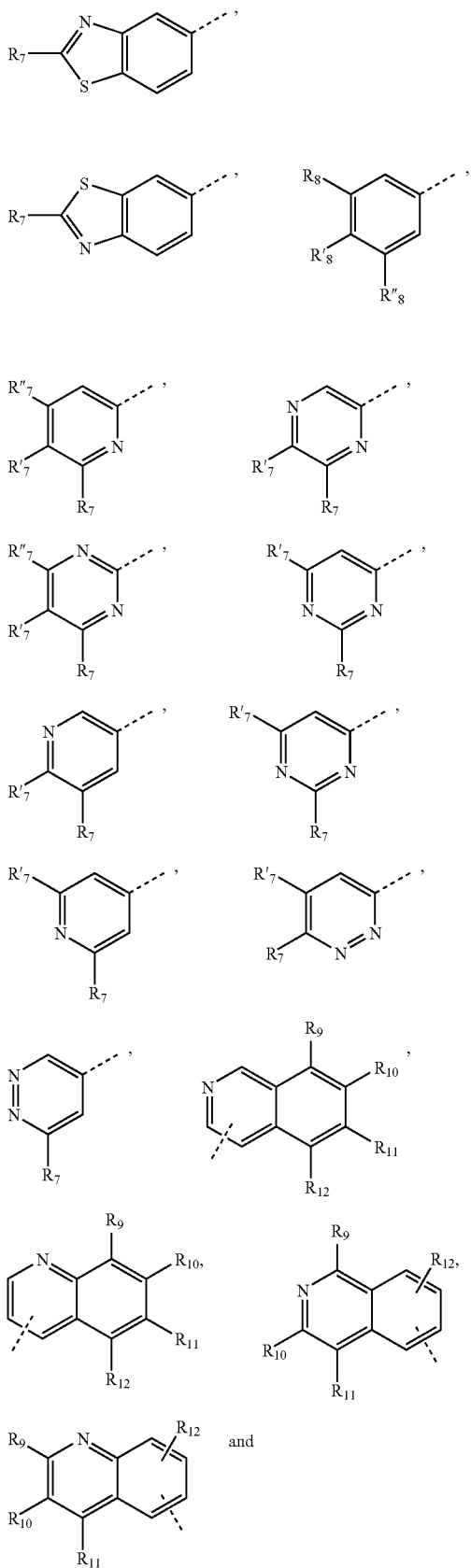

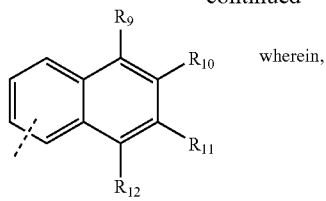

wherein,

R₇, R'₇ and R"₇ are independently selected from hydrogen optionally substituted alkyl; hydroxyl (or protected hydroxyl); halo (halogen) e.g. Cl, F, Br; oxo, i.e. =O; optionally substituted amino; alkoxy; cycloalkyl; carboxy; heterocyclooxy; alkoxycarbonyl, such as unsubstituted lower alkoxycarbonyl; mercapto; nitro; cyano; sulfamoyl; alkanoyloxy; aroyloxy; arylthio; optionally substituted aryloxy; alkylthio; formyl; carbamoyl; optionally substituted aralkyl; optionally substituted phenyl or optionally substituted aryl e.g. optionally substituted with alkyl, cycloalkyl, alkoxy, hydroxyl, amino, acylamino, alkylamino, dialkylamino or halo, preferably only one or two of the substituents R₇, R'₇ and R"₇ is not hydrogen, and R₈, R'₈ and R"₈ are independently selected from hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl, and preferably only one or two of the substituents R₈, R'₈ and R"₈ is not hydrogen, and R₉, R₁₀, R₁₁ and R₁₂ are independently selected from hydrogen, optionally substituted alkyl trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl.

In a preferred embodiment, the moiety A is a substituted or unsubstituted aryl group, or a substituted or unsubstituted monocyclic or bicyclic heterocyclyl group, selected from the group consisting of:

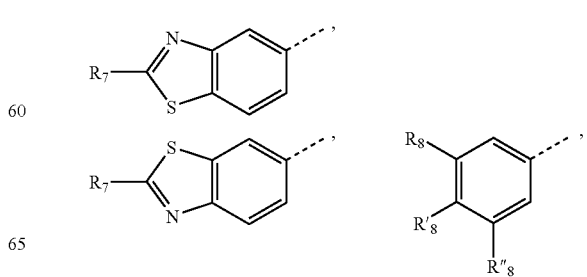

-continued bamoyl, and preferably only one or two of the substituents $R_8$, $R'_8$ and $R''_8$ is not hydrogen, and $R_9$, $R_{10}$, $R_{11}$ and $R_{12}$ are independently selected from hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl.

In another aspect of the invention Q is a divalent or trivalent five membered heterocycle or heteroaryl having one or more heteroatoms selected from N, S or O.

In another aspect of the invention moiety Q is a divalent or trivalent five membered heterocyclyl or heteroaryl selected from pyrrolyl, pyrazolyl, imidazolyl, triazolyl, oxazolyl, isoxazolyl, thiazolyl, tetrazol, isothiazolyl, furyl, or thienyl In another embodiments the moiety Q is selected from the group consisting of

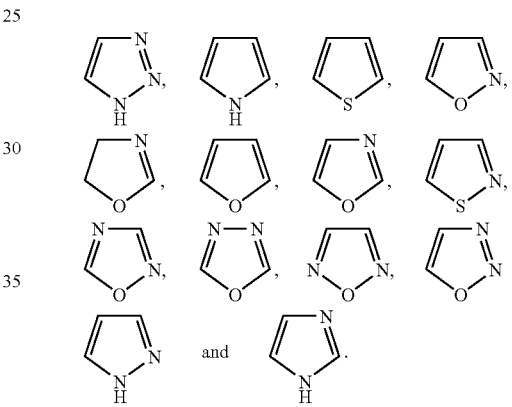

and

Another aspect is where Q is

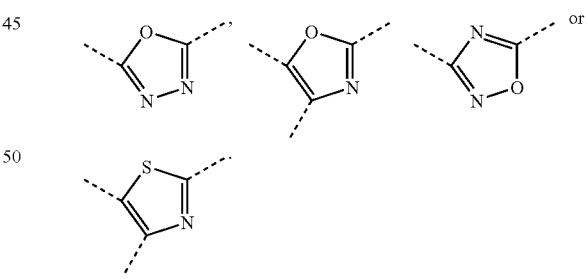

wherein, $R_7$, $R'_7$ and $R''_7$ are independently selected from hydrogen, halo, optionally substituted lower alkyl; trifluoromethyl, preferably only one or two of the substituents $R_7$, $R'_7$ and $R''_7$ is not hydrogen, and $R_8$, $R'_8$ and $R''_8$ are independently selected from hydrogen, optionally substituted alkyl trifluoromethyl, trifluoromethoxy, halo, hydroxy, optionally substituted alkoxy, acyl, alkanoyl, optionally substituted phenyloxy, optionally substituted aryloxy, optionally substituted phenyl, cyano, car- According to the present invention, the moiety B is a substituted or unsubstituted, bicyclic, 9-membered heteroaryl group. As explained above, the term "divalent" refers to a residue being attached to at least two further residues.

Besides the moieties A-Q- and —C-D to which it is attached, the moiety B can optionally have from 1 to 4, preferably 0, 1 or 2, additional substituents as described herein above for the heterocyclyl groups. Preferred substituents comprise halogen, alkyl cycloalkyl, cyano, trifluoromethyl, alkoxy, hydroxyl, and optionally substituted amino.

The moiety B can have the following orientation

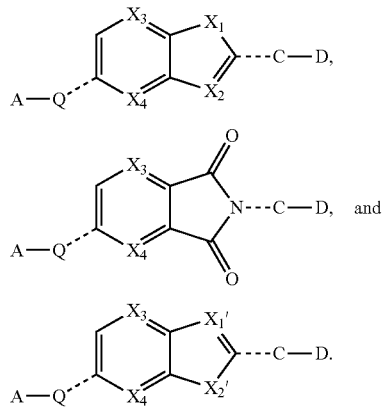

The moiety B may be selected from the group consisting of a substituted or unsubstituted, bicyclic, 9-membered heteroaryl group as herein described, wherein;

$X_1$, $X_2'$ are independently selected from O, NH, $NR_9$ or S, wherein $R_9$ is selected from lower alkyl lower alkylamino, lower alkoxyalkyl, lower hydroxyalkyl, $X_1'$, $X_2$, $X_3$, $X_4$ are independently selected from N or CH.

In another embodiment, the moiety B is a substituted or unsubstituted, bicyclic, 9-membered heteroaryl group as herein described, wherein the 5-membered ring is linked to the moiety C.

Preferably, the moiety B is selected from the group consisting of a substituted or unsubstituted, bicyclic, 9-membered heteroaryl group as herein described, wherein;

$X_1$, $X_2'$ are independently selected from O or NH, $X_1'$, $X_2$, are independently selected from N or CH, and $X_3$, $X_4$ are CH.

In a preferred embodiment, the moiety B is selected from;

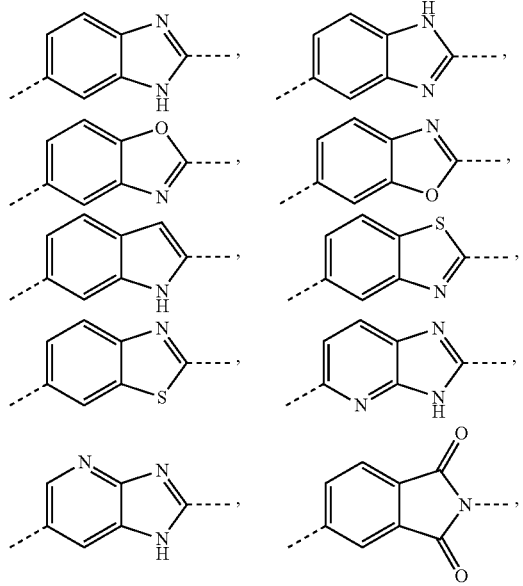

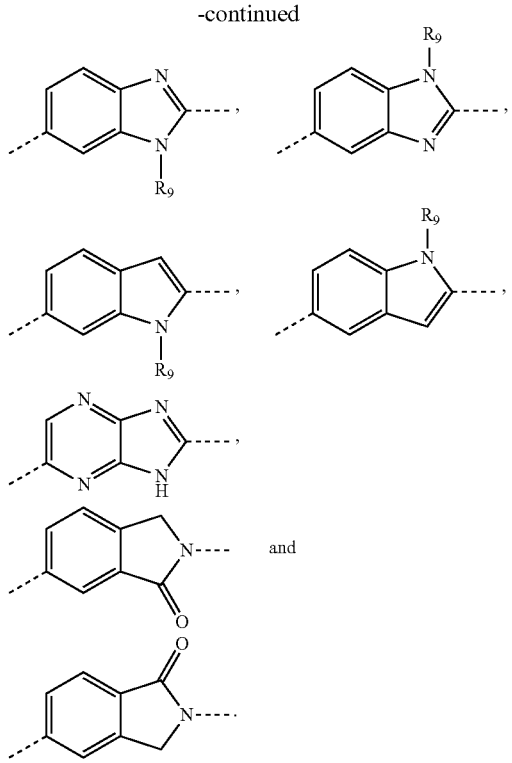

In a preferred embodiment, the moiety B is a substituted or unsubstituted, bicyclic, 9-membered heteroaryl group as herein described, wherein the 5-membered ring is linked to the moiety C i.e.

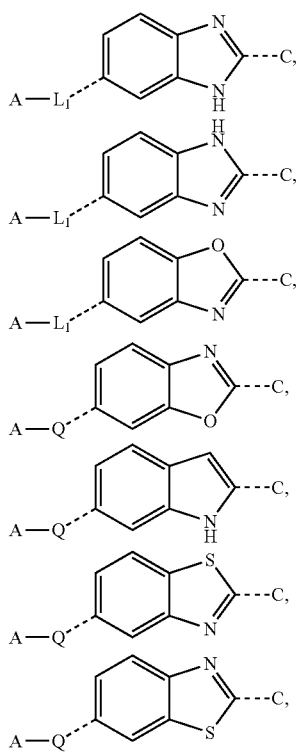

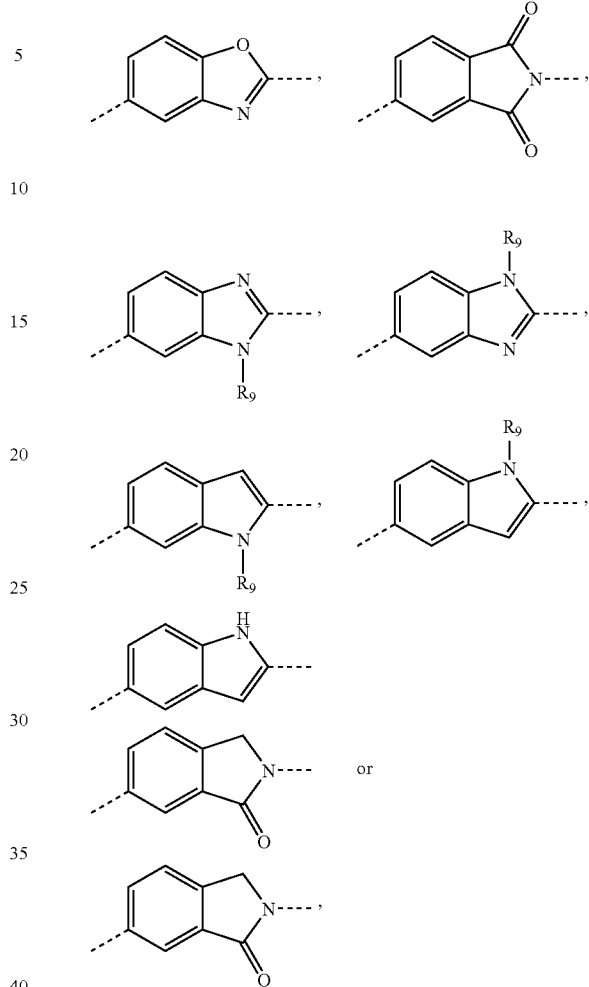

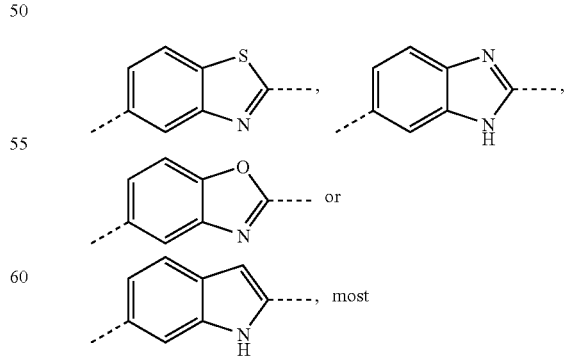

most preferably wherein the 5-membered ring is linked to the moiety C as described above.

In an other preferred embodiment, the moiety B is a substituted or unsubstituted, bicyclic heteroaryl group selected from;

preferably wherein the 5-membered ring is linked to the moiety C as described above.

In a preferred embodiment, the moiety B is a substituted or unsubstituted, bicyclic heteroaryl group selected from:

In the herein specification, the below two moieties B should be considered as equivalent

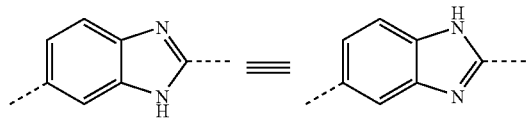

Preferably, the moiety B is selected from the group consisting of a substituted or unsubstituted, bicyclic heteroaryl group as herein described, wherein the optionally 1 to 4 substituents are selected from the substituents described herein above for the heterocyclyl groups, and preferably selected from halogen, substituted or unsubstituted lower alkyl lower alkoxy, cyano, nitro, optionally substituted amino. Substituted lower alkyl is for example substituted by hydroxyl.

In a preferred embodiment the moiety C is;

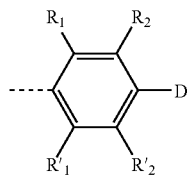

wherein
  $R_1$ is selected from hydrogen, cyano, lower alkylsulfonylamino, alkanoylamino, halogen, lower alkyl trifluoromethyl, lower alkoxy, lower alkylamino, lower dialkylamino, and $NO_2$,
  $R'_1$, $R_2$ and $R'_2$ are independently selected from hydrogen, halogen, trifluoromethyl, aryloxy, lower alkyl lower alkoxy, lower alkylamino, lower dialkylamino, and $NO_2$,
or
  $R'_1$ and $R'_2$ are joined together to form a substituted or unsubstituted 5 to 7-membered monocyclic aryl, substituted or unsubstituted 5 to 7-membered monocyclic heterocyclyl, or substituted or unsubstituted 5 to 7-membered monocyclic cycloalkyl group,
or
  $R_1$ and $R_2$ are joined together to form a substituted or unsubstituted 5 to 7-membered monocyclic aryl, substituted or unsubstituted 5 to 7-membered monocyclic heterocyclyl, or substituted or unsubstituted 5 to 7-membered monocyclic cycloalkyl group.

In a preferred embodiment the moiety C is;

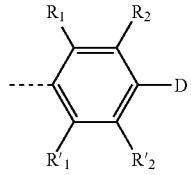

wherein
  $R_1$ is selected from hydrogen, cyano, lower alkylsulfonylamino, alkanoylamino, halogen, lower alkyl trifluoromethyl, lower alkoxy, lower alkylamino, lower dialkylamino, and $NO_2$,
  $R'_1$, $R_2$ and $R'_2$ are independently selected from hydrogen, halogen, trifluoromethyl, aryloxy, lower alkyl lower alkoxy, lower alkylamino, lower dialkylamino, and $NO_2$,
or
  $R'_1$ and $R'_2$ are joined together to form a substituted or unsubstituted 6-membered aryl.

In a preferred embodiment the moiety C is;

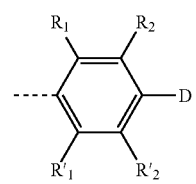

wherein
  $R_1$ is selected from halogen, cyano, lower alkylsulfonylamino, alkanoylamino, lower alkyl trifluoromethyl, lower alkoxy, lower alkylamino, lower dialkylamino, and $NO_2$,
  $R'_1$ is selected from hydrogen, halogen, lower alkyl trifluoromethyl, lower alkoxy, lower alkylamino, lower dialkylamino, and $NO_2$,
  $R_2$ and $R'_2$ are hydrogen.

In another preferred embodiment the moiety C is;

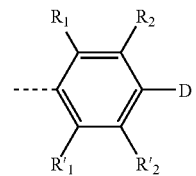

wherein
  $R_1$ is selected from halogen, trifluoromethyl, and lower alkyl,
  $R'_1$ is selected from hydrogen, nitro, halogen, trifluoromethyl and lower alkyl,
  $R_2$ and $R'_2$ are hydrogen.

In another preferred embodiment the moiety C is;

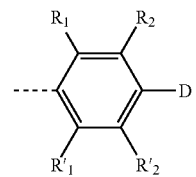

wherein
  $R_1$ is selected from halogen, trifluoromethyl and lower alkyl,
  $R'_1$ is selected from nitro, halogen, trifluoromethyl and lower alkyl,
  $R_2$ and $R'_2$ are hydrogen.

In a preferred embodiment the moiety D is selected from hydrogen, hydroxyl, cyano, alkanoylamino, carboxy, carbamoyl, $-O-L_2$-E, $-S-L_2$-E', $-C(O)-O-L_2$-E, $-L_2$-E", and $-NR_6-L_2$-E', wherein;

$L_2$ is —$(CH_2)_{n'}$—$(CR_5R_{5'})_{p'}$—$(CH_2)_{m'}$—,

E is alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, —$SO_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy, or sulfonamido, E' is alkyl, acyl, alkoxycarbonyl, cycloalkoxycarbonyl, aryloxycarbonyl, heterocyclyloxycarbonyl, carboxy, carbamoyl, substituted or unsubstituted aryl, sulfonylcarbamoyl, sulfonyl, sulfamoyl, sulfonamido, phosphonic acid, phosphonate, sulfonyloxy, —$SO_2$—OH, —C(O)—O—R—PRO, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E'' is alkyl, acyl, alkoxycarbonyl, phosphonic acid, phosphonate, cycloalkoxycarbonyl, aryloxycarbonyl, heterocyclyloxycarbonyl, carbamoyl, sulfonyl, sulfamoyl, sulfonyloxy, sulfonamido, —$SO_2$—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, preferably 0, 1, 2, 3 or 4, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

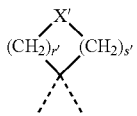

wherein;

X' is $NR_x$, O, S or $CR_{x'}R_{x''}$ r' and s' are, independently from each other, an integer from 0 to 3, $R_x$ is hydrogen or lower alkyl, $R_{x'}$ is hydrogen, halogen, hydroxyl, alkoxy, or lower alkyl, $R_{x''}$ is hydrogen or lower alkyl;

In a further preferred embodiment the moiety D is selected from hydrogen, halogen, hydroxyl, cyano, alkanoylamino, carboxy, —O-$L_2$-E, -$L_2$-E'', —C(O)—O—$L_2$-E and —$NR_6$-$L_2$-E', wherein, $L_2$ is —$(CH_2)_{n'}$—$(CR_5R_{5'})_{p'}$—$(CH_2)_{m'}$—

E is; alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, —$SO_2$—OH, —C(O)—O—R—PRO, substituted or unsubstituted aryl, substituted or unsubstituted heterocyclyl, or substituted or unsubstituted heteroaryl, E' is; alkyl, acyl, alkoxycarbonyl, cycloalkoxycarbonyl, aryloxycarbonyl, heterocyclyloxycarbonyl, carboxy, carbamoyl, sulfonyl, —$SO_2$—OH, —C(O)—O—R—PRO, substituted or unsubstituted aryl, substituted or unsubstituted heterocyclyl, or substituted or unsubstituted heteroaryl, E'' is; alkyl, acyl, alkoxycarbonyl, phosphonic acid, phosphonate, cycloalkoxycarbonyl, aryloxycarbonyl, heterocyclyloxycarbonyl, carboxy, sulfonyloxy, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, or is 0, 1, 2, 3 or 4, or preferably 0, 1 or 2, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

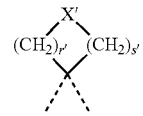

wherein;

X' is $NR_x$, O, S or $CR_{x'}R_{x''}$ r' and s' are, independently from each other, an integer from 0 to 3, $R_x$ is hydrogen or lower alkyl, $R_{x'}$ is hydrogen, halogen, hydroxyl, alkoxy, or lower alkyl, $R_{x''}$ is hydrogen or lower alkyl.

In a further preferred embodiment the moiety D is selected from hydrogen, halogen, hydroxyl, cyano, alkanoylamino, carboxy, —O-$L_2$-E, -$L_2$-E'', —C(O)—O—$L_2$-E and —$NR_6$-$L_2$-E', wherein, $L_2$ is —$(CH_2)_{n'}$—$(CR_5R_{5'})_{p'}$—$(CH_2)_{m'}$—

E is; alkyl, acyl, alkoxycarbonyl, phosphonic acid, phosphonate, cycloalkoxycarbonyl, aryloxycarbonyl, heterocyclyloxycarbonyl, carboxy, carbamoyl, sulfonyl, —$SO_2$—OH, —C(O)—O—R—PRO, substituted or unsubstituted aryl, substituted or unsubstituted heterocyclyl, or substituted or unsubstituted heteroaryl, E' is; alkyl, acyl, alkoxycarbonyl, cycloalkoxycarbonyl, aryloxycarbonyl, heterocyclyloxycarbonyl, carboxy, carbamoyl, sulfonyl, —$SO_2$—OH, —C(O)—O—R—PRO, substituted or unsubstituted aryl, substituted or unsubstituted heterocyclyl, or substituted or unsubstituted heteroaryl, E'' is alkyl, acyl, alkoxycarbonyl, phosphonic acid, phosphonate, cycloalkoxycarbonyl, aryloxycarbonyl, heterocyclyloxycarbonyl, carboxy, sulfonyloxy, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, or is 0, 1, 2, 3 or 4, or preferably 0, 1 or 2, $R_5$ and $R_{5'}$ are, independently from each other, hydrogen, halogen, hydroxyl, lower alkoxy, or lower alkyl, $R_6$ is hydrogen or lower alkyl.

In a second further preferred embodiment the moiety D is selected from hydrogen, halogen, hydroxyl, cyano, alkanoylamino, carboxy, carbamoyl, -$L_2$-(substituted or unsubstituted lower alkyl), -L$_2$-alkoxycarbonyl, -L$_2$-acyl, -L$_2$-(substituted or unsubstituted heteroaryl) or —O-L$_2$-E, wherein L$_2$ is —(CH$_2$)$_{n'}$—(CR$_5$R$_{5'}$)$_{p'}$—(CH$_2$)$_{m'}$—

E is a substituted or unsubstituted lower alkyl, acyl, a substituted or unsubstituted lower alkoxycarbonyl, phosphonic acid, phosphonate, cycloalkoxycarbonyl, aryloxycarbonyl, heterocyclyloxycarbonyl, carboxy, carbamoyl, sulfonyl, substituted or unsubstituted heterocyclyl, or substituted or unsubstituted heteroaryl, m', n' and p' are, independently from each other, an integer from 0 to 4, m'+n'+p' is between 0 and 12, or is 0, 1, 2, 3 or 4, or preferably 0, 1 or 2, R$_5$ and R$_{5'}$ are, independently from each other, hydrogen.

Preferably, the divalent residue -L$_2$- has the following orientation: —O—(CH$_2$)$_{n'}$—(CR$_5$R$_{5'}$)$_{p'}$—(CH$_2$)$_{m'}$→E, —S—(CH$_2$)$_{n'}$—(CR$_5$R$_{5'}$)$_{p'}$—(CH$_2$)$_{m'}$→E', —C(O)—O—(CH$_2$)$_{n'}$—(CR$_5$R$_{5'}$)$_{p'}$—(CH$_2$)$_{m'}$→E', —(CH$_2$)$_{n'}$—(CR$_5$R$_{5'}$)$_{p'}$—(CH$_2$)$_{m'}$→E", —NR$_6$—(CH$_2$)$_{n'}$—(CR$_5$R$_{5'}$)$_{p'}$—(CH$_2$)$_{m'}$→E".

In another aspect of the divalent residue -L$_2$- has the following orientation: —(CH$_2$)$_{n'}$—(CR$_5$R$_{5'}$)$_{p'}$—(CH$_2$)$_{m'}$→E", wherein n' is 1, p' is 1 and m' is 0; R$_5$R$_{5'}$ are independently hydrogen or C$_{1-4}$alkyl. For example, —CH$_2$—CH$_2$-E", —CH$_2$—C(H)(CH$_3$)-E" or —CH$_2$—C(CH$_3$)$_2$-E".

When E is a sulphonic acid group or a derivative thereof, it is preferably selected from a —S(O)$_2$—OH group, a —S(O)$_2$—NHR$^{10}$ group, or —S(O)$_2$—R$^{11}$ group, wherein R$^{10}$ is selected from hydrogen, a C$_1$-C$_8$ alkyl group, a cycloalkyl group, a substituted or unsubstituted aryl group, preferably a substituted or unsubstituted phenyl, a substituted or unsubstituted heterocyclyl group, or a carboxylic acid ester group. Most preferably E is selected from a —S(O)$_2$—OH group, or —S(O)$_2$—R$^{11}$ group. Preferably the phenyl group R$^{10}$ is unsubstituted or substituted by a halogen or a lower alkyl (e.g. 4-Me-phenyl-).

The sulphonic acid group or derivative thereof can be attached to the moiety L2 via its sulphur atom or via its nitrogen atom. Preferably, it is attached to the moiety L2 via its sulphur atom.

Chemical formulas of preferred embodiments are also shown below:

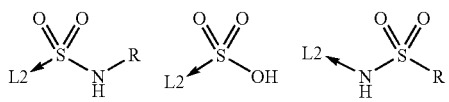

wherein R has the same meaning as R$^{10}$ defined above.

When E is an acyl, it is preferably a heterocyclyloyl or an alkanoyl which are unsubstituted or substituted as defined hereinabove. Preferred substituent is one or more substituents e.g. 1, 2, 3, 4 or 5 substituents, selected from an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

When E is a "heterocyclyloyl" i.e. heterocyclyl-C(O)—, preferably the carbonyl moiety "—C(O)—" is linked to, a substituted or unsubstituted, monocyclic 5 or 6-membered heterocyclyl group, or bicyclic 9 or 10-membered heterocyclyl group, via a ring member amino. The "heterocyclyloyl group" can be unsubstituted or substituted as defined herein for heterocyclyl rings. Preferred substituent is one or more substituents, e.g. 1, 2, 3, 4 or 5 substituents, selected from an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

In an embodiment the "heterocyclyloyl group" contains a fully saturated heterocyclyl. Examples of preferred heterocyclyl groups, which can be substituted or unsubstituted are;

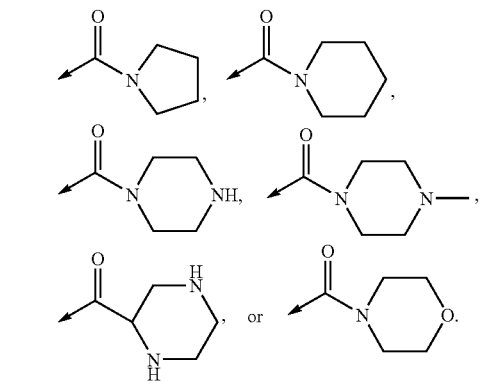

When E is an alkanoyl, the alkyl moiety is preferably a substituted or unsubstituted lower alkyl. The preferred substitutents e.g. 1, 2, 3, 4 or 5 substituents, are selected from —CF$_3$, halogen, hydroxyl, cycloalkyl, aryl, heterocyclyl, nitro, optionally substituted amino, cyano, carboxy, and/or a thiol group.

When E is carbamoyl, the alkyl moiety is preferably a substituted or unsubstituted lower alkyl, the aryl moiety is preferably substituted or unsubstituted phenyl, the heterocyclyl moiety is preferably a substituted or unsubstituted 6 or 5-membered heterocyclyl, or a substituted or unsubstituted 9 or 10-membered heterocyclyl.

A preferred carbamoyl is —C(O)—NRaRb, wherein Ra and Rb are independently selected from hydrogen and a substituted or unsubstituted lower alkyl.

When E is an alkoxycarbonyl, the alkyl moiety is preferably a substituted or unsubstituted lower alkyl. The preferred substitutents e.g. 1, 2, 3, 4 or 5 substituents, are —CF$_3$, halogen, hydroxyl, cycloalkyl, aryl, heterocyclyl, nitro, optionally substituted amino, cyano, carboxy, and/or a thiol group.

When E contains an aryl group e.g. "E" is aryl, or aryloxycarbonyl, the aryl is substituted or unsubstituted and is preferably phenyl. Preferred substituent is one or more substituents, e.g. 1, 2, 3, 4 or 5 substituents, selected from a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

When E contains a heterocyclyl group e.g. "E" is a heterocyclyl, heterocyclyl-NHC(O)—, or heterocyclyloxycarbonyl, the heterocyclyl moiety is optionally substituted. Preferred substituent is one or more substituents, e.g. 1, 2, 3, 4 or 5 substituents, selected from, an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/ or a thiol group.

When E is a substituted or unsubstituted heterocyclyl, it is preferably a 5-membered heterocyclyl residue, and preferably selected from the group consisting of: a tetrazole residue, a triazole residue, an oxadiazole residue, a thiadiazole residue, a diazole residue, an oxazole residue, a thiazole residue, an oxathiadiazole residue, a tetrahydropyrrole (pyrrolidin).

Preferred substituent is one or more substituents, e.g. 1, 2, 3, 4 or 5 substituents, selected from, an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

When E is a 5-membered heterocyclyl residue, representing moiety E are also shown below:

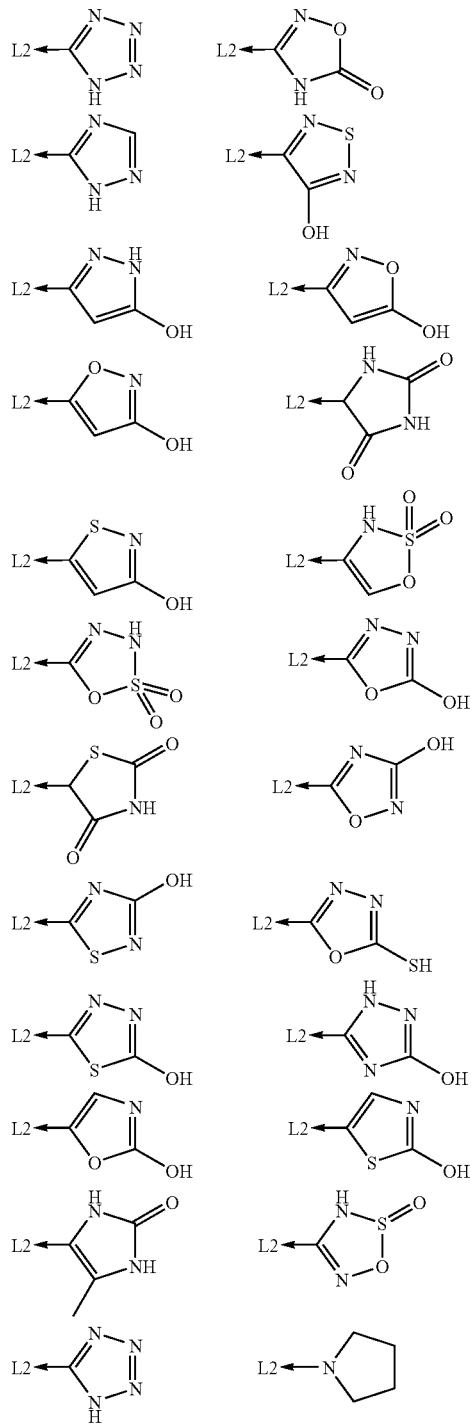

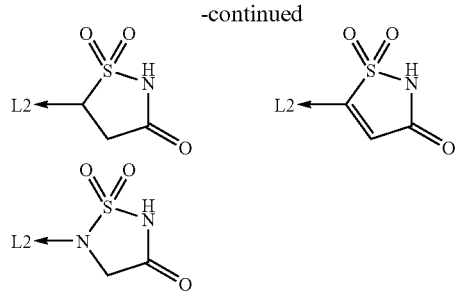

In a further embodiment, the moiety E is selected from phosphonic acid, —P(O$_2$)— (substituted or unsubstituted lower alkyl), —P(O$_2$)-(substituted or unsubstituted phenyl), carboxy, —S(O)$_2$—OH, —S(O)$_2$-(substituted or unsubstituted lower alkyl), —S(O)$_2$-(substituted or unsubstituted phenyl), —S(O)$_2$-trifluoromethyl, a substituted or unsubstituted lower alkyl, a substituted or unsubstituted heterocyclyl, a substituted or unsubstituted alkanoyl, a substituted or unsubstituted alkoxycarbonyl, a substituted or unsubstituted phenyloxycarbonyl, —C(O)—NH-(substituted or unsubstituted lower alkyl), —C(O)—N(substituted or unsubstituted lower alkyl)$_2$, —C(O)—NH$_2$, a substituted or unsubstituted 5-membered monocyclic heterocyclyl.

In a further embodiment, the moiety D is hydrogen, lower alkanoylamino, or carboxy.

The present invention includes all pharmaceutically acceptable isotopically-labeled compounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of Formula (I) can generally be prepared by conventional techniques known to those skilled in the art or by processes analogous to those described in the accompanying Examples and Preparations Sections using an appropriate isotopically-labeled reagent in place of the non-labeled reagent previously employed.

The present invention also provides a pharmaceutical composition comprising the compound as defined above and a pharmaceutically acceptable carrier or excipient.

The present invention also provides for a method of treating DGAT1 associated disorder by administering a therapeutically effective amount of the compounds described above.

In a preferred embodiment, the compound used for the manufacture of the medicament is one of those as defined herein, especially the herein specifically described compounds.

Among the preferred DGAT especially DGAT1 associated disorders, the following can be mentioned:

Metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris.

Preferably, the DGAT1 associated disorder is impaired glucose tolerance, Type 2 diabetes and obesity.

In yet another aspect, the present invention provides methods of using the compound or composition of the invention as an anorectic.

The compounds of the invention depending on the nature of the substituents possess one or more stereogenic centers. The resulting diastereoisomers, optical isomers, i.e., enantiomers, and geometric isomers, and mixtures thereof, are encompassed by the instant invention.

The processes described herein for the preparation of compounds above may be conducted under inert atmosphere, preferably under nitrogen atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization.

Finally, compounds of the invention are either obtained in the free form, or in a salt form thereof, preferably, in a pharmaceutically acceptable salt form thereof, or as a prodrug derivative thereof.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention, in general, may be converted into acid addition salts, especially pharmaceutically acceptable salts. These are formed, e.g., with inorganic acids, such as mineral acids, e.g., sulfuric acid, phosphoric or hydrohalic acid, or with organic carboxylic acids, such as ($C_1$-$C_4$)-alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as ($C_1$-$C_4$)-alkylsulfonic acids, e.g., methanesulfonic acid; or arylsulfonic acids which are unsubstituted or substituted (for example by halogen).

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the □-(amino, mono- or di-lower alkylamino, carboxy, lower alkoxycarbonyl)-lower alkyl esters, the □-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention may be employed for the treatment of conditions mediated by DGAT especially DGAT1 activity. Such compounds may thus be employed therapeutically for the treatment of impaired glucose tolerance, Type 2 diabetes and obesity.

In yet another aspect, the present invention provides methods of using a compound or composition of the invention to treat or prevent a disease or condition associated with DGAT especially DGAT1. Disease and conditions associated with lipid metabolism and cell proliferation, and complications thereof, may be treated with the subject compounds and compositions. In one group of embodiments, diseases and conditions, including chronic diseases, of humans and other species that can be treated with inhibitors of DGAT especially DGAT1 function include, but are not limited to, metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris.

In yet another aspect, the present invention provides methods of using a compound or composition of the invention as an anorectic.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by DGAT especially DGAT1 activity. Such conditions include impaired glucose tolerance, Type 2 diabetes and obesity.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by DGAT especially DGAT1 activity, preferably, impaired glucose tolerance, Type 2 diabetes and obesity.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) anti-obesity agents such as orlistat or rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; □-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

In each case in particular in the compound claims and the final products of the working examples, the subject matter of the final products, the pharmaceutical preparations and the claims are hereby incorporated into the present application by reference to these publications and patent applications.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by DGAT activity preferably DGAT1 activity, preferably, impaired glucose tolerance, Type 2 diabetes and obesity.

Thus, the present invention also relates to a compound as defined in the claims and described above for use as a medicament; to the use of a compound as defined in the claims and described above for the preparation of a pharmaceutical composition for the prevention and/or treatment of conditions mediated by DGAT activity preferably DGAT1 activity, and to a pharmaceutical composition for use in conditions mediated by DGAT activity preferably DGAT1 activity comprising a compound as defined in the claims and described above, or a pharmaceutically acceptable salt thereof, in association with a pharmaceutically acceptable diluent or carrier therefore.

The present invention further provides a method for the prevention and/or treatment of conditions mediated by DGAT activity preferably DGAT1 activity, which comprises administering a therapeutically effective amount of a compound of the present invention.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound as defined in the claims and described above, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents and anti-hypertensive agents, or a pharmaceutically acceptable salt thereof. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent and an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound as defined in the claims and described above, or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of the DGAT especially DGAT1 activity.

Preferably, the condition associated with DGAT especially DGAT1 activity is selected from impaired glucose tolerance, Type 2 diabetes and obesity.

Finally, the present invention provides a method or use which comprises administering a compound as defined in the claims and described above in combination with a therapeutically effective amount of an anti-diabetic agent, a hypolipidemic agent, an anti-obesity agent or an anti-hypertensive agent.

Ultimately, the present invention provides a method or use which comprises administering a compound as defined in the claims and described above in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.1 mg/kg and 1000 mg/kg, preferably between about 1 mg/kg and 100 mg/kg.

The activity of compounds according to the invention may be assessed by the following methods or methods well-described in the art:

The enzyme preparation used in this assay is a membrane preparation from Sf9 cells overexpressing human $(His)_6$ DGAT1. During all steps samples were chilled to 4° C. Sf9 cells expressing human $(His)_6$DGAT1 were thawed at RT and re-suspended at a 10:1 ratio (mL buffer/g of cells) in 50 mM HEPES, 1× Complete Protease Inhibitor, pH 7.5. The re-suspended pellet was homogenized for 1 min using a Brinkman PT 10/35 homogenizer with a 20 mm generator. Cells were lysed using Avestin Emulsiflex (chilled to 4° C.) at 10000-15000 psi. Lysate was centrifuged at 100,000×g for 1 h at 4° C. Supernatant was removed and pellets were re-suspended in 50 mM HEPES, 1× Complete Protease Inhibitor, pH 7.5 at ⅙ the volume of supernatant. Re-suspended pellets were pooled and homogenized with 10 strokes of a Glas-Col motor driven teflon pestle on setting 70. The protein concentration of the membrane preparation was quantified using BCA protein assay with 1% SDS. The membrane preparation was aliquoted, frozen on dry ice, and stored at −80° C.

For 50 mL, 25 mL of 0.2 M HEPES stock buffer, 0.5 mL of 1 M $MgCl_2$ (5 mM final concentration), and 24.5 mL of milli-Q $H_2O$ are added to the 55 mL Wheaton Potter-Elvehjem homogenizer. Enzyme preparation (0.1 mL) is added to buffer and the mixture is homogenized with 5 strokes on ice using the Glas-Col variable speed homogenizer system on setting 70.

For 50 mL, 0.5 mL 10 mM diolein is added to 9.5 mL of EtOH in a 50 mL Falcon screw cap conical centrifuge tube. Five mL of 10 mM sodium acetate pH 4.5 is added followed by 0.5 mL of 10 mM oleoyl-CoA. Finally, the remaining 4.5 mL of 10 mM sodium acetate pH 4.5 is added followed by 30 mL of milli-Q $H_2O$. The solution should be gently agitated by hand to induce mixing. The final concentrations of EtOH and sodium acetate are 20% and 2 mM, respectively.

Dry compounds are dissolved in the appropriate volume of DMSO to a final concentration of 10 mM. A 10-point, 3-fold dose response is used to evaluate compound potency. All dilutions are performed in DMSO in a Greiner 384-well microplate.

1. 2 μL of compound in DMSO is added to the appropriate wells. 2 μL of DMSO is added to 100% activity and 100% inhibition controls.

2. 25 μL of enzyme mix is added to all wells and plate(s) are incubated for 10 min at RT.

3. 10 μL of 20% acetic acid quench is added to 100% inhibition control wells. Plate(s) are vortexed using Troemner multi-tube vortexer (setting 7 for 10 sec).

4. 25 μL of substrate mix is added to all wells. Plate(s) are vortexed using Troemner multi-tube vortexer (setting 7 for 10 sec). Plate(s) are incubated for 30 min at RT.

5. 10 μL of 20% acetic acid quench is added to all wells. Plate(s) are vortexed using Troemner multi-tube vortexer (setting 7 for 10 sec).

6. 50 μL of 1-butanol w/glyceryl tripalmitoleate internal standard is added to all wells.

7. Plate(s) are sealed with super pierce strong plate sealer using the thermo-sealer.

8. Plate(s) are vortexed using Troemner multi-tube vortexer (setting 10 for 5 min).

9. Plate(s) are centrifuged at 162×g (1000 rpm for GH-3.8 rotor) for 5 min using Beckman GS-6R tabletop centrifuge.

Samples were analyzed by LC/MS/MS using a Waters 1525μ LC and Quattro Micro API MS. Where indicated, tripalmitolein was used as an internal standard to control for instrument variation.

Data is converted to % inhibition prior to curve fitting using the following equation:

$$\% \text{ Inhibition} = \frac{\left(\frac{\text{response compound} -}{\text{response 100\% inhibition control}}\right)}{\left(\frac{\text{response 100\% activity control} -}{\text{response 100\% inhibition control}}\right)} \times 100$$

Using the method described above, the compounds of the present invention were shown to possess inhibitory activity with IC50 values ranging from 0.001 uM to 100 uM.

Table 1 shows the inhibitory activity ($IC_{50}$ values) of representative compounds to human DGAT1.

| Example | $IC_{50}$ (μM) |
| --- | --- |
| 1-38, 1-43, 1-59, 1-62 | 0.054, 0.080, 0.009, 0.015 |
| 1-29, 1-51, | 0.4, 0.31 |
| 1-15, 1-25 | 2.3, 4.7 |
| 1-24, 1-34 | greater than 10 |

The activity on DGAT2 receptors can be assessed as described in the International patent application WO03/053363.

Methods of Preparation:

In the below description of general Methods of Preparation and Synthesis;

Ar can represent D-C— wherein D and C are as hereinabove defined.

ArCHO can represent D-C—CHO, wherein D and C are as hereinabove defined.

$RNH_2$ can represent $H_2N$—$(CH_2)_n$—$(CR_4R_{4'})_p$—$(CH_2)_m$-A or A-$(CH_2)_n$—$(CR_4R_{4'})_p$—$(CH_2)_m$—$NH_2$ wherein A, $R_4$, $R_{4'}$, p, n and m have the same definition as for $L_1$ which are hereinabove defined.

RCOCl can represent Cl—C(O)—$(CH_2)_n$—$(CR_4R_{4'})_p$—$(CH_2)_m$-A or A-$(CH_2)_n$—$(CR_4R_{4'})_p$—$(CH_2)_m$—C(O)—Cl wherein A, $R_4$, $R_{4'}$, p, n and m have the same definition as for L1 which are hereinabove defined.

Y can represent A-L1-.

R, R' can represent A wherein A is as hereinabove defined.

Scheme 1.

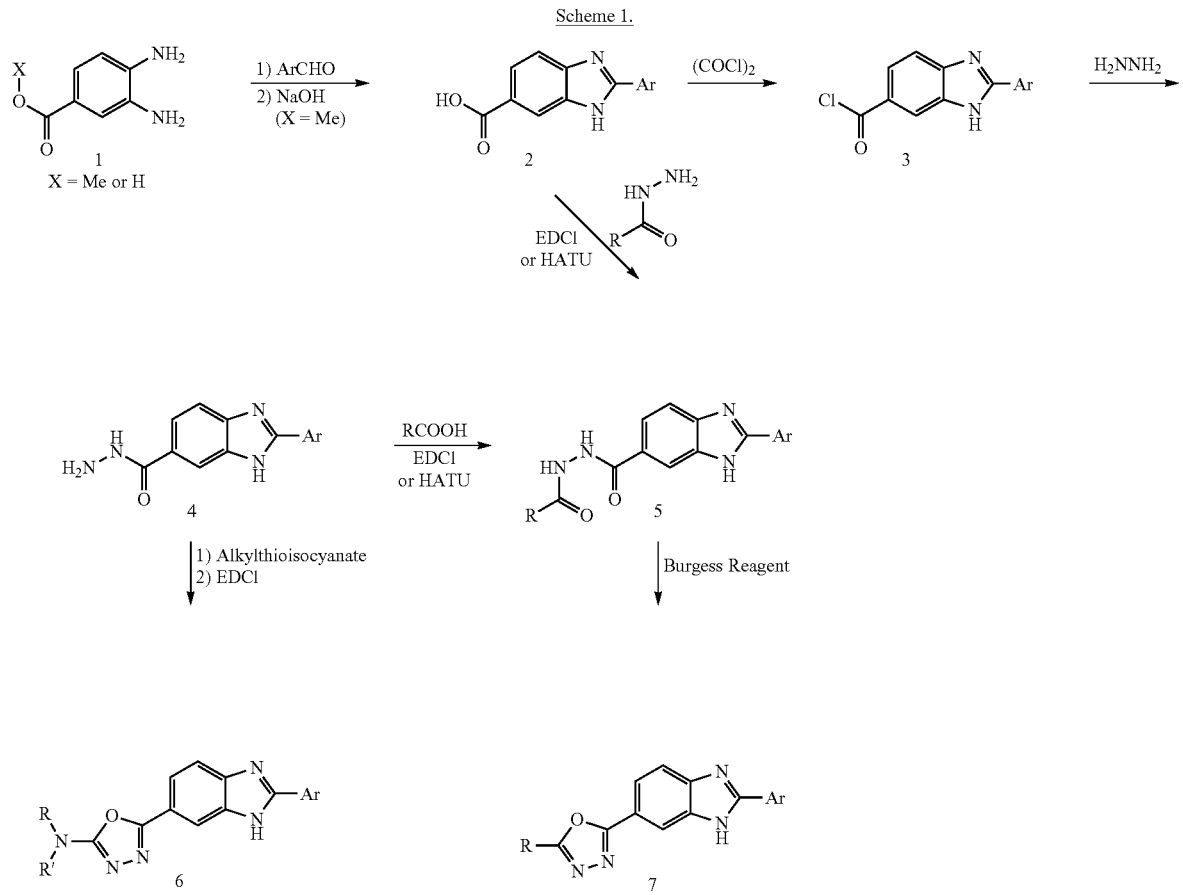

Oxidative cyclocondensation of 3,4-diamino-benzoic acid or its methyl ester with substituted benzaldehyde provides the benzimidazole core. The reaction is carried out in the open air in oxidizing media, such as DMSO or nitrobenzene, preferably the former, in the presence of a catalyst such as Oxone, FeCl3, Sc(OTf)3/Cu(OTf)2, or Yb(OTf)3/Cu(OTf)2. After saponification of the ester, resulting carboxylic acid is converted to acid chloride by the action of oxalyl chloride and ensuing amidation with hydrazine in the presence of base such as, but not limited to, TEA, DIPEA, pyridine, or Na2CO3, affords compounds 4. Compounds 4 are converted to compounds 5 by amidation reactions with a variety of alkyl or aromatic carboxylic acids by coupling reagents such as, but not limited to, EDCI or HATU. Compounds 5 are alternatively obtained from compounds 3 by amidation reactions with a variety of acyl hydrazides in analogous fashion. Compounds 5 are converted to form compounds 7 by cyclocondensation. In addition, compounds 4 are transformed to thioureas and ensuing cyclization using EDCI affords compounds 6.

Scheme 2.

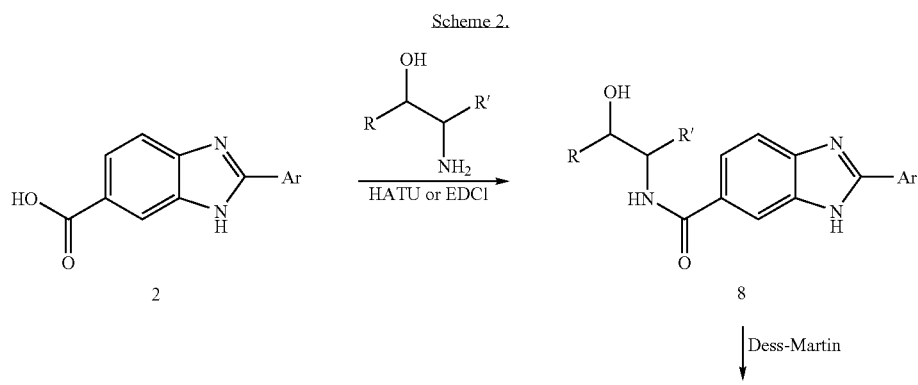

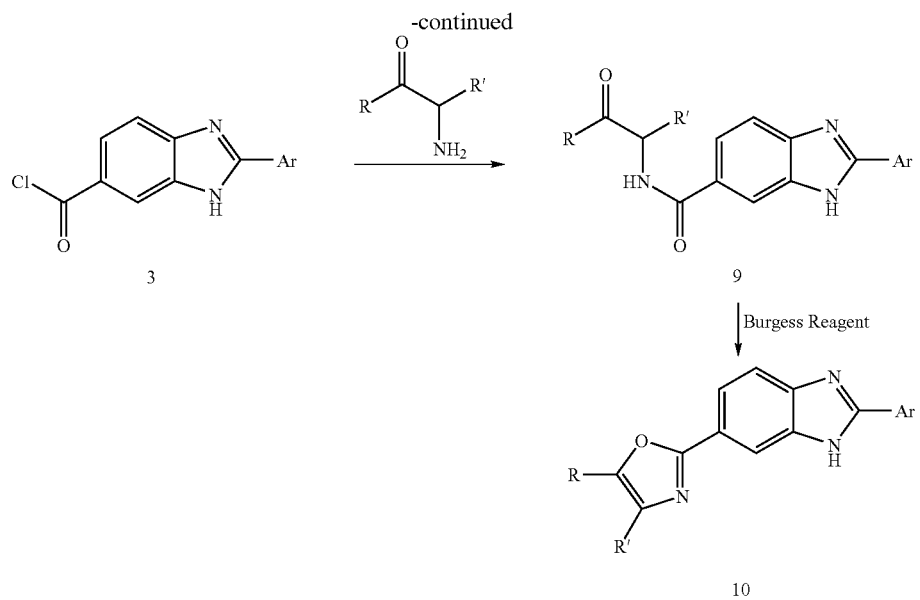

In the similar fashion, compounds 2 is converted to compounds 8 by amidation reactions with a variety of 1,2-aminoalcohols in the presence of coupling reagents such as, but not limited to, HATU or EDCI. Oxidation of the hydroxyl group in compounds 8 affords compounds 9, which undergo cyclocondensation to provide compounds 10. Compounds 9 are alternatively obtained from compounds 3 by amidation reaction with a variety of aminoketones.

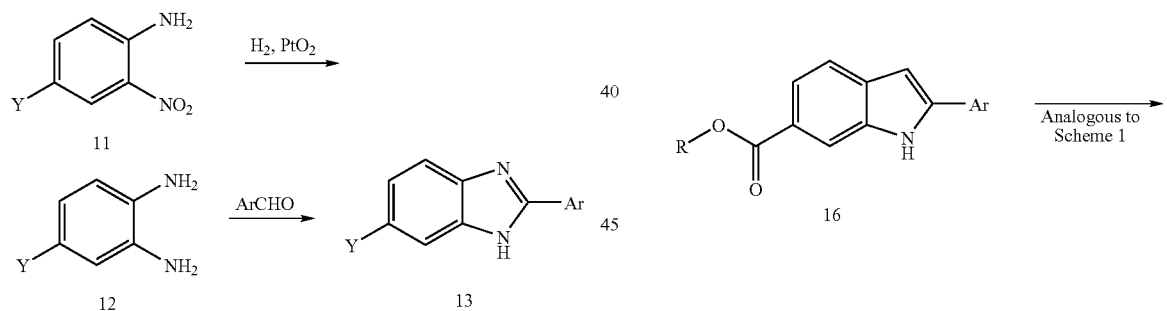

In another form of synthesis, the benzimidazole formation by cyclocondensation can be carried out at the later stage, with the eventual 5-substituent pre-installed on the ring. Commercially available 4-amino-3-nitrobenzoic acid are converted to compounds 11 analogous to Scheme 2.

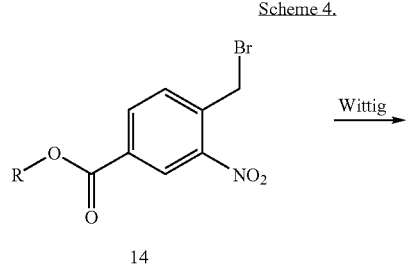

Compounds 14 are converted to compounds 17 by transformations such as Wittig olefination and reductive cyclization using $P(OEt)_3$, followed by procedures described in Scheme 1.

HPLC Method 10: 4.6 mm×5 cm Inersil C8-3 reverse phase, 3.0 μm particle size running a gradient of 10-90% MeCN/water (5 mM ammonium formate) over a period of 2 min at a flow rate of 4 mL/min at 50° C. DAD-UV detection, 220-600 nm.

Synthesis of Intermediates

The following intermediates are used in preparation of the Examples.

Intermediate 1

2-(2,6-Dichloro-phenyl)-3H-benzoimidazole-5-carboxylic acid hydrazide

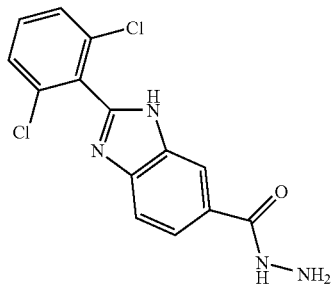

A. 2-(2,6-Dichloro-phenyl)-3H-benzoimidazole-5-carboxylic acid methyl ester

Slowly add a solution of $FeCl_3$ (1.46 g, 9.02 mmol) in DMSO (10 mL) to a stirring solution of 2,6-dichloro-benzaldehyde (5.27 g, 30.1 mmol) and 3,4-diamino-benzoic acid methyl ester (5.00 g, 30.1 mmol) in DMSO (90 mL). Allow the reaction to stir open to the air for 17 hr. Add additional $FeCl_3$ (0.73 g, 4.51 mmol). Stir for an additional 24 hr. Dilute with EtOAc (600 mL) and extract with water (3×50 mL). Dry the organic phase over $Na_2SO_4$ and evaporate the solvent. Triturate the residue with DCM to afford the desired product as a light tan solid: 1H NMR (400 MHz, MeOD) δ ppm 3.96 (s, 3H) 7.55-7.63 (m, 3H) 7.71 (d, J=8.21 Hz, 1H) 8.04 (dd, J=8.53, 1.58 Hz, 1H) 8.37 (br. s., 1H); (M+H)+ 320.9.

B. 2-(2,6-Dichloro-phenyl)-3H-benzoimidazole-5-carboxylic acid

Take 2-(2,6-Dichloro-phenyl)-3H-benzoimidazole-5-carboxylic acid methyl ester (1.00 g, 3.11 mmol) up in MeOH (6 mL) and 1 N NaOH (6 mL) and stir for 24 hr. Add additional 1 N NaOH (6 mL) and stir for an additional 30 hr. Concentrate under reduced pressure. Neutralize the concentrate at 0° C. by the dropwise addition of 1 N HCl (12 mL). Collect the resulting precipitate and wash with water followed by $Et_2O$. Dry the solid in a vac oven to afford the desired acid as a tan solid: 1H NMR (400 MHz, DMSO-d6) δ ppm 7.60-7.67 (m, 1H) 7.68 (s, 2H) 7.70 (d, J=2.15 Hz, 1H) 7.89 (d, J=8.46 Hz, 1H) 8.24 (br. s., 1H) 12.83 (br. s., 1H) 13.23 (br. s., 1H); (M+H)+ 306.9.

C. 2-(2,6-Dichloro-phenyl)-3H-benzoimidazole-5-carboxylic acid hydrazide

Suspend 2-(2,6-dichloro-phenyl)-3H-benzoimidazole-5-carboxylic acid (2.50 g, 8.14 mmol) in DCM (35 mL) and cool to 0° C. under $N_2$. Add DMF (0.2 mL). Add oxalyl chloride (0.75 mL, 8.55 mmol) in a dropwise manner. After 30 min allow the reaction to warm to room temp. After stirring at room temp for 1 hr. add TEA (2.38 mL, 17.1 mmol). Add the reaction mixture to a flask charged with hydrazine (2.56 mL, 81.4 mmol), DCM (40 mL), and THF (10 mL) at 0° C. under $N_2$. Upon addition allow the reaction mixture to warm to room temp. After 17 hr dilute the reaction with sat $NaHCO_3$ and collect the resulting solid. Take the solid up in EtOAc (800 mL) and extract with water (50 mL). Dry the organic phase over $Na_2SO_4$ and concentrate. Filter the resulting precipitate and wash with $Et_2O$ to yield the desired hydrazide as a tan solid: 1H NMR (400 MHz, DMSO-d6) δ ppm 4.52 (br. s., 2H) 7.58-7.66 (m+tautomer, 1H) 7.68 (s, 1H) 7.70 (d, J=2.02 Hz, 1H) 7.74 (br. s., 1H) 7.80 (tautomer, d, J=8.46 Hz, 1H) 8.04 (tautomer, br. s., 1H) 8.21 (tautomer, br. s., 1H) 9.78 (d, J=12.88 Hz, 1H) 13.08 (br. s., 1H); (M+H)+ 320.9.

Intermediate 2

2-(2,6-Dimethyl-phenyl)-3H-benzoimidazole-5-carboxylic acid

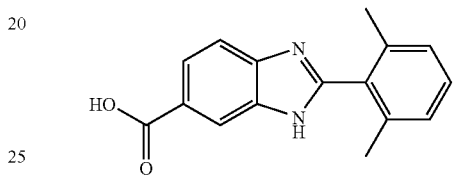

A. 2-(2,6-Dimethyl-phenyl)-3H-benzoimidazole-5-carboxylic acid methyl ester

To a solution of 10.0 g (60.2 mmol) of methyl-3,4-diaminobenzoate, 10.5320 (60.2 mmol) of 2,6-dichlorobenzaldehyde, and 100 mL DMSO was added 1.9642 g (9.64 mmol) of $FeCl_3$ portion-wise over 5 min. The dark brown solution was allowed to stir open to air at r.t. for 48 h. The reaction mixture was extracted with EtOAc, then washed with water, brine, and dried with $Na_2SO_4$. Most of the solvent was removed in vacuo until solid precipitated out. Filtered off solid to obtain the title compound. 1H NMR (400 MHz, DMSO-d6) δ ppm 2.15 (s, 6H) 3.93 (s, 3H) 7.26 (d, J=7.45 Hz, 2H) 7.37-7.42 (m, 1H) 7.65 (d, J=8.34 Hz, 0.5H) 7.80-7.83 (m, 0.5H) 7.87-7.95 (m, 1H) 8.16 (d, J=1.14 Hz, 0.4H) 8.33 (s, 0.5H) 13.00 (d, J=15.28 Hz, 1H). MS (m/z) 281.1 M (+1), $t_R$=1.30, Meth 10

B. 2-(2,6-Dimethyl-phenyl)-3H-benzoimidazole-5-carboxylic acid

To a tan suspension of 7.23 g (25.8 mmol) of 2-(2,6-Dimethyl-phenyl)-3H-benzoimidazole-5-carboxylic acid methyl ester in 50 mL MeOH was added 80 mL of NaOH (1N). Allowed to stir at r.t. for 48 h. The reddish/brown solution was dried, and to the residue was added 50 mL water, and brought to pH 4. Solid was filtered off to give near quantitative yield of title compound as an off-white solid. 1H NMR (400 MHz, DMSO-d6) δ ppm 2.03 (s, 6H) 7.14 (d, J=7.58 Hz, 2H) 7.27 (t, J=7.64 Hz, 1H) 7.50 (d, J=8.46 Hz, 0.5H) 7.67 (d, J=8.46 Hz, 0.5H) 7.78 (dd, J=15.09, 8.40 Hz, 1H) 8.03 (s, 0.5H) 8.20 (s, 0.5H) 12.64 (br. s., 1H) 12.85 (d, J=16.29 Hz, 1H). MS (m/z) 267.1 M (+1), $t_R$=0.87, Meth 10

EXAMPLES

The following Examples are intended to illustrate the invention and are not to be construed as being limitations thereon. If not mentioned otherwise, all evaporations are performed under reduced pressure, preferably between about 50 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

Example 1-1

6-[5-(4-Chloro-phenyl)-[1,3,4]oxadiazol-2-yl]-2-(2,6-dichloro-phenyl)-1H-benzoimidazole

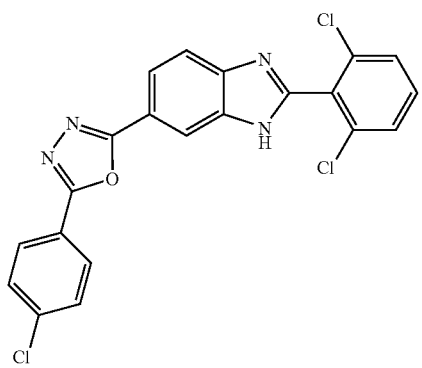

A. 4-Chloro-benzoic acid N'-[2-(2,6-dichloro-phenyl)-3H-benzoimidazole-5-carbonyl]-hydrazide To a yellow solution of 1.00 g (3.26 mmol) of 2-(2,6-Dimethyl-phenyl)-3H-benzoimidazole-5-carboxylic acid, 0.5554 g (3.26 mmol) of 4-chloro-benzoic hydrazide, and 18 mL of DMF was added 0.7501 g (3.91 mmol) of EDCI, and 0.5280 g (3.91 mmol) of HOBt. It was allowed to stir at r.t. for 6 h. 20 mL of water was and the resulting precipitates were collected by filtration to give the title compound as white solid. 1H NMR (400 MHz, DMSO-d6) δ ppm 7.59-7.72 (m, 5H) 7.81-7.89 (m, 1.5H) 7.93-7.99 (m, 2.5H) 8.17 (s, 0.5H) 8.34 (s, 0.5H) 10.51-10.66 (m, 2H) 13.23 (d, J=28.67 Hz, 1H). MS (m/z) 460.9 M (+1), $t_R$=1.18 (broad), Meth 10

B. 6-[5-(4-Chloro-phenyl)-[1,3,4]oxadiazol-2-yl]-2-(2,6-dichloro-phenyl)-1H-benzoimidazole To a 20 mL microwave vial was added 0.500 g (1.09 mmol) of 4-Chloro-benzoic acid N'-[2-(2,6-dichloro-phenyl)-3H-benzoimidazole-5-carbonyl]-hydrazide, 13 mL of THF, and 0.5187 g (2.18 mmol) of Burgess Reagent. The suspension was placed in the microwave at 150° C. for 20 min. The crude solution was concentrated and the residue was purified by silica gel column chromatography (ACN/DCM, 1:9 to 6:4) to give of the title compound. 1H NMR (400 MHz, DMSO-d6) δ ppm 7.62-7.67 (m, 1H) 7.68-7.74 (m, 4.5H) 7.78-7.81 (m, 0.6H) 7.94 (d, J=8.46 Hz, 0.5H) 8.02-8.10 (m, 1H) 8.17-8.22 (m, 2H) 8.33 (d, J=1.01 Hz, 0.4H) 8.49-8.52 (m, 0.6H) 13.36 (d, J=10.36 Hz, 1H). MS (m/z) 442.9 M (+1), $t_R$=1.49, Meth 10

Example 1-2

6-(5-tert-Butyl-[1,3,4]oxadiazol-2-yl)-2-(2,6-dichloro-phenyl)-1H-benzoimidazole

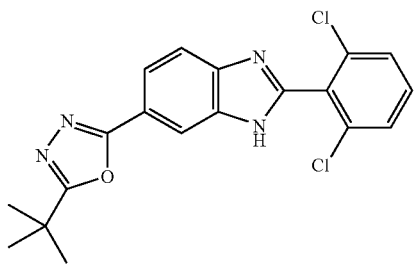

The title compound was synthesized analogous to Example 1-1, using pivalic hydrazide. The final reaction mixture was concentrated and the residue was purified by silica gel column chromatography (EtOAc/Hep, 1:9 to 7:3) to give the title compound. 1H NMR (400 MHz, DMSO-d6) δ ppm 1.46 (s, 9H) 7.62-7.67 (m, 1H) 7.69-7.73 (m, 2H) 7.77 (d, J=8.59 Hz, 0.5H) 7.90 (s, 1H) 7.95 (dd, J=8.46, 1.39 Hz, 0.5H) 8.18 (s, 0.5H) 8.34 (s, 0.5H) 13.28 (d, J=6.57 Hz, 1H). MS (m/z) 387.1 M (+1), $t_R$=1.36, Meth 10

Example 1-3

6-(5-Cyclohexyl-[1,3,4]oxadiazol-2-yl)-2-(2,6-dichloro-phenyl)-1H-benzoimidazole

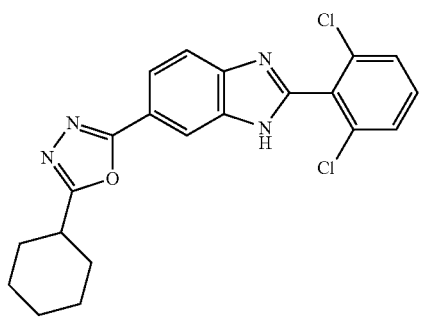

The title compound was synthesized analogous to Example 1-1. The final reaction mixture was concentrated and the residue was purified by silica gel column chromatography (EtOAc/Hep, 1:9 to 7:3) to give the title compound. 1H NMR (400 MHz, DMSO-d6) δ ppm 1.18-1.28 (m, 1H) 1.31-1.41 (m, 2H) 1.51-1.64 (m, 3H) 1.68-1.75 (m, 2H) 2.00-2.07 (m, 2H) 2.95-3.03 (m, 1H) 7.56-7.61 (m, 1H) 7.62-7.66 (m, 2H) 7.71 (br. s., 1H) 7.84 (br. s., 1H) 8.16 (d, J=56.46 Hz, 1H) 13.24 (s, 1H). MS (m/z) 413.1M (+1), $t_R$=1.50, Meth 10

Example 1-4

2-(2,6-Dichloro-phenyl)-6-(5-m-tolyl-[1,3,4]oxadiazol-2-yl)-1H-benzoimidazole

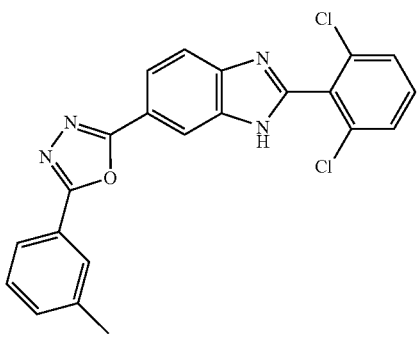

The title compound was synthesized analogous to Example 1-1. The final reaction mixture was concentrated and the residue was purified by silica gel column chromatography (MeOH/DCM, 0.5:9.5 to 1:9) to give the title compound. 1H NMR (400 MHz, DMSO-d6) δ ppm 2.46 (s, 3H) 7.46-7.50 (m, 1H) 7.54 (t, J=7.64 Hz, 1H) 7.64-7.69 (m, 1H) 7.70-7.75 (m, 2H) 7.82 (br.s., 0.5H) 7.97-8.04 (m, 2H) 8.07 (br. s., 1H) 8.35 (br. s., 0.3H) 8.52 (br. s., 0.5H) 13.36 (br. s., 1H). MS (m/z) 421.1 M (+1), $t_R$=1.47, Meth 10

Example 1-5

2-(2,6-Dichloro-phenyl)-6-[5-(3-fluoro-phenyl)-[1,3,4]oxadiazol-2-yl]-1H-benzoimidazole

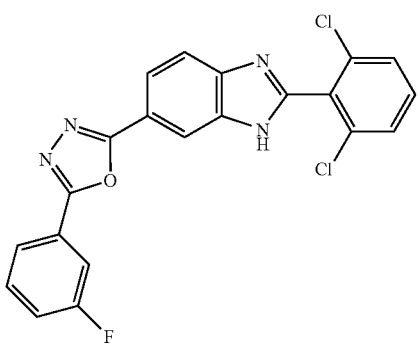

The title compound was synthesized analogous to Example 1-1. The final reaction mixture was concentrated and the residue was purified by silica gel column chromatography (EtOAc/Hep, 1:9 to 7:3) to give the title compound. 1H NMR (400 MHz, DMSO-d6) δ ppm 7.73-7.79 (m, 1H) 0.86-7.92 (m, 1H) 7.93-7.98 (m, 2.8H) 8.05 (br. s., 0.5H) 8.17 (br. s., 0.3H) 8.23-8.30 (m, 2H) 8.32 (d, J=6.32 Hz, 1H) 8.60 (br. s., 0.4H) 8.78 (br. s., 0.5H) 13.60 (br. s., 1H). MS (m/z) 425.0 M (+1), $t_R$=1.46, Meth 10

Example 1-6

6-(5-tert-Butyl-[1,2,4]oxadiazol-3-yl)-2-(2,6-dichloro-phenyl)-1H-benzoimidazole

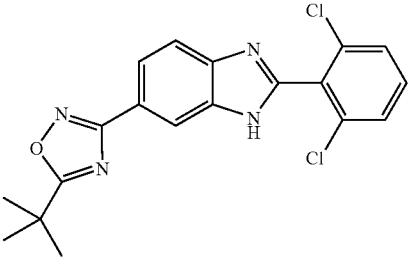

A. 2-(2,6-Dichloro-phenyl)-3H-benzoimidazole-5-carbonitrile

In a 20 ml scint. vial was added 0.500 g (2.86 mmol) of 2,6-Dichloro-benzaldehyde, 0.3804 g (2.86 mmol) of 3,4-diamino-benzonitrile, and 6 mL DMSO. To the brown solution was added 0.1995 g (1.23 mmol) of $FeCl_3$. Allowed stir at r.t. open to air for 18 h. Extracted with EtOAc and washed with water, and brine. Dried and purified on silica gel column chromatography (EtOAc/Hep, 1:9 to 7:3) to give of the title compound. 1H NMR (400 MHz, DMSO-d6) δ ppm 7.62-7.72 (m, 4H) 7.79 (br. s., 1H) 8.27 (br. s., 1H) 13.48 (br. s., 1H). MS (m/z) 288.1 M (+1), $t_R$=1.18, Meth 10

B. 2-(2,6-Dichloro-phenyl)-N-hydroxy-3H-benzoimidazole-5-carboxamidine

To a 25 ml rbf was added 0.100 g (0.347 mmol) of 2-(2,6-Dichloro-phenyl)-3H-benzoimidazole-5-carbonitrile, 2 mL of EtOH, 0.0482 g (0.694 mmol) of hydroxylamine HCl, and 0.048 mL (0.694 mmol) of $Et_3N$. It was allowed stir at 80° C., under reflux, for 4 h. It was reduced in vacuo and the crude was used directly in the next reaction. MS (m/z) 321.1 M (+1), $t_R$=0.93, Meth 10

C. 6-(5-tert-Butyl-[1,2,4]oxadiazol-3-yl)-2-(2,6-dichloro-phenyl)-1H-benzoimidazole To a 25 ml rbf was added 0.111 g (0.347 mmol) of 2-(2,6-Dichloro-phenyl)-N-hydroxy-3H-benzoimidazole-5-carboxamidine, 2.5 mL of pivalic anhydride (solvent). It was allowed to stir at 100° C. for 18 h. It was cooled to room temperature and extracted with EtOAc. The organic layer was washed with water, N KOH, and brine. It was dried with $MgSO_4$ and the volatiles were removed in vacuo. The crude was purified on silica gel column chromatography (EtOAc/Hep, 1:9 to 5:5) to give the title compound. 1H NMR (400 MHz, DMSO-d6) δ ppm 1.48 (s, 9H) 7.62-7.67 (m, 1H) 7.68-7.76 (m, 2.5H) 7.84-7.98 (m, 1.5H) 8.18 (br. s., 0.5H) 8.32 (br. s., 0.5H) 13.20 (br. s., 1H). MS (m/z) 387.1 M (+1), $t_R$=1.55, Meth 10

Example 1-7

6-(5-Cyclopropyl-[1,3,4]oxadiazol-2-yl)-2-(2,6-dichloro-phenyl)-1H-benzoimidazole

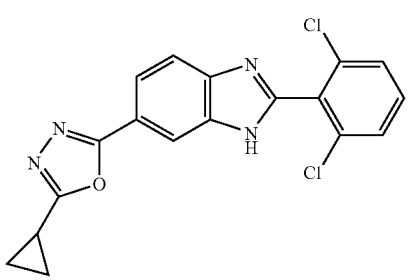

The title compound was synthesized analogous to Example 1-1. The final reaction mixture was concentrated and the residue was purified by silica gel column chromatography (EtOAc/Hep, 1:9 to 10:0) to give the title compound. 1H NMR (400 MHz, DMSO-d6) δ ppm 1.14-1.23 (m, 4H) 2.30-2.37 (m, 1H) 7.63-7.68 (m, 1H) 7.69-7.77 (m, 2.5H) 7.85-7.94 (m, 1.4H) 8.13 (s, 0.4H) 8.29 (s, 0.5H) 13.30 (s, 1H). MS (m/z) 371.0 M (+1), $t_R$=1.24, Meth 10

Example 1-8

6-(5-Benzyl-[1,3,4]oxadiazol-2-yl)-2-(2,6-dichloro-phenyl)-1H-benzoimidazole

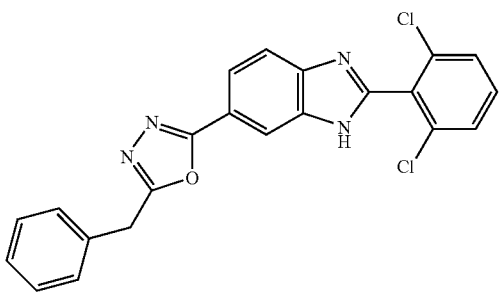

The title compound was synthesized analogous to Example 1-1. The final reaction mixture was concentrated and the residue was purified by silica gel column chromatography (EtOAc/Hep, 1:9 to 10:0) to give the title compound. 1H NMR (400 MHz, DMSO-d6) δ ppm 4.40 (s, 2H) 7.30-7.34 (m, 1H) 7.38-7.46 (m, 4H) 7.64-7.69 (m, 1H) 7.70-7.74 (m, 2H) 7.77 (d, J=8.46 Hz, 0.5H) 7.85-7.93 (m, 1.5H) 8.13 (s, 0.5H) 8.28 (s, 0.4H) 13.32 (br. s., 1H). MS (m/z) 421.1 M (+1), $t_R$=1.38, Meth 10

Example 1-9

2-(2,6-Dichloro-phenyl)-6-[5-(4-methoxy-phenyl)-[1,3,4]oxadiazol-2-yl]-1H-benzoimidazole

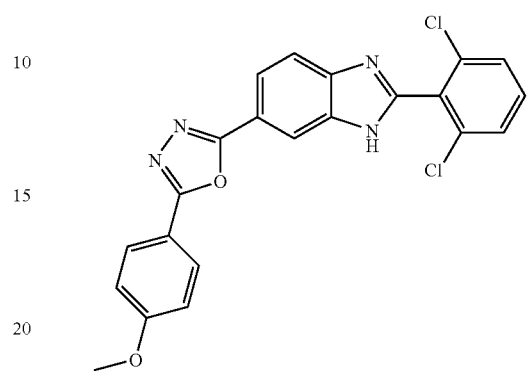

The title compound was synthesized analogous to Example 1-1. The final reaction mixture was concentrated and the residue was purified by silica gel column chromatography (EtOAc/Hep, 1:9 to 6:4) to give the title compound. 1H NMR (400 MHz, DMSO-d6) δ ppm 3.94 (s, 3H) 7.25 (d, J=8.84 Hz, 2H) 7.69-7.74 (m, 1H) 7.76-7.80 (m, 2H) 7.86 (d, J=8.46 Hz, 0.5H) 7.99 (d, J=7.07 Hz, 0.4H) 8.06-8.15 (m, 1H) 8.18 (d, J=8.72 Hz, 2H) 8.37 (br. s., 0.4H) 8.54 (br. s., 0.5H) 13.40 (br. s., 1H). MS (m/z) 437.1 M (+1), $t_R$=1.45, Meth 10

Example 1-10

6-[5-(4-Bromo-phenyl)-[1,3,4]oxadiazol-2-yl]-2-(2,6-dichloro-phenyl)-1H-benzoimidazole

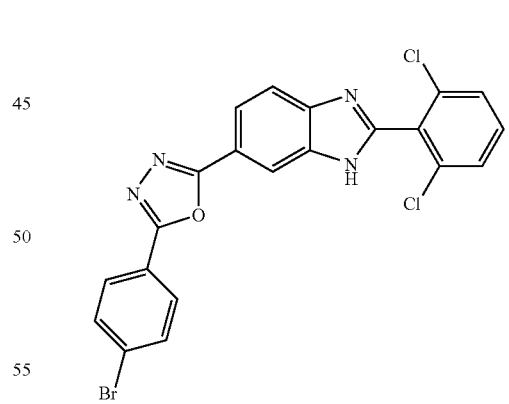

The title compound was synthesized analogous to Example 1-1. The final reaction mixture was concentrated and the residue was purified by silica gel column chromatography (EtOAc/Hep, 1:9 to 7.5:2.5) to give the title compound. 1H NMR (400 MHz, DMSO-d6) δ ppm 7.68-7.74 (m, 1H) 7.76-7.80 (m, 2H) 7.86 (d, J=8.21 Hz, 0.5H) 7.93 (d, J=8.59 Hz, 2H) 8.00 (d, J=6.82 Hz, 0.4H) 8.08-8.16 (m, 1H) 8.19 (d, J=8.46 Hz, 2H) 8.40 (br. s., 0.4H) 8.57 (br. s., 0.5H) 13.42 (br. s., 1H). MS (m/z) 486.9 M (+1), $t_R$=1.57, Meth 10

Example 1-11

2-(2,6-Dichloro-phenyl)-6-(5-p-tolyl-[1,3,4]oxadiazol-2-yl)-1H-benzoimidazole

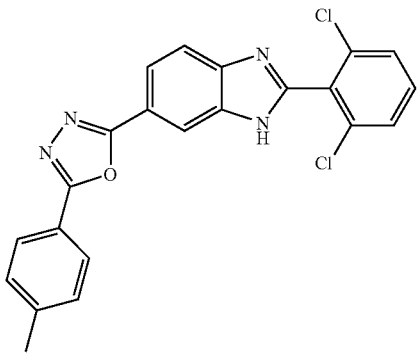

The title compound was synthesized analogous to Example 1-1. The final reaction mixture was concentrated and the residue was purified by silica gel column chromatography (EtOAc/Hep, 1:9 to 7:3) to give the title compound. 1H NMR (400 MHz, DMSO-d6) δ ppm 1.57 (s, 3H) 6.61 (d, J=7.96 Hz, 2H) 6.77-6.83 (m, 1H) 6.84-6.88 (m, 2H) 6.94 (d, J=8.34 Hz, 0.5H) 7.08 (d, J=8.46 Hz, 0.4H) 7.16-7.25 (m, 3H) 7.46 (s, 0.4H) 7.64 (s, 0.5H) 12.49 (d, J=7.33 Hz, 1H). MS (m/z) 421.1 M (+1), $t_R$=1.52, Meth 10

Example 1-12

2-(2,6-Dichloro-phenyl)-6-[5-(4-fluoro-phenyl)-[1,3,4]oxadiazol-2-yl]-1H-benzoimidazole

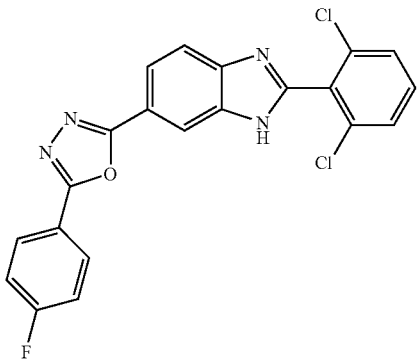

The title compound was synthesized analogous to Example 1-1. The final reaction mixture was concentrated and the residue was purified by silica gel column chromatography (EtOAc/Hep, 1:9 to 7:3) to give the title compound. 1H NMR (400 MHz, DMSO-d6) δ ppm 7.41-7.47 (m, 2H) 7.57-7.62 (m, 1H) 7.63-7.67 (m, 2H) 7.74 (d, J=8.46 Hz, 0.6H) 7.88 (d, J=8.59 Hz, 0.5H) 7.96-8.04 (m, 1H) 8.16-8.22 (m, 2H) 8.27 (d, J=0.88 Hz, 0.4H) 8.45 (s, 0.6H) 13.30 (d, J=11.24 Hz, 1H). MS (m/z) 424.9 M (+1), $t_R$=1.47, Meth 10

Example 1-13

6-(5-Butyl-[1,3,4]oxadiazol-2-yl)-2-(2,6-dichloro-phenyl)-1H-benzoimidazole

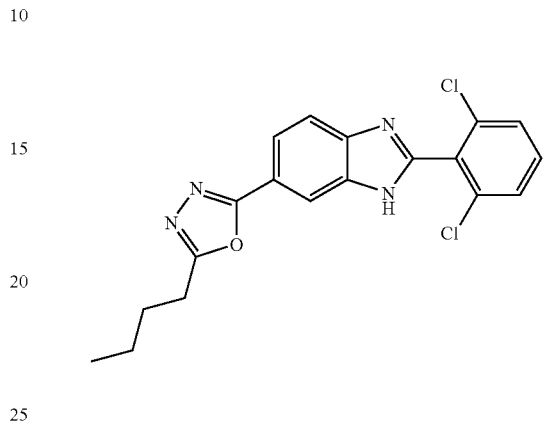

The title compound was synthesized analogous to Example 1-1. The final reaction mixture was concentrated and the residue was purified by silica gel column chromatography (EtOAc/Hep, 1:9 to 7:3) to give the title compound. 1H NMR (400 MHz, DMSO-d6) δ ppm 1.01 (t, J=7.39 Hz, 3H) 1.44-1.53 (m, 2H) 1.80-1.88 (m, 2H) 3.02 (t, J=7.45 Hz, 2H) 7.69-7.74 (m, 1H) 7.75-7.79 (m, 2H) 7.83 (d, J=8.46 Hz, 0.6H) 7.93-8.02 (m, 1.4H) 8.21 (s, 0.4H) 8.35 (s, 0.5H) 13.38 (s, 1H). MS (m/z) 387.3 M (+1), $t_R$=1.43, Meth 10

Example 1-14

6-(5-Cyclopentyl-[1,3,4]oxadiazol-2-yl)-2-(2,6-dichloro-phenyl)-1H-benzoimidazole

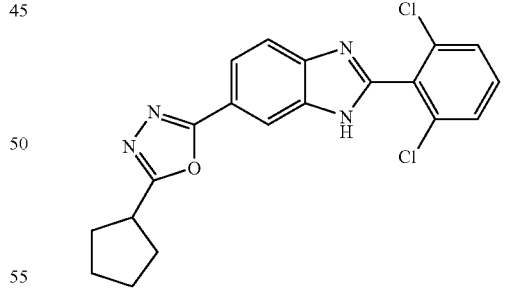

The title compound was synthesized analogous to Example 1-1. The final reaction mixture was concentrated and the residue was purified by silica gel column chromatography (EtOAc/Hep, 1:9 to 7:3) to give the title compound. 1H NMR (400 MHz, DMSO-d6) δ ppm 1.66-1.84 (m, 4H) 1.91-2.01 (m, 2H) 2.09-2.18 (m, 2H) 3.43-3.51 (m, 1H) 7.65-7.69 (m, 1H) 7.71-7.79 (m, 2.5H) 7.88-7.97 (m, 1.5H) 8.17 (s, 0.4H) 8.31 (s, 0.6H) 13.32 (br. s., 1H). MS (m/z) 399.1 M (+1), $t_R$=1.43, Meth 10

Example 1-15

2-(2,6-Dichloro-phenyl)-6-[5-(5-methyl-pyridin-3-yl)-[1,3,4]oxadiazol-2-yl]-1H-benzoimidazole

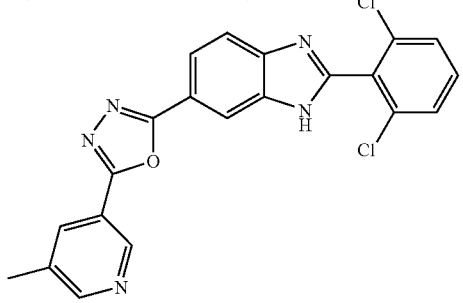

A. 5-Methyl-nicotinic acid N'-[2-(2,6-dichloro-phenyl)-3H-benzoimidazole-5-carbonyl]-hydrazide To a yellow solution of 0.200 g (0.623 mmol) of 2-(2,6-Dichloro-phenyl)-3H-benzoimidazole-5-carboxylic acid hydrazide (Intermediate 1), 0.0854 g (0.623 mmol) of 5-methyl nicotinic acid, and 5 mL of DMF was added 0.1453 g (0.747 mmol) of EDCI, and 0.1010 g (0.747 mmol) of HOBt. Allowed to stir at r.t. for 18 h. Added 5 mL of water, EtOAc and filtered off solid, to give 0.1680 g of the title compound. Used directly in next reaction. MS (m/z) 440.0 M (+1), $t_R$=1.00, Meth 10

B. 2-(2,6-Dichloro-phenyl)-6-[5-(5-methyl-pyridin-3-yl)-[1,3,4]oxadiazol-2-yl]-1H-benzoimidazole The title compound was synthesized analogous to step B in Example 1-1. The final reaction mixture was concentrated and the residue was purified by silica gel column chromatography (EtOAc/Hep, 1:9 to 10:0) to give the title compound. 1H NMR (400 MHz, DMSO-d6) δ ppm 2.58 (s, 3H) 7.76-7.81 (m, 1H) 7.83-7.87 (m, 2H) 7.94 (d, J=8.46 Hz, 0.6H) 8.08 (d, J=8.46 Hz, 0.4H) 8.18-8.26 (m, 1H) 8.48-8.55 (m, 1.4H) 8.68 (s, 0.6H) 8.81 (s, 1H) 9.29 (s, 1H) 13.50 (d, J=11.37 Hz, 1H). MS (m/z) 422.1 M (+1), $t_R$=1.31, Meth 10

Example 1-16

2-(2,6-Dimethyl-phenyl)-6-[5-(4-methoxy-phenyl)-[1,3,4]oxadiazol-2-yl]-1H-benzoimidazole

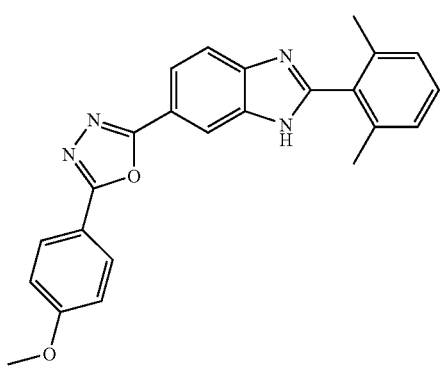

To a 5 mL microwave vial was added 0.2225 g (0.537 mmol) of 4-Methoxy-benzoic acid N'-[2-(2,6-dimethyl-phenyl)-3H-benzoimidazole-5-carbonyl]-hydrazide, 4 mL of THF, and 0.2558 g (1.07 mmol) of burgess reagent. The suspension was placed in the microwave at 150° C. for 15 min. The crude solution was concentrated and the residue was purified by silica gel column chromatography (EtOAc/DCM, 1:9 to 6:4) to give the title compound. 1H NMR (400 MHz, DMSO-d6) δ ppm 2.28 (s, 6H) 4.02 (s, 3H) 7.35 (dd, J=15.73, 8.27 Hz, 4H) 7.50 (t, J=7.64 Hz, 1H) 7.87 (d, J=8.34 Hz, 0.5H) 8.04 (d, J=8.46 Hz, 0.5H) 8.15 (dd, J=12.19, 8.65 Hz, 1H) 8.24-8.29 (m, 2H) 8.38 (s, 0.4H) 8.60 (s, 0.5H) 13.15 (d, J=14.27 Hz, 1H). MS (m/z) 397.2 M (+1), $t_R$=1.48, Meth 10

Example 1-17

2-(2,6-Dichloro-phenyl)-6-[5-(2-methoxy-pyridin-4-yl)-[1,3,4]oxadiazol-2-yl]-1H-benzoimidazole

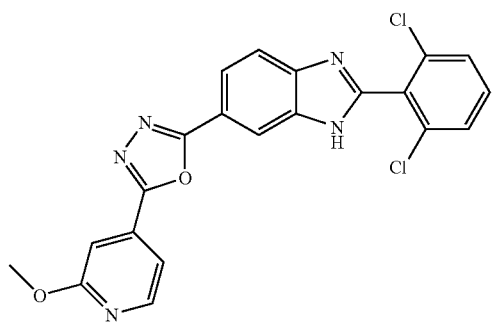

A. 2-Methoxy-isonicotinic acid N'-[2-(2,6-dichloro-phenyl)-3H-benzoimidazole-5-carbonyl]-hydrazide
(4b)

The title compound was synthesized analogous to step A in Example 1-15. Used directly in next reaction. MS (m/z) 456.0 M (+1), $t_R$=1.06, Meth 10

B. 2-(2,6-Dichloro-phenyl)-6-[5-(2-methoxy-pyridin-4-yl)-[1,3,4]oxadiazol-2-yl]-1H-benzoimidazole
(3b)

The title compound was synthesized analogous to step B in Example 1-1. The final reaction mixture was concentrated and the residue was purified by acidic HPLC (ACN/H$_2$O 3:7 to 10:0) (0.1% TFA in water) to give the title compound. 1H NMR (400 MHz, DMSO-d6) δ ppm 4.15 (s, 3H) 7.73 (s, 1H) 7.82-7.92 (m, 4H) 8.06 (d, J=8.46 Hz, 1H) 8.29 (dd, J=8.53, 1.58 Hz, 1H) 8.63 (d, J=5.31 Hz, 1H) 8.68 (s, 1H). MS (m/z) 438.0 M (+1), $t_R$=1.39, Meth 10

Example 1-18

2-(2,6-Dichloro-phenyl)-6-[5-(2-methoxy-pyridin-3-yl)-[1,3,4]oxadiazol-2-yl]-1H-benzoimidazole

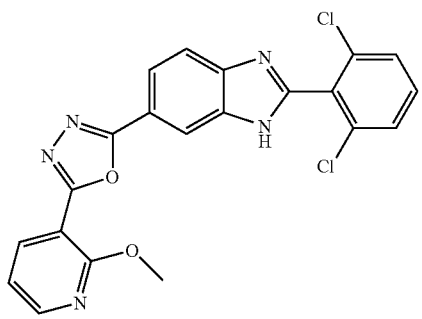

A. 2-Methoxy-nicotinic acid N'-[2-(2,6-dichloro-phenyl)-3H-benzoimidazole-5-carbonyl]-hydrazide (4c)

The title compound was synthesized analogous to step A in Example 1-15. Used directly in next reaction. MS (m/z) 456.0 M (+1), $t_R$=1.05, Meth 10

B. 2-(2,6-Dichloro-phenyl)-6-[5-(2-methoxy-pyridin-3-yl)-[1,3,4]oxadiazol-2-yl]-1H-benzoimidazole (3c)

The title compound was synthesized analogous to Example 1-1. The final reaction mixture was concentrated and the residue was purified by acidic HPLC (ACN/H$_2$O 3:7 to 10:0) (0.1% TFA in water) to give the title compound. 1H NMR (400 MHz, DMSO-d6) δ ppm 1H 4.20 (s, 3H) 7.40 (dd, J=7.52, 4.99 Hz, 1H) 7.77-7.82 (m, 1H) 7.86 (d, J=2.02 Hz, 1H) 7.85 (s, 1H) 8.01 (d, J=8.46 Hz, 1H) 8.17 (dd, J=8.53, 1.58 Hz, 1H) 8.51 (s, 1H) 8.61 (ddd, J=8.94, 7.11, 1.89 Hz, 2H). MS (m/z) 438.0 M (+1), $t_R$=1.32, Meth 10

Example 1-19

2-(2,6-Dichloro-phenyl)-6-[5-(6-trifluoromethyl-pyridin-3-yl)-[1,3,4]oxadiazol-2-yl]-1H-benzoimidazole

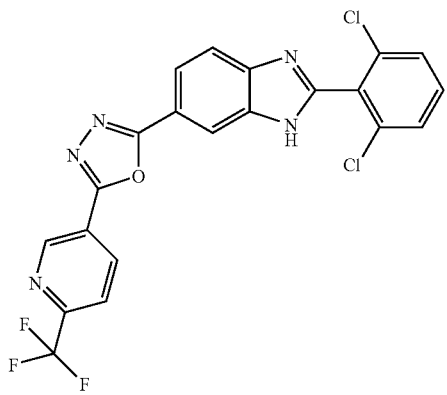

6-Trifluoromethyl-nicotinoyl chloride (119 uL, 0.817 mmol) was added to a solution of 2-(2,6-dichloro-phenyl)-3H-benzoimidazole-5-carboxylic acid hydrazide (250 mg, 0.778 mmol) in THF (10 mL) and EDIPA (149 uL, 0.856 mmol). The reaction was stirred for 17 hr. The reaction was diluted with EtOAc (75 mL) and extracted with water (20 mL). The organic phase was dried over Na$_2$SO$_4$ and concentrated. The concentrate was taken up in DMF (3 mL) and transferred to a microwave vial charged with Burgess reagent (555 mg, 2.33 mmol). The reaction was heated to 150° C. for 15 min by microwave irradiation. The reaction was diluted with EtOAc (75 mL) and extracted with water (15 mL). The organic phase was dried over Na$_2$SO$_4$ and concentrated. The concentrate was purified by silica gel column chromatography (15-40% ACN/DCM) and the resulting colorless film triturated with MeOH/DCM to afford the title compound (214 mg): 1H NMR (400 MHz, DMSO-d6) δ ppm 7.64-7.68 (m, 1H) 7.71 (s, 1H) 7.73 (d, J=2.02 Hz, 1H) 7.83 (tautomer, d, J=8.46 Hz, 1H) 7.97 (tautomer, d, J=8.59 Hz, 1H) 8.12 (dd, J=14.15, 8.72 Hz, 1H) 8.21 (d, J=8.34 Hz, 1H) 8.41 (tautomer, s, 1H) 8.60 (tautomer, s, 1H) 8.85 (d, J=8.34 Hz, 1H) 9.54 (s, 1H) 13.41 (d, J=14.15 Hz, 1H); LCMS $t_R$=1.53 min, MS (m/z) 476.7.

Example 1-20

4-{5-[2-(2,6-Dichloro-phenyl)-3H-benzoimidazol-5-yl]-[1,3,4]oxadiazol-2-yl}-benzonitrile

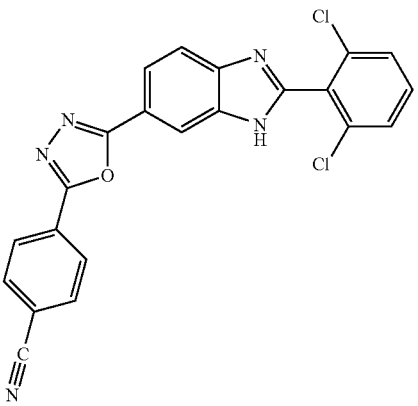

Combine 4-cyano-benzoic acid (120 mg, 0.817 mmol), 2-(2,6-dichloro-phenyl)-3H-benzoimidazole-5-carboxylic acid hydrazide (250 mg, 0.778 mmol), HATU (445 mg, 1.17 mmol), EDIPA (204 uL, 1.17 mmol), and DMF (5 mL) and stir for 25 hr. Dilute the reaction with EtOAc (75 mL) and extract with water (15 mL). Dry the organic phase over Na$_2$SO$_4$ and concentrate under reduced pressure. Take the concentrate up in DMF (3 mL) and add Burgess reagent (555 mg, 2.33 mmol). Heat the reaction to 150° C. for 20 min by microwave irradiation. Dilute the reaction with EtOAc (75 mL) and extract with water (20 mL). Dry the organic phase over Na$_2$SO$_4$ and concentrate under reduced pressure. Purify the concentrate by silica gel chromatography (10-40% ACN/DCM) to afford a white solid. Suspend the solid in water and stir for 6 hr. Collect the solid by filtration and wash with Et$_2$O. Dry the solid under vacuum at 40° C. for 2 days to afford the title compound (138 mg) as a white solid: 1H NMR (400 MHz, DMSO-d6) δ ppm 7.63-7.68 (m, 1H) 7.70-7.74 (m, 2H) 7.79-7.85 (tautomer, m, 1H) 7.96 (tautomer, d, J=8.59 Hz, 1H) 8.06-8.15 (m, 3H) 8.35-8.40 (m+tautomer, 2H) 8.52-8.60 (m, 1H) 13.39 (d, J=12.76 Hz, 1H); LCMS $t_R$=1.35 min, MS (m/z) 432.0.

Example 1-21

6-[5-(4-Chloro-phenyl)-[1,3,4]oxadiazol-2-yl]-2-(2,6-dimethyl-4-morpholin-4-yl-phenyl)-1H-benzoimidazole

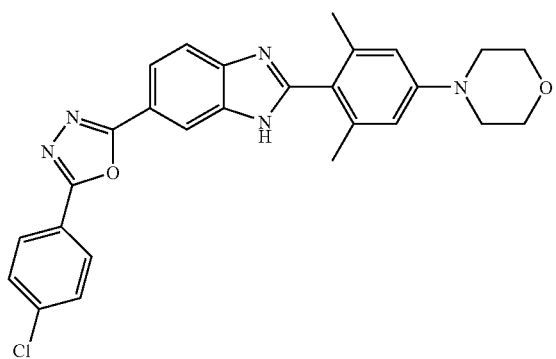

A. 2-(4-Hydroxy-2,6-dimethyl-phenyl)-3H-benzoimidazole-5-carboxylic acid methyl ester 3.65 g of methyl 3,4-diaminobenzoate and 3.3 g of 2,6-dimethyl-4-hydroxybenzaldehyde were stirred in 25 ml of DMSO at room temperature. A solution of 170 mg of $FeCl_3$ in 5 ml of DMSO was added by pipet and the reaction was stirred at the same temperature for 5 days. The reaction was then diluted with water and the resulting precipitates were collected by filtration. The filter cake was washed with water and heptane, and dried by air in the suction funnel to afford the title compound. LCMS retention T=1.01 min. (M+H)+= 297.01, Method 10.

B. 2-(2,6-Dimethyl-4-trifluoromethanesulfonyloxy-phenyl)-3H-benzoimidazole-5-carboxylic acid methyl ester 2.9 g of 2-(4-Hydroxy-2,6-dimethyl-phenyl)-3H-benzoimidazole-5-carboxylic acid methyl ester was stirred in 20 ml of anhydrous DMF at room temperature under nitrogen atmosphere. It was treated with 1.9 ml of diisopropyl ethyl amine and 3.8 g of $PhNTf_2$ and the reaction was stirred at the same temperature for 3 days. The reaction was diluted with water and the resulting precipitates were collected by filtration. The filter cake was washed with water and dried by air in the suction funnel to afford the title compound. LCMS retention T=1.50 min. MS (m/z)=429.0. Method 10.

C. 2-(2,6-Dimethyl-4-morpholin-4-yl-phenyl)-3H-benzoimidazole-5-carboxylic acid methyl ester To a stirred solution of 2.4 g of 2-(2,6-Dimethyl-4-trifluoromethanesulfonyloxy-phenyl)-3H-benzoimidazole-5-carboxylic acid methyl ester in 6 ml of toluene was added 4 ml of morpholine, 280 mg of $Pd_2(dba)_3$, 400 mg of P(biphenyl)$_t$-Bu$_2$ and 2.0 g of $K_3PO_4$. The reaction vessel sealed and heated at 80° C. overnight. The reaction was cooled to room temperature and diluted with water and heptane. The resulting precipitates were collected by filtration, washed with water and dried to afford the title compound. LCMS retention T=1.14 min, m/z=366.2, Method 10.

D. 2-(2,6-Dimethyl-4-morpholin-4-yl-phenyl)-3H-benzoimidazole-5-carboxylic acid

To a stirred solution of 1.83 g of the crude 2-(2,6-Dimethyl-4-morpholin-4-yl-phenyl)-3H-benzoimidazole-5-carboxylic acid methyl ester in 20 ml of THF, 20 ml of water and 400 mg of LiOH were added and it was stirred at room temperature overnight. The reaction mixture was diluted with 100 ml of water and neutralized by 6N HCl. The resulting precipitates were collected by filtration and dried to afford the title compound. LCMS retention T=0.75 min. m/z=352.1. Method 10.

E. 4-Chloro-benzoic acid N'-[2-(2,6-dimethyl-4-morpholin-4-yl-phenyl)-3H-benzoimidazole-5-carbonyl]-hydrazide To a stirred solution of the crude 2-(2,6-Dimethyl-4-morpholin-4-yl-phenyl)-3H-benzoimidazole-5-carboxylic acid in 10 ml of DMF was added 900 mg of 4-chlorobenzoic acid hydrazide, 1.1 g of EDCI and 700 mg of HOBT. The reaction was stirred at room temperature under nitrogen atmosphere for 5 hours. The reaction mixture was diluted with water and the resulting precipitates were collected by filtration and purified by column chromatography (DCM:MeOH=20:1) to give the title compound. LCMS ret T=1.19 min, m/z=504.1, Method 10.

F. 6-[5-(4-Chloro-phenyl)-[1,3,4]oxadiazol-2-yl]-2-(2,6-dimethyl-4-morpholin-4-yl-phenyl)-1H-benzoimidazole 252 mg of 4-Chloro-benzoic acid N'-[2-(2,6-dimethyl-4-morpholin-4-yl-phenyl)-3H-benzoimidazole-5-carbonyl]-hydrazide was placed in a microwave tube and dissolved in 4 ml of THF. 300 mg of (methoxycarbonylsulfamoyl)triethylammonium hydroxide (Burgess Reagent) was added and the tube was sealed and microwaved at 150° C. for 30 minutes. The reaction was then diluted with water and heptane. The precipitates were collected by filtration and purified by column chromatography (heptane:ethyl acetate=1:1 to 1:2) to provide the title compound. LCMS ret T=1.44 min, m/z=486.1, method 10. 1H NMR (400 MHz, MeOD) ☐ ppm 2.29 (br. s., 6H) 3.36 (br. s., 5H) 3.99 (br. s., 4H) 6.95 (br. s., 2H) 7.81 (s, 2H) 7.95 (br.s., 1H) 8.25 (br. s., 1H) 8.32 (br. s., 2H) 8.56 (br. s., 1H).

Example 1-22

6-[5-(4-Chloro-phenyl)-[1,3,4]oxadiazol-2-yl]-2-(3,5-dichloro-pyridin-4-yl)-1H-benzoimidazole

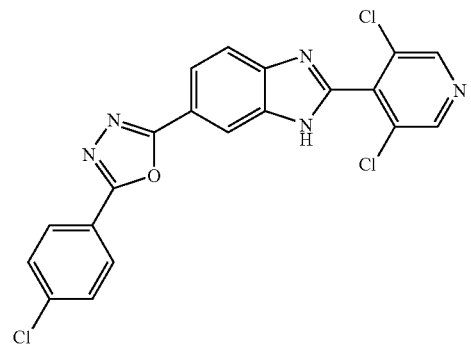

A. 2-(3,5-Dichloro-pyridin-4-yl)-3H-benzoimidazole-5-carboxylic acid methyl ester The title compound was prepared analogous to step A in Intermediate 2. 1H NMR (400 MHz, DMSO-d6) δ ppm 3.88 (s, 3H) 7.76 (br. s., 1H) 7.92 (d, J=6.32 Hz, 1H) 8.32 (br. s., 1H) 8.90 (s, 2H) 13.44 (s, 1H). MS (m/z) 322.0 M (+1), $t_R$=1.08, Meth 10

B. 2-(3,5-Dichloro-pyridin-4-yl)-3H-benzoimidazole-5-carboxylic acid

The title compound was prepared analogous to step B in Intermediate 2. 1H NMR (400 MHz, DMSO-d6) δ ppm 7.73 (br. s., 1H) 7.91 (d, J=6.95 Hz, 1H) 8.29 (br. s., 1H) 8.90 (s, 2H) 12.87 (br. s., 1H) 13.41 (br. s., 1H). MS (m/z) 308.0 M (+1), $t_R$=0.77, Meth 10.

C. 4-Chloro-benzoic acid N'-[2-(3,5-dichloro-pyridin-4-yl)-3H-benzoimidazole-5-carbonyl]-hydrazide The title compound was prepared analogous to step A of Example 1-1. The crude was used directly in next reaction. MS (m/z) 461.9 M (+1), $t_R$=1.10 (broad), Meth 10

D. 6-[5-(4-Chloro-phenyl)-[1,3,4]oxadiazol-2-yl]-2-(3,5-dichloro-pyridin-4-yl)-1H-benzoimidazole The title compound was prepared analogous to step B of Example 1-1. The final reaction mixture was concentrated and the residue was purified on silica gel column chromatography (ACN/DCM, 1:9 to 6:4) to give the title compound. 1H NMR (400 MHz, DMSO-d6) δ ppm 7.69-7.76 (m, 2H) 7.91 (d, J=6.82 Hz, 1H) 8.09 (d, J=8.21 Hz, 1H) 8.17-8.23 (m, 2H) 8.49 (br. s., 1H) 8.92 (s, 2H) 13.50 (br. s., 1H). MS (m/z) 443.9 M (+1), $t_R$=1.42, Meth 10

Example 1-23

6-[5-(4-Chloro-phenyl)-[1,3,4]oxadiazol-2-yl]-2-(2,6-dimethyl-phenyl)-1H-benzoimidazole

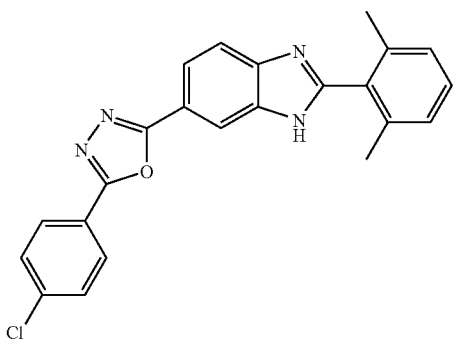

The title compound was prepared analogous to Example 1-16. 1H NMR (400 MHz, DMSO-d6) δ ppm 2.12 (s, 6H) 7.22 (d, J=7.58 Hz, 2H) 7.35 (t, J=7.58 Hz, 1H) 7.68-7.75 (m, 2.5H) 7.89 (d, J=8.46 Hz, 0.5H) 7.98-8.05 (m, 1H) 8.19 (t, J=7.71 Hz, 2H) 8.25 (s, 0.5H) 8.47 (s, 0.5H) 13.01 (d, J=16.04 Hz, 1H). MS (m/z) 401.1 M (+1), $t_R$=1.44, Meth 10

Example 1-24

2-(2,6-Dichloro-phenyl)-6-(4,5-diphenyl-oxazol-2-yl)-1H-benzoimidazole

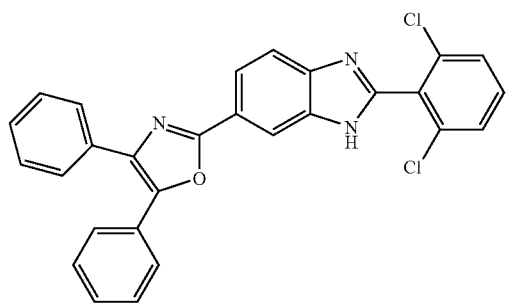

A. 2-(2,6-Dichloro-phenyl)-3H-benzoimidazole-5-carboxylic acid ((1R,2S)-2-hydroxy-1,2-diphenyl-ethyl)-amide To a 20 mL scint. vial was added 0.200 g (0.651 mmol) of Intermediate 1, 0.0825 g (0.716 mmol) of 2-amino cyclohexanol, 5 mL of DMF, 0.1815 mL (1.30 mmol) of $Et_3N$, and 0.4952 g (1.3 mmol) of HATU. Allowed to stir at r.t. for 18 h. Extracted with EtOAc, washed with water, brine, and dried with $Na_2SO_4$. The title compound was prepared analogous to step A of Example 1-24. Used directly in next reaction. MS (m/z) 502.1 M (+1), $t_R$=1.34, Meth 10

B. 2-(2,6-Dichloro-phenyl)-3H-benzoimidazole-5-carboxylic acid ((R)-2-oxo-1,2-diphenyl-ethyl)-amide The title compound was prepared analogous to step B of Example 1-24. The crude was used directly in next reaction. MS (m/z) 500.1 M (+1), $t_R$=1.46, Meth 10

C. 2-(2,6-Dichloro-phenyl)-6-(4,5-diphenyl-oxazol-2-yl)-1H-benzoimidazole

The title compound was prepared analogous to Example 1-24 with the exception that the brown solution was concentrated and the residue purified on silica gel column chromatography (EtOAc/DCM, 1:9 to 6:4) to give the title compound. 1H NMR (400 MHz, DMSO-d6) δ ppm 7.42-7.56 (m, 6.5H) 7.64-7.80 (m, 8H) 7.91 (d, J=8.59 Hz, 0.6H) 8.04-8.12 (m, 1H) 8.29 (d, J=0.88 Hz, 0.5H) 8.46 (d, J=0.76 Hz, 0.5H) 13.27 (s, 1H). MS (m/z) 482.1 M (+1), $t_R$=1.79, Meth 10

Example 1-25

6-[5-(4-Chlorophenyl)-4-methyl-oxazol-2-yl]-2-(2,6-dichlorophenyl)-1H-benzoimidazole

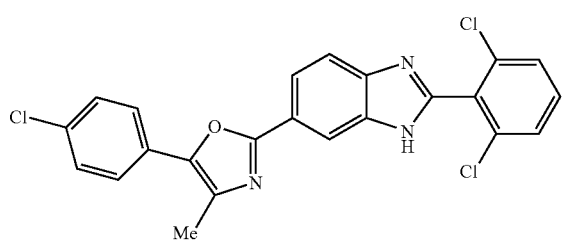

A. 2-Bromo-1-(4-chlorophenyl)-propan-1-one

A stirred solution of p-chloropropiophenone (2.0 g, 11.9 mmol) in dichloromethane (35 mL) was treated with one drop of 48% HBr and one drop of bromine. When the color had discharged, bromine (608 µL, 1.90 gm, 11.9 mmol) was added dropwise. The solution was stirred until 15 min after the color had fully discharged, then the mixture was concentrated under reduced pressure to give the title compound.

B. N,N-Diformyl-2-amino-1-(4-chlorophenyl)-propiophenone

A solution of 2-bromo-1-(4-chlorophenyl)-propan-1-one from step A and sodium diformyl amide (1.24 gm, 13.0 mmol) in DMF (10 mL) was stirred at RT for 18 h. The solution was poured into ethyl acetate and extracted once with water and five times with brine. The organic phase was dried, filtered, and the solvent removed under reduced pressure. The residue was purified by chromatography using a gradient of 20-50% heptane/ethyl acetate to give the title compound.

C. 1-(4-Chlorophenyl)-2-aminopropiophenone hydrochloride

A solution of N,N-diformyl-2-amino-1-(4-chlorophenyl)-propiophenone (2.36 g, 9.85 mmol) in 40 mL 19:1 ethanol/conc. HCl was stirred at RT for 18 h. The solvent was removed under reduced pressure to give the title compound.

D. 2-(2,6-Dichlorophenyl)-3H-benzimidazole-5-carboxylic acid [2-(4-chlorophenyl)-1-methyl-2-oxoethyl]-amide A mixture of 1-(4-chlorophenyl)-2-aminopropiophenone hydrochloride (365 mg, 1.66 mmol), 2-(2,6-dichlorophenyl)-3H-benzimidazole-5-carbonyl chloride hydrochloride (600 mg, 1.66 mmol) (Example 1-27, step E), and triethylamine (924 µL, 671 mg, 6.63 mmol) in THF (25 mL) was stirred at RT for 18 hrs. The solution was poured into ethyl acetate and extracted with water and brine. The organic layer was dried, filtered, and the solvent removed under reduced pressure. The residue was chromatographed using a gradient of 50-90% heptane/ethyl acetate to give the title compound. MS: m/z 473.9 (M+1); $H^1$-NMR (acetone-d6): δ 8.57 (m, broad, 1H), 8.37 (m, 3H), 8.11 (m, broad, 1H), 7.83 (m, 5H), 5.92 (quintet, J=7.2 Hz, 1H), 1.75 (d, J=7.0 Hz, 3H).

E. 6-[5-(4-Chlorophenyl)-4-methyloxazol-2-yl]-2-(2,6-dichlorophenyl)-1H-benzimidazole A mixture of 2-(2,6-dichlorophenyl)-3H-benzimidazole-5-carboxylic acid [2-(4-chlorophenyl)-1-methyl-2-oxoethyl]-amide (480 mg, 1.02 mmol) and Burgess Reagent (848 mg, 4.06 mmol) in THF (10 mL) was heated in a microwave apparatus at 150° C. for 30 min. The mixture was poured into ethyl acetate and extracted with water and brine. The organic layer was dried, filtered, and the solvent removed under reduced pressure. The residual oil was triturated with acetonitrile to afford the title compound. $H^1$-NMR (DMSO-d6): δ 8.40 (s, broad, 0.5H), 8.22 (s, broad, 0.5H), 8.0 (m, 1H), 7.72 (m, 8H), 2.47 (s, 3H). MS: m/z 455.9 (M+1); High resolution MS (M+H): theory: 454.0281, measured: 454.0279.

Example 1-26

6-[5-(4-Chlorophenyl)-oxazol-2-yl]-2-(2,6-dichlorophenyl)-1H-benzoimidazole

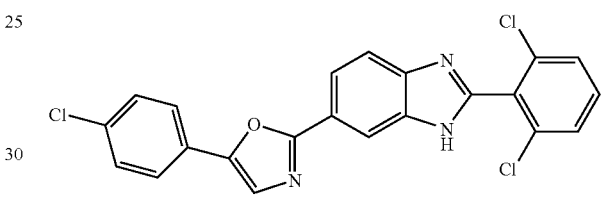

A. N,N-Diformyl-2-amino-1-(4-chlorophenyl)-acetophenone

A mixture of 2-bromo-1-(4-chlorophenyl)-acetophenone (500 mg, 2.14 mmol) and sodium diformyl amide (244 mg, 2.57 mmol) in DMF (5 mL) was stirred at RT for 18 h. The mixture was poured into ethyl acetate, extracted once with water and five times with brine. The organic layer was dried over magnesium sulfate, filtered, and the solvent removed under reduced pressure. The residue was chromatographed using a gradient of 20-60% heptane/ethyl acetate to afford the title compound.

B. 1-Amino-2-(4-chlorophenyl)-acetophenone hydrochloride

A solution of N,N-diformyl-2-amino-1-(4-chlorophenyl)-acetophenone (490 mg, 2.14 mmol) in 20 mL of 19:1 ethanol/conc. HCl was stirred at RT for 18 h. The solvent was removed under reduced pressure to afford the title compound.

C. 2-(2,6-Dichlorophenyl)-3H-benzoimidazole-5-carboxylic acid methyl ester

To a solution of 3,4-diaminobenzoic acid methyl ester (3.32 g, 20 mmol) and 2,6-dichlorobenzaldehyde (3.5 g, 20 mmol) in DMF (20 mL)+water (2 mL) was added oxone (2.46 g, 4 mmol). The mixture was stirred at RT for 18 h then EtOAc was added. The mixture was washed with water and brine then was dried over sodium sulfate. The solvent was removed under reduced pressure to give the title compound as a yellow solid.

D. 2-(2,6-Dichlorophenyl)-3H-benzoimidazole-5-carboxylic acid

To a solution of 2-(2,6-dichlorophenyl)-3H-benzoimidazole-5-carboxylic acid methyl ester (5.8 g) in 40 mL of MeOH/THF (1:1) was added 1N NaOH (20 mL). The mixture was stirred at RT for 18 h then 1N HCl was added until pH 3. The resulting precipitate was filtered, washed with water and dried under reduced pressure to give the title compound.

E. 2-(2,6-Dichlorophenyl)-3H-benzimidazole-5-carbonyl chloride hydrochloride A mixture of 2-(2,6-dichlorophenyl)-3H-benzoimidazole-5-carboxylic acid (5 g) in thionyl chloride (10 mL) containing a catalytic quantity of DMF was stirred at RT for 18 h. Methylene chloride was added and the resulting solid was filtered, washed with methylene chloride and dried under reduced pressure to give the title compound as an off-white solid.

F. 2-(2,6-Dichlorophenyl)-3H-benzimidazole-5-carboxylic acid [2-(4-chlorophenyl)-2-oxo-ethyl]-amide A mixture of 1-amino-2-(4-chlorophenyl)-acetophenone hydrochloride (320 mg, 1.55 mmol), 2-(2,6-dichlorophenyl)-3H-benzimidazole-5-carbonyl chloride hydrochloride (562 mg, 1.55 mmol), and triethylamine (866 mL, 629 mg, 6.21 mmol) in THF (20 mL) was stirred at RT for 18 h. The mixture was poured into ethyl acetate and extracted with water and brine. The organic phase was dried, filtered, and the solvent removed under reduced pressure. The residue was purified by chromatography using a gradient of 50-90% heptane/ethyl acetate to give the title compound as a solid. MS: m/z 460.0 (M+1). H$^1$-NMR (DMSO-d6): δ 13.21 (s, 0.45H), 13.15 (s, 0.55H), 8.93 (m, 1H), 8.32 (s, 0.55H), 8.14 (s, 0.45H), 8.08 (d, J=8.6 Hz, 2H), 7.82 (m, 2H), 7.66 (m, 5H), 4.79 (d, J=5.4 Hz, 2H).

G. 6-[5-(4-Chlorophenyl)-oxazol-2-yl]-2-(2,6-dichlorophenyl)-1H-benzimidazole A mixture of 2-(2,6-dichlorophenyl)-3H-benzimidazole-5-carboxylic acid [2-(4-chlorophenyl)-2-oxo-ethyl]-amide (310 mg, 0.68 mmol) and Burgess reagent (644 mg, 2.70 mmol) THF (10 mL) was heated in a microwave apparatus at 150° C. for 30 min. The mixture was poured into ethyl acetate and extracted with water and brine. The organic phase was dried, filtered, and the solvent removed under reduced pressure. The residue was purified by chromatography using a gradient of 40-75% heptane/ethyl acetate followed by a second chromatography with dichloromethane/acetone (0-20% gradient) to give the title compound. H$^1$-NMR (DMSO-d6): δ 8.69 (m, broad, 1H), 8.34 (d, J=8.5 Hz, 1H), 8.13 (d, J=8.2, Hz 2H), 8.04 (s, broad, 1H), 7.95 (s, 1H), 7.84 (m, 3H), 7.75 (d, J=8.6 Hz, 2H). MS: m/z 441.9 (M+1); High resolution MS (M+H): theory 440.0124, measured 440.0126.

Example 1-27

6-[5-(4-Chloro-phenyl)-[1,3,4]oxadiazol-2-yl]-2-(2,6-dichloro-4-morpholin-4-yl-phenyl)-1H-benzoimidazole

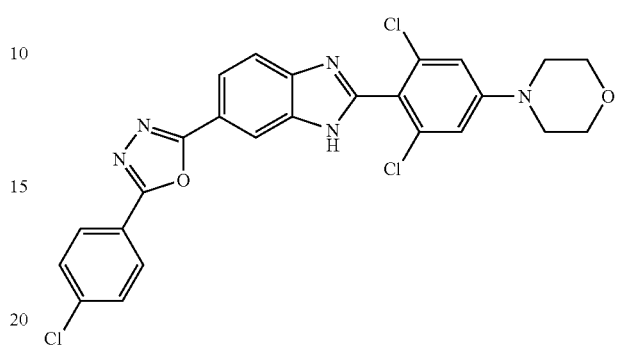

A. 4-Chloro-benzoic acid N'-(4-amino-3-nitro-benzoyl)-hydrazide

To 4-Chloro-benzoic acid hydrazide (5.0 g, 29 mmol) and 4-Amino-3-nitro-benzoic acid (5.3 g, 29 mmol) in DMF (100 mL) was added HOBT (3.9 g, 29 mmol), and EDCI (5.5 g, 29 mmol), followed by triethylamine (12.1 mL, 87 mmol). The mixture was stirred at ambient temperature for 18 hours. Water (50 mL) was added to the reaction mixture. The precipitate was collected by filtration, washed with water, and dried under vacuum to provide the title compound as a yellow solid. 1H NMR (DMSO-d6, 400 MHz) δ ppm 7.08 (d, J=8.97 Hz, 1H) 7.61 (m, 2H) 7.82-7.97 (m, 5H) 8.66 (d, J=2.15 Hz, 1H) 10.52 (s, 1H) 10.57 (s, 1H; (M+H)$^+$=335.0

B. 2,6-Dichloro-4-morpholin-4-yl-benzaldehyde

Add sec-BuLi (1.4M in cyclohexane, 5.44 mL) in a dropwise manner to a solution of 4-(3,5-Dichloro-phenyl)-morpholine (Tetrahedron (2001), 57(36), 7657-7664, 1.60 g, 6.93 mmol) in dry THF (20 mL) under N$_2$ at −78° C. Allow to stir for 30 min. Slowly add DMF (2.68 mL, 34.7 mmol) to the cold solution. Upon disappearance of the starting material by TLC, warm the reaction to 0° C. Quench the reaction by addition of H$_2$O (15 mL) and extract the mixture with EtOAc (150 mL). Dry the organic phase over Na$_2$SO$_4$ and evaporate the solvent. Triturate the resulting solid with Et$_2$O to yield the title compound. Evaporate the filtrate to yield another crop of the title compound as a yellow solid: 1H NMR (400 MHz, ACETONITRILE-d3) δ ppm 3.46-3.54 (m, 4H) 3.85-3.93 (m, 4H) 7.06 (s, 2H) 10.44 (s, 1H); MS (m/z) 260.0 (M+1).

C. 4-[5-(4-Chloro-phenyl)-[1,3,4]oxadiazol-2-yl]-2-nitro-phenylamine

To a 20 mL microwave vial was added 1.00 g (2.99 mmol) of 4-Chloro-benzoic acid N'-(4-amino-3-nitro-benzoyl)-hydrazide, 12 mL of THF, and 1.9934 g (8.36 mmol) of burgess reagent. The suspension was placed in the microwave at 150° C. for 30 min. To the orange/yellow suspension was added 5 mL of MeOH and the resulting precipitates were collected by filtration and dried to give the title compound. 1H NMR (400 MHz, DMSO-d6) δ ppm 7.31 (d, J=8.97 Hz, 1H) 7.80 (d, J=8.59 Hz, 2H) 8.12-8.19 (m, 2.7H) 8.25 (d, J=8.59 Hz, 2H) 8.77 (d, J=2.02 Hz, 1H). MS (m/z) 317.0 M (+1), $t_R$=1.33, Meth 10

D. 4-[5-(4-Chloro-phenyl)-[1,3,4]oxadiazol-2-yl]-benzene-1,2-diamine

To a 25 mL rbf was added 0.4137 g (1.31 mmol) of 4-[5-(4-Chloro-phenyl)-[1,3,4]oxadiazol-2-yl]-2-nitro-phenylamine, 4 mL of THF/EtOH (1:1). Vacuum flushed 3×, then added 0.1655 g of PtO$_2$ (40% by weight) as a slurry in 2 mL of THF/EtOH (1:1). It was flushed with H$_2$ 3× and allowed to stir at r.t. for 18 h. 10 ml DCM and Celite was added and it was let stir 1 h. The mixture was then filtered through Celite pad, and the filter cake was rinsed with 20 mL DCM. The filtrate was reduced in vacuo to give the title compound. 1H NMR (400 MHz, DMSO-d6) δ ppm 4.85 (br. s., 1.7H) 5.31 (br. s., 1.7H) 6.62 (d, J=8.08 Hz, 1H) 7.19 (dd, J=8.08, 1.89 Hz, 1H) 7.26 (d, J=2.02 Hz, 1H) 7.66-7.70 (m, 2H) 8.02-8.06 (m, 2H). MS (m/z) 287.2 M (+1), $t_R$=1.18, Meth 10

E. 6-[5-(4-Chloro-phenyl)-[1,3,4]oxadiazol-2-yl]-2-(2,6-dichloro-4-morpholin-4-yl-phenyl)-1H-benzoimidazole To a 50 ml rbf was added 0.2250 g (0.785 mmol) 4-[5-(4-Chloro-phenyl)-[1,3,4]oxadiazol-2-yl]-benzene-1,2-diamine, 0.2041 g (0.785 mmol) of 2,6-Dichloro-4-morpholin-4-yl-benzaldehyde, and 5 mL of DMSO. To this dark brown solution was added 0.0190 g (0.118 mmol) of FeCl$_3$. It was allowed to stir open to air for 18 h. The crude was then extracted with EtOAc, and the combined extracts were washed with water, brine and dried with Na$_2$SO$_4$. The volatiles were removed in vacuo and the concentrate was purified on silica gel (ACN/DCM, 1:9 to 10:0) to give the title compound. 1H NMR (400 MHz, DMSO-d6) δ ppm 3.30 (d, J=5.05 Hz, 4H) 3.71-3.77 (m, 4H) 7.17 (s, 2H) 7.70-7.75 (m, 2H) 7.90 (d, J=8.72 Hz, 1H) 7.99-8.07 (m, 1H) 8.19 (d, J=8.21 Hz, 2H) 8.27 (br. s., 1H) 8.47 (s, 1H) 13.17 (d, J=8.97 Hz, 1H). MS (m/z) 528.0 M (+1), $t_R$=1.41, Meth 10

Example 1-28

{5-[2-(2,6-Dichloro-phenyl)-3H-benzoimidazol-5-yl]-[1,3,4]oxadiazol-2-yl}-pyridin-4-yl-amine

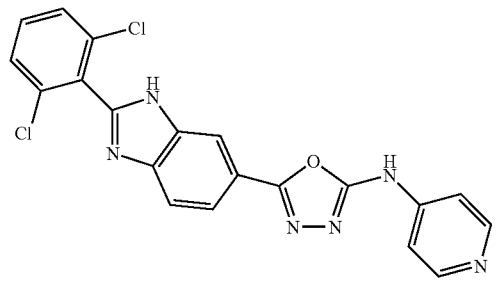

Combine 4-amino pyridine (30 mg, 0.312 mmol) and di-imidazol-1-yl-methanethione (56 mg, 0.312 mmol) in DMF (0.3 mL) and stir for 2 days. Add 2-(2,6-dichloro-phenyl)-3H-benzoimidazole-5-carboxylic acid hydrazide (77 mg, 0.240 mmol) and dilute with DMF (1.5 mL). Heat the reaction to 80° C. for 1 hr. Add EDCI (92 mg, 0.480 mmol) and heat for 1 hr at 80° C. Allow reaction to cool to room temp and dilute the reaction with water. Collect the resulting precipitate by filtration. Purify the solid by reverse-phase HPLC (20-50% ACN/H$_2$O+5 mM NH$_4$OH) to afford the title compound: 1H NMR (400 MHz, DMSO-d6) δ ppm 7.63-7.68 (m, 1H) 7.71 (s, 1H) 7.73 (d, J=2.02 Hz, 1H) 7.76-7.97 (m, 4H) 8.05-8.27 (m, 1H) 8.58 (d, J=6.44 Hz, 2H) 13.34 (br. s., 1H); MS (m/z) 423.0 (M+1).

Example 1-29

{5-[2-(2,6-Dichloro-phenyl)-3H-benzoimidazol-5-yl]-[1,3,4]oxadiazol-2-yl}-pyridin-3-yl-amine

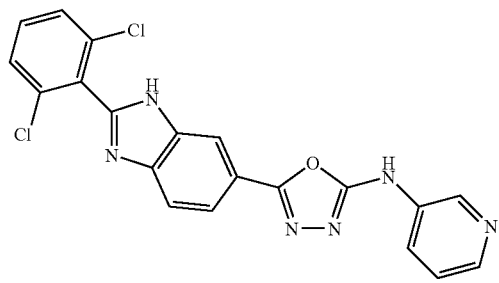

Combine 3-aminopryidine (30 mg, 0.312 mmol) and di-imidazol-1-yl-methanethione (56 mg, 0.312 mmol) in DMF (0.3 mL) and stir for 2 days. Add 2-(2,6-dichloro-phenyl)-3H-benzoimidazole-5-carboxylic acid hydrazide (77 mg, 0.240 mmol) and dilute with DMF (1.5 mL). Heat the reaction to 80° C. for 1 hr. Add EDCI (92 mg, 0.480 mmol) and heat for 1 hr at 80° C. Allow reaction to cool to room temp and dilute the reaction with water. Collect the resulting precipitate by filtration. Purify the solid by reverse-phase HPLC (25-65% ACN/H$_2$O+5 mM NH$_4$OH) to afford the title compound: 1H NMR (400 MHz, DMSO-d6) δ ppm 7.44 (dd, J=8.34, 4.80 Hz, 1H) 7.63-7.67 (m, 1H) 7.70 (s, 1H) 7.72 (d, J=1.77 Hz, 1H) 7.87 (br. s., 2H) 8.13 (ddd, J=8.40, 2.59, 1.39 Hz, 2H) 8.25 (dd, J=4.80, 1.26 Hz, 1H) 8.80 (d, J=2.53 Hz, 1H) 10.98 (s, 1H) 13.30 (br. s., 1H); MS (m/z) 423.1 (M+1).

Example 1-30

Adamantan-1-yl-{5-[2-(2,6-dichloro-phenyl)-3H-benzoimidazol-5-yl]-[1,3,4]oxadiazol-2-yl}-amine

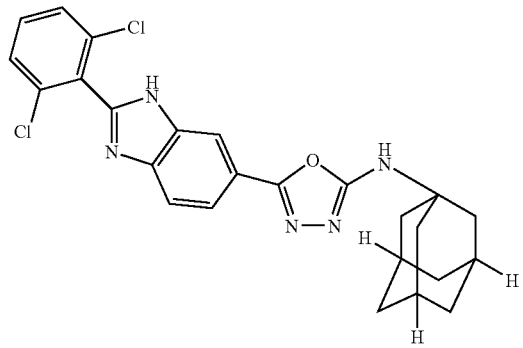

Combine 2-(2,6-dichloro-phenyl)-3H-benzoimidazole-5-carboxylic acid hydrazide (100 mg, 0.310 mmol) and 1-isothiocyanato-adamantane (78 mg, 0.403 mmol) in DMF (2 mL) and heat to 70° C. for 1 hr. Add EDCI (119 mg, 0.620 mmol) and heat the reaction for 1 hr. Allow the reaction to cool to room temp and dilute with water (10 mL). Collect the resulting precipitate by filtration and purify the solid by reverse-phase HPLC (35-65% ACN/H$_2$O+5 mM NH$_4$OH) to afford the title compound as a white solid: 1H NMR (400 MHz, MeOD) δ ppm 1.74-1.82 (m, 6H) 2.12 (s, 6H) 2.15 (br. s., 3H) 7.55-7.63 (m, 3H) 7.76 (br. s., 1H) 7.93 (br. s., 1H) 8.18 (br. s., 1H); MS (m/z) 480.1 (M+1).

Example 1-31

Bicyclo[2.2.1]hept-2-yl-{5-[2-(2,6-dichloro-phenyl)-3H-benzoimidazol-5-yl]-[1,3,4]oxadiazol-2-yl}-amine

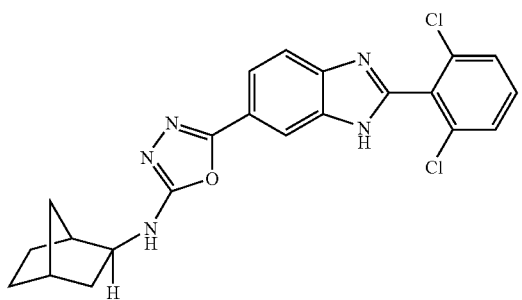

Add di-imidazol-1-yl-methanethione (72 mg, 0.403 mmol) to a solution of bicyclo[2.2.1]hept-2-ylamine (48 uL, 0.403 mmol) in DMF (1 mL) and stir for 3 hr. Add 2-(2,6-dichloro-phenyl)-3H-benzoimidazole-5-carboxylic acid hydrazide (100 mg, 0.310 mmol) and DMF (1 mL) to the reaction. Heat the mixture to 80° C. for 1.5 hr. Add EDCI (119 mg, 0.620 mmol) and heat for 1 hr. Allow the reaction to cool to room temp and dilute with water (15 mL). Collect the resulting precipitate by filtration. Suspend the solid in boiling ACN. Allow the suspension to cool to room temp and then 4° C. Filter to collect the white solid. Suspend the solid in 1 N NaOH (3 mL) and stir for 20 min. Filter and wash the solid with 1 N NaOH, water, and Et$_2$O. Dry the solid in a vac oven to afford the title compound as a white solid: 1H NMR (400 MHz, MeOD) δ ppm 1.17-1.35 (m, 3H) 1.42-1.49 (m, 1H) 1.50-1.64 (m, 3H) 1.87 (ddd, J=12.98, 8.05, 2.08 Hz, 1H) 2.33 (br. s., 1H) 2.40 (d, J=4.04 Hz, 1H) 3.54 (dd, J=7.77, 2.84 Hz, 1H) 7.55-7.63 (m, 3H) 7.77 (d, J=8.34 Hz, 1H) 7.92 (dd, J=8.53, 1.20 Hz, 1H) 8.17 (s, 1H); MS (m/z) 439.9 (M+1).

Example 1-32

2-(2,6-Dichloro-phenyl)-6-(5-morpholin-4-yl-[1,3,4]oxadiazol-2-yl)-1H-benzoimidazole

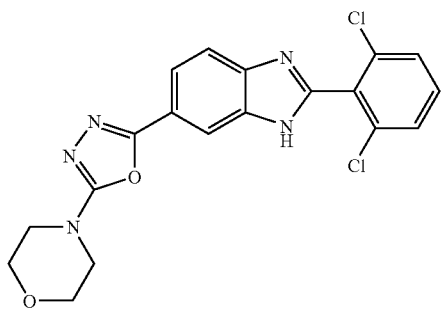

A 20% solution of phosgene in toluene (163 uL, 0.310 mmol) was added dropwise to a solution of morpholine (27 uL, 0.310 mmol) in DCM (3 mL) and EDIPA (108 uL, 0.620 mmol) at 0° C. The reaction was stirred for 25 min before the addition of 2-(2,6-dichloro-phenyl)-3H-benzoimidazole-5-carboxylic acid hydrazide (50 mg, 0.155 mmol) and DMF (1 mL). The ice in the ice bath was allowed to melt, slowly warming the reaction to room temp. The reaction was stirred for 4 days. The reaction was transferred to a microwave vial charged with Burgess reagent (110 mg, 0.465 mmol) and the mixture heated by microwave irradiation to 150° C. for 15 min. The reaction was diluted with EtOAc (50 mL) and extracted with water (10 mL). The organic phase was concentrated to a yellow oil and purified by reverse-phase HPLC (20-45% ACN/H$_2$O+5 mM NH$_4$OH) to afford the title compound: 1H NMR (400 MHz, MeOD) δ ppm 3.66-3.72 (m, 4H) 3.90-3.96 (m, 4H) 7.63-7.72 (m, 3H) 7.87 (d, J=7.96 Hz, 1H) 8.03 (dd, J=8.59, 1.26 Hz, 1H) 8.30 (br. s., 1H); MS (m/z) 416.1 (M+1).

Example 1-33

2-(2,6-Dichloro-phenyl)-6-(5-piperidin-1-yl-[1,3,4]oxadiazol-2-yl)-1H-benzoimidazole

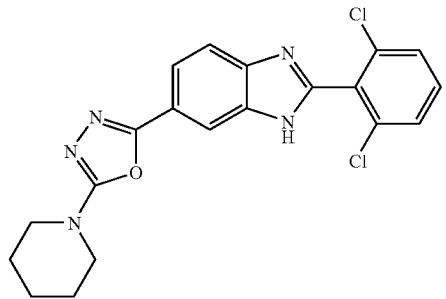

A 20% solution of phosgene in toluene (163 uL, 0.310 mmol) was added dropwise to a solution of piperidine (31 uL, 0.310 mmol) in DCM (2 mL) and EDIPA (108 uL, 0.620 mmol) at 0° C. under N$_2$. The reaction was stirred for 40 min before the addition of 2-(2,6-dichloro-phenyl)-3H-benzoimidazole-5-carboxylic acid hydrazide (50 mg, 0.155 mmol) and DMF (1 mL). The ice in the ice bath was allowed to melt, slowly warming the reaction to room temp. The reaction was stirred for 4 days. The reaction was diluted with EtOAc (60 mL) and extracted with water (10 mL). The organic phase was concentrated to a yellow oil. The yellow oil was added to a microwave vial charged with THF (1.5 mL) and Burgess reagent. The mixture was heated by microwave irradiation to 150° C. for 15 min. The reaction was concentrated, and the concentrate diluted with water. The resulting precipitate was collected by filtration and purified by reverse-phase HPLC (25-60% ACN/H₂O+5 mM NH₄OH) to afford the title compound: 1H NMR (400 MHz, MeOD) δ ppm 1.74 (br. s., 6H) 3.57-3.64 (m, 4H) 7.55-7.63 (m, 3H) 7.78 (d, J=8.59 Hz, 1H) 7.94 (dd, J=8.53, 1.33 Hz, 1H) 8.20 (br. s., 1H); MS (m/z) 414.1 (M+1).

Example 1-34

2-(2,6-Dichloro-phenyl)-6-(5-pyrrolidin-1-yl-[1,3,4] oxadiazol-2-yl)-1H-benzoimidazole

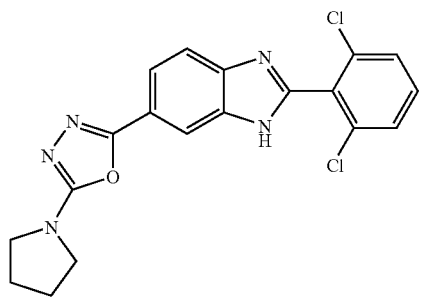

A 20% solution of phosgene in toluene (163 uL, 0.310 mmol) was added dropwise to a solution of pyrrolidine (51 uL, 0.620 mmol) in THF (2 mL) and EDIPA (216 uL, 1.24 mmol) at 0° C. under N₂. The reaction was stirred for 20 min before the addition of 2-(2,6-dichloro-phenyl)-3H-benzoimidazole-5-carboxylic acid hydrazide (100 mg, 0.310 mmol) and NMP (1 mL). The ice bath was removed after 2 hr and the reaction allowed to stir overnight. The reaction was heated to 60° C. for 1.5 hr before being concentrated. The concentrate was added to a microwave vial charged with Burgess reagent (220 mg, 0.930 mmol) and the mixture heated to 150° C. for 15 min by microwave irradiation. The reaction was partitioned between EtOAc and H₂O. The organic phase was concentrated and purified by reverse phase HPLC (25-50% ACN/H₂O+5 mM NH₄OH) to afford the title compound: 1H NMR (400 MHz, MeOD) δ ppm 2.05-2.14 (m, 4H) 3.58-3.67 (m, 4H) 7.55-7.64 (m, 3H) 7.79 (br. s., 1H) 7.94 (d, J=8.34 Hz, 1H) 8.19 (br. s., 1H); MS m/z=400.1 (M+1).

Example 1-35

{5-[2-(2,6-Dichloro-phenyl)-3H-benzoimidazol-5-yl]-[1,3,4]oxadiazol-2-yl}-m-tolyl-amine

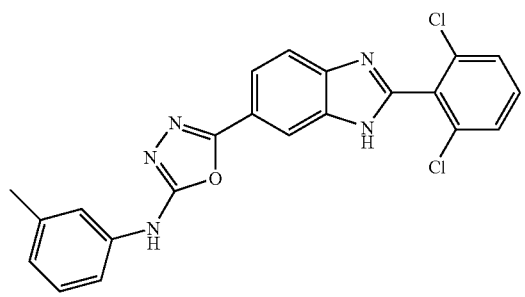

To a solution of 2-(2,6-dichloro-phenyl)-3H-benzoimidazole-5-carboxylic acid hydrazide (150 mg, 0.466 mmol) in DMF (3 mL) add m-tolyl isothiocyanate (69 uL, 0.512 mmol) and stir for 3.5 hr. Add EDCI (179 mg, 0.932 mmol) and heat to 80° C. for 1 hr. Upon cooling to room temp dilute the reaction with EtOAc (75 mL) and extract with water (15 mL). Evaporate the organic phase and recrystallize from toluene/EtOAc. Suspend the solid in 1 N NaOH. Collect the solid wash with water and Et₂O to afford the title compound as a white solid: 1H NMR (400 MHz, MeOD) δ ppm 2.38 (s, 3H) 6.90 (d, J=7.58 Hz, 1H) 7.26 (t, J=7.77 Hz, 1H) 7.37 (d, J=1.77 Hz, 1H) 7.43 (s, 1H) 7.56-7.65 (m, 3H) 7.82 (d, J=8.59 Hz, 1H) 8.01 (dd, J=8.53, 1.33 Hz, 1H) 8.27 (s, 1H); MS m/z=436.1 (M+1).

Example 1-36

{5-[2-(2,6-Dichloro-phenyl)-3H-benzoimidazol-5-yl]-[1,3,4]oxadiazol-2-yl}-phenyl-amine

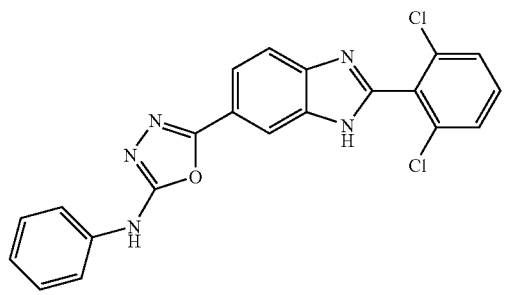

To a solution of 2-(2,6-dichloro-phenyl)-3H-benzoimidazole-5-carboxylic acid hydrazide (150 mg, 0.466 mmol) in DMF (3 mL) add phenyl isothiocyanate (97 uL, 0.512 mmol) and stir for 3.5 hr. Add EDCI (179 mg, 0.932 mmol) and heat to 80° C. for 1 hr. Upon cooling to room temp dilute the reaction with EtOAc (75 mL) and extract with water (15 mL). Evaporate the organic phase and suspend the resulting residue in 1 N NaOH (5 mL). Collect the solid and wash with water. Take the solid up in boiling toluene/EtOAc. Allow to cool. Collect the solid, wash with Et₂O, and dry in a vac-oven to afford the title compound as an off-white solid: 1H NMR (400 MHz, DMSO-d6) δ ppm 7.03 (t, J=7.39 Hz, 1H) 7.39 (t, J=7.96 Hz, 2H) 7.63-7.69 (m, 3H) 7.71 (d, J=1.26 Hz, 1H) 7.73 (t, J=1.89 Hz, 1H) 7.77 (tautomer A, d, J=8.59 Hz, 1H) 7.83 (tautomer B. dd, J=8.46, 1.52 Hz, 1H) 7.91 (dd, J=8.46, 1.52 Hz, 1H) 8.05 (tautomer B. d, J=1.01 Hz, 1H) 8.17 (tautomer A, s, 1H) 10.68 (s, 1H) 13.30 (d, J=4.17 Hz, 1H); MS (m/z)=422.0 (M+1).

Example 1-37

{5-[2-(2,6-Dichloro-phenyl)-3H-benzoimidazol-5-yl]-[1,3,4]oxadiazol-2-yl}-(3-methoxy-phenyl)-amine

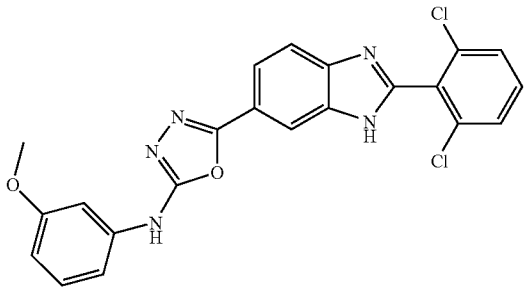

To a solution of 2-(2,6-dichloro-phenyl)-3H-benzoimidazole-5-carboxylic acid hydrazide (150 mg, 0.466 mmol) in DMF (3 mL) add 3-methoxy phenyl isothiocyanate (69 uL, 0.512 mmol) and stir for 1.5 hr. Add EDCI (179 mg, 0.932 mmol) and heat to 80° C. for 50 min. Upon cooling to room temp, dilute the reaction with EtOAc (75 mL) and extract with water (15 mL). Evaporate the organic phase and suspend the solid in 1 N NaOH. Collect the solid wash with water and Et$_2$O, Suspend the solid in boiling toluene/EtOAc. Cool the suspension to 4° C. and filter. Wash the solid with Et$_2$O. Again suspend the solid in 1 N NaOH and stir for 1 hr. Collect the solid and wash with water and Et$_2$O. Dry to afford the title compound: 1H NMR (400 MHz, DMSO-d6) δ ppm 3.78 (s, 3H) 6.61 (dd, J=8.15, 1.83 Hz, 1H) 7.14-7.19 (m, 1H) 7.28 (t, J=8.15 Hz, 1H) 7.34 (t, J=2.15 Hz, 1H) 7.64 (dd, J=9.35, 6.69 Hz, 1H) 7.70 (s, 1H) 7.84 (br. s., 2H) 7.72 (d, J=1.89 Hz, 1H) 8.11 (br. s., 1H) 10.67 (br. s., 1H) 13.29 (br. s., 1H); MS m/z=452.1 (M+1).

Example 1-38

{5-[2-(2,6-Dichloro-phenyl)-3H-benzoimidazol-5-yl]-[1,3,4]oxadiazol-2-yl}-(6-methyl-pyridin-3-yl)-amine

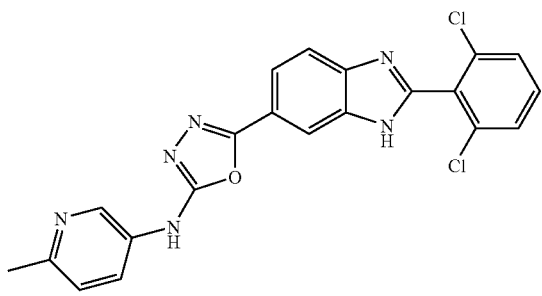

Combine 3-amino-6-methyl-pyridine (66 mg, 0.606 mmol) and di-imidazol-1-yl-methanethione (108 mg, 0.606 mmol) in DMF (1.5 mL) and stir for 4 hr. Add 2-(2,6-dichloro-phenyl)-3H-benzoimidazole-5-carboxylic acid hydrazide (150 mg, 0.466 mmol) and DMF (1 mL). Stir for 3 days. Add EDCI (179 mg, 0.932 mmol) and heat to 80° C. for 45 min. Upon cooling, dilute the reaction with EtOAc (50 mL) and extract with water (10 mL) and 1 N NaOH (10 mL). Combine the aqueous layers and allow to stand overnight. Filter the combined aqueous layers and wash the collected solid with Et$_2$O. Suspend the solid in boiling toluene/EtOAc. Allow the suspension to cool to 4° C. and collect the solid. Wash with Et$_2$O. Purify the solid by reverse phase HPLC (20-65% ACN/H$_2$O+5 mM NH$_4$OH) to afford the title compound: 1H NMR (400 MHz, DMSO-d6) δ ppm 2.46 (s, 3H) 7.33 (d, J=8.34 Hz, 1H) 7.64-7.68 (m, 1H) 7.71 (s, 1H) 7.73 (d, J=2.02 Hz, 1H) 7.86 (br. s., 2H) 8.04 (dd, J=8.40, 2.46 Hz, 1H) 8.13 (br. s., 1H) 8.70 (d, J=2.53 Hz, 1H) 10.88 (br. s., 1H); MS m/z=437.0 (M+1).

Example 1-39

(6-Chloro-pyridin-3-yl)-{5-[2-(2,6-dichloro-phenyl)-3H-benzoimidazol-5-yl]-[1,3,4]oxadiazol-2-yl}-amine

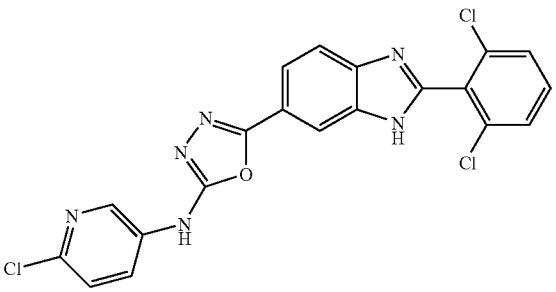

Combine 3-amino-6-chloro-pyridine (78 mg, 0.606 mmol) and di-imidazol-1-yl-methanethione (108 mg, 0.606 mmol) in DMF (1.5 mL) and stir for 4 hr. Add 2-(2,6-dichloro-phenyl)-3H-benzoimidazole-5-carboxylic acid hydrazide (150 mg, 0.466 mmol) and DMF (1 mL). Stir for 3 days. Add EDCI (179 mg, 0.932 mmol) and heat to 80° C. for 45 min. Upon cooling, dilute the reaction with EtOAc (50 mL) and extract with water (10 mL) and 1 N NaOH (10 mL). Combine the aqueous layers and allow to stand overnight. Evaporate the organic phase. Filter the combined aqueous layers and wash the collected solid with Et$_2$O. Combine the solid with the residue from the organic phase and purify the material by reverse phase HPLC (20-65% ACN/H$_2$O+5 mM NH$_4$OH) to afford the title compound: 1H NMR (400 MHz, DMSO-d6) δ ppm 7.56 (d, J=8.72 Hz, 1H) 7.63-7.68 (m, 1H) 7.70 (s, 1H) 7.72 (d, J=2.02 Hz, 1H) 7.86 (br. s., 2H) 8.13 (br. s., 1H) 8.16 (dd, J=8.78, 2.97 Hz, 1H) 8.64 (d, J=2.91 Hz, 1H) 11.16 (s, 1H) 13.31 (br. s., 1H); MS m/z=458.9 (M+1).

Example 1-40

{5-[2-(2,6-Dichloro-phenyl)-3H-benzoimidazol-5-yl]-[1,3,4]oxadiazol-2-yl}-(6-methoxy-pyridin-3-yl)-amine

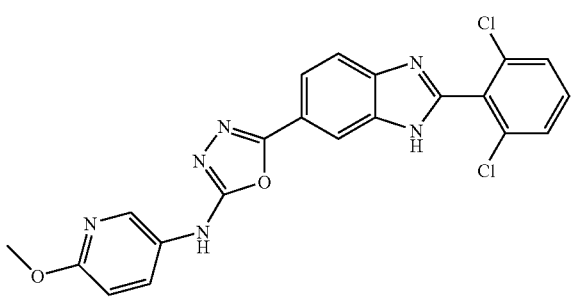

Combine 3-amino-6-methoxy-pyridine (64 uL, 0.606 mmol) and di-imidazol-1-yl-methanethione (108 mg, 0.606 mmol) in DMF (1.5 mL) and stir for 3 hr. Add 2-(2,6-dichloro-phenyl)-3H-benzoimidazole-5-carboxylic acid hydrazide (150 mg, 0.466 mmol) and DMF (1 mL). Heat to 80° C. for 1 hr. Add EDCI (179 mg, 0.932 mmol) and heat to 80° C. for 1 hr. Upon cooling, dilute the reaction with EtOAc (50 mL) and extract with water (10 mL). Dry the organic phase over $Na_2SO_4$ and concentrate. Triturate the concentrate with hot EtOAc/toluene to obtain a white solid. Suspend the solid in saturated $NaHCO_3$ and stir vigorously. Collect the solid and purify by silica gel chromatography (10-100% EtOAc/HEP, 0-50% MeOH/DCM) to afford the title compound as a white solid: 1H NMR (400 MHz, DMSO-d6) δ ppm 3.84 (s, 3H) 6.89 (d, J=8.84 Hz, 1H) 7.62-7.67 (m, 1H) 7.70 (s, 1H) 7.72 (d, J=1.64 Hz, 1H) 7.76 (tautomer, d, J=8.46 Hz, 1H) 7.81 (tautomer, dd, J=8.46, 1.26 Hz, 1H) 7.85-7.92 (mixture of tautomers, m, 1H) 7.96-8.01 (m, 1H) 8.03 (tautomer, s, 1H) 8.16 (tautomer, s, 1H) 8.44 (s, 1H) 10.63 (s, 1H) 13.28 (s, 1H); MS m/z=453.0 (M+1).

Example 1-41

(3-Chloro-phenyl)-{5-[2-(2,6-dichloro-phenyl)-3H-benzoimidazol-5-yl]-[1,3,4]oxadiazol-2-yl}-amine

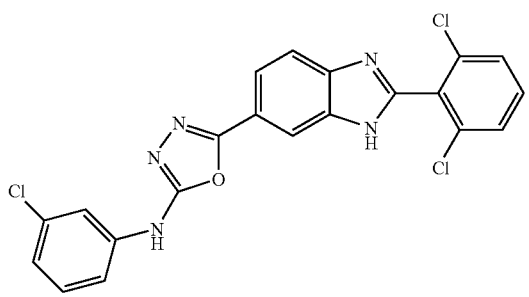

To a solution of 2-(2,6-dichloro-phenyl)-3H-benzoimidazole-5-carboxylic acid hydrazide (150 mg, 0.466 mmol) in DMF (3 mL) add 3-chloro phenyl isothiocyanate (69 uL, 0.512 mmol) and stir for 1.75 hr. Add EDCI (179 mg, 0.932 mmol) and heat to 80° C. for 30 min. Allow to stir at room temp overnight. Dilute the reaction with EtOAc (50 mL) and extract with water (10 mL) and 1 N NaOH (10 mL). Dry the organic phase over $Na_2SO_4$ and evaporate the solvent. Combine the aqueous phases, chill to 4° C., and filter. Combine the solids and suspend them in boiling toluene/EtOAc. Cool the suspension to 4° C. and filter. Wash the solid with $Et_2O$. Dry to afford the title compound as a white solid: 1H NMR (400 MHz, DMSO-d6) δ ppm 7.07 (ddd, J=7.96, 2.02, 0.76 Hz, 1H) 7.40 (t, J=8.15 Hz, 1H) 7.50-7.55 (m, 1H) 7.62-7.67 (m, 1H) 7.70 (s, 1H) 7.72 (d, J=2.02 Hz, 1H) 7.75-7.91 (m, 3H) 8.11 (br. s., 1H) 10.99 (br. s., 1H) 13.28 (br. s., 1H); MS m/z=457.9 (M+1).

Example 1-42

{5-[2-(2,6-Dichloro-phenyl)-3H-benzoimidazol-5-yl]-[1,3,4]oxadiazol-2-yl}-(2-methyl-pyridin-4-yl)-amine

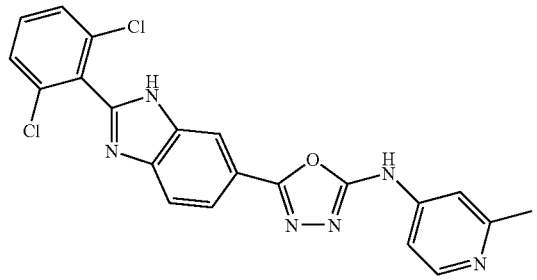

Combine 4-amino-3-methyl-pyridine (66 mg, 0.606 mmol) and di-imidazol-1-yl-methanethione (108 mg, 0.606 mmol) in DMF (1.5 mL) and stir overnight. Add 2-(2,6-dichloro-phenyl)-3H-benzoimidazole-5-carboxylic acid hydrazide (150 mg, 0.466 mmol) and DMF (1.5 mL). Heat to 80° C. for 1 hr. Add EDCI (179 mg, 0.932 mmol) and heat to 80° C. for 1 hr. Upon cooling, dilute the reaction with EtOAc (75 mL) and extract with water (15 mL). Dry the organic phase over $Na_2SO_4$ and concentrate. Take the concentrate up in boiling toluene/EtOAc and cool to 4° C. Collect the resulting precipitate and purify by reverse-phase HPLC (20-45% $ACN/H_2O+5$ mM $NH_4OH$) to afford the title compound as a light yellow solid: 1H NMR (400 MHz, DMSO-d6, 100° C.) δ ppm 2.46 (s, 3H) 7.36 (dd, J=5.75, 2.14 Hz, 1H) 7.42 (s, 1H) 7.59-7.67 (m, 3H) 7.81 (d, J=8.68 Hz, 1H) 7.87 (dd, J=8.44, 1.47 Hz, 1H) 8.16 (s, 1H) 8.27 (d, J=5.69 Hz, 1H); MS m/z=437.0 (M+1).

Example 1-43

(2-Chloro-pyridin-4-yl)-{5-[2-(2,6-dichloro-phenyl)-3H-benzoimidazol-5-yl]-[1,3,4]oxadiazol-2-yl}-amine

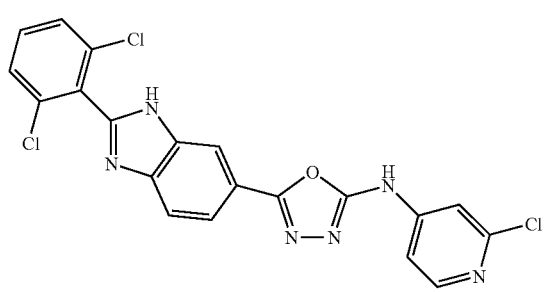

Combine 4-amino-3-chloro-pyridine (78 mg, 0.606 mmol) and di-imidazol-1-yl-methanethione (108 mg, 0.606 mmol) in DMF (1.5 mL) and stir overnight. Add 2-(2,6-dichlorophenyl)-3H-benzoimidazole-5-carboxylic acid hydrazide (150 mg, 0.466 mmol) and DMF (1.5 mL). Heat to 80° C. for 1 hr. Add EDCI (179 mg, 0.932 mmol) and heat to 80° C. for 1 hr. Upon cooling, dilute the reaction with EtOAc (75 mL) and extract with water (15 mL). Dry the organic phase over $Na_2SO_4$ and concentrate. Purify the concentrate by reverse-phase HPLC (25-40% ACN/$H_2O$+5 mM $NH_4OH$) to afford the title compound as a yellow solid: 1H NMR (400 MHz, DMSO-d6) δ ppm 7.51 (d, J=4.17 Hz, 1H) 7.62-7.68 (m, 1H) 7.70 (s, 1H) 7.73 (dd, J=7.39, 1.96 Hz, 2H) 7.75-7.87 (m, 1H) 7.87-7.95 (m, 1H) 8.07 (tautomer, br. s., 1H) 8.19 (tautomer, br. s., 1H) 8.29 (d, J=5.68 Hz, 1H) 11.58 (br. s., 1H) 13.32 (br. s., 1H); MS m/z=456.9 (M+1).

Example 1-44

{5-[2-(2,6-Dichloro-phenyl)-3H-benzoimidazol-5-yl]-[1,3,4]oxadiazol-2-yl}-(6-trifluoromethyl-pyridin-3-yl)-amine

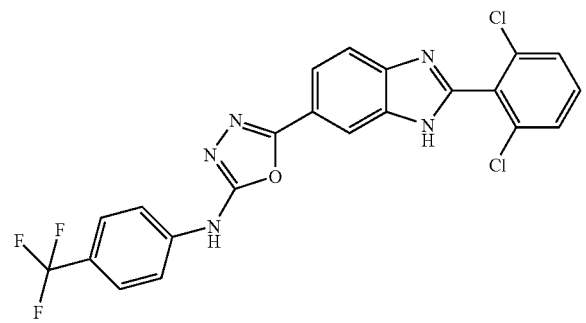

Combine 3-amino-6-trifluoromethyl-pyridine (98 mg, 0.606 mmol) and di-imidazol-1-yl-methanethione (108 mg, 0.606 mmol) in DMF (1.5 mL) and stir overnight. Add 2-(2,6-dichloro-phenyl)-3H-benzoimidazole-5-carboxylic acid hydrazide (150 mg, 0.466 mmol) and DMF (1 mL). Stir for 6.5 hr. Add EDCI (179 mg, 0.932 mmol) and heat to 80° C. for 1 hr. Upon cooling, dilute the reaction with EtOAc (75 mL) and extract with water (15 mL). Dry the organic phase over $Na_2SO_4$ and evaporate the solvent. Purify the residue by silica gel chromatography (3-6% MeOH/DCM) to afford the title compound as an off white solid: 1H NMR (400 MHz, DMSO-d6) δ ppm 7.62-7.68 (m, 1H) 7.71 (d, J=1.01 Hz, 1H) 7.73 (t, J=1.77 Hz, 1H) 7.78 (tautomer, d, J=8.59 Hz, 1H) 7.82-7.87 (tautomer, m, 1H) 7.90-7.94 (m, 1H) 7.96 (d, J=8.72 Hz, 1H) 8.08 (tautomer, d, J=0.88 Hz, 1H) 8.21 (tautomer, s, 1H) 8.38 (d, J=8.59 Hz, 1H) 8.90 (d, J=2.27 Hz, 1H) 11.51 (s, 1H) 13.32 (d, J=2.91 Hz, 1H); MS m/z=490.9 (M+1).

Example 1-45

3,5-Dimethyl-4-{6-[5-(4-trifluoromethyl-phenylamino)-[1,3,4]oxadiazol-2-yl]-1H-benzoimidazol-2-yl}-phenol A. 4-[5-(4-Trifluoromethyl-phenylamino)-[1,3,4]oxadiazol-2-yl]-benzene-1,2-diamine To a 30 mL vial was added 0.5 g (3.01 mmol) of 3,4-diaminobenzhydrazide, 25 mL of DCM, and 0.61 g (3.01 mmol) of 4-trifluoromethyl-phenyl isothiocyanate. Allowed to stir at r.t. for 72 h. The pink suspension was concentrated in vacuo and used directly in the next reaction. MS (m/z) 370.0 M (+1), $t_R$=1.10, Meth 10. To 20 mL scint vial was added 1.03 g (2.61 mmol) of the crude, 10 mL of DMF, and 0.55 g (2.87 mmol) of EDCI. Allowed to stir at 60° C., for 3 h. Added water, and filtered off solid. Used directly in next reaction. MS (m/z) 336.0 M (+1), $t_R$=1.24, Meth 10

B. 3,5-Dimethyl-4-{6-[5-(4-trifluoromethyl-phenylamino)-[1,3,4]oxadiazol-2-yl]-1H-benzoimidazol-2-yl}-phenol The title compound was prepared analogous to step A of Intermediate 2. Except, to reaction mixture was added EtOAc, and water, and solid filtered which gave the title compound. 1H NMR (400 MHz, DMSO-d6) δ ppm 2.04 (s, 6H) 6.59 (s, 2H) 7.73-7.84 (m, 5H) 8.05 (br. s., 1H) 9.62 (s, 1H) 11.15 (s, 1H) 12.85 (br. s., 1H). MS (m/z) 466.0 M (+1), $t_R$=1.37, Meth 10

Example 1-46

(2-tert-Butyl-pyridin-4-yl)-{5-[2-(2,6-dichloro-phenyl)-3H-benzoimidazol-5-yl]-[1,3,4]oxadiazol-2-yl}-amine

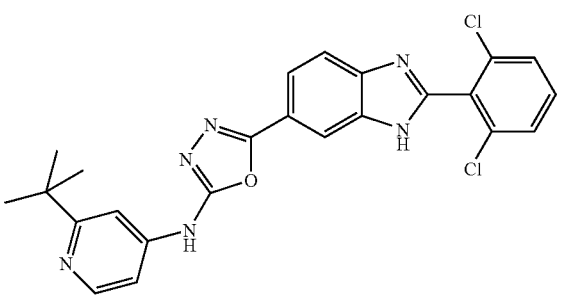

Combine 4-amino-3-tert-butyl-pyridine (91 mg, 0.606 mmol) and di-imidazol-1-yl-methanethione (108 mg, 0.606 mmol) in DMF (1.5 mL) and stir overnight. Add 2-(2,6-dichloro-phenyl)-3H-benzoimidazole-5-carboxylic acid hydrazide (150 mg, 0.466 mmol) and DMF (1 mL). Stir for 6.5 hr. Add EDCI (179 mg, 0.932 mmol) and heat to 80° C. for 1 hr. Upon cooling, dilute the reaction with EtOAc (75 mL) and extract with water (10 mL). Dry the organic phase over $Na_2SO_4$ and evaporate the solvent. Purify the residue by silica gel chromatography (3-6% MeOH/DCM) followed by reverse-phase HPLC (20-60% ACN/$H_2O$+5 mM $NH_4OH$) to afford the title compound as a light yellow solid: 1H NMR (400 MHz, DMSO-d6) δ ppm 1.33 (s, 9H) 7.41 (dd, J=5.49, 1.33 Hz, 1H) 7.63-7.73 (m, 4H) 7.78 (tautomer, d, J=8.46 Hz, 1H) 7.81-7.86 (tautomer, m, 1H) 7.91 (m, 1H) 8.06 (tautomer, d, J=0.88 Hz, 1H) 8.19 (tautomer, s, 1H) 8.41 (d, J=5.56 Hz, 1H) 11.13 (s, 1H) 13.31 (d, J=4.29 Hz, 1H); MS m/z=479.8 (M+1).

Example 1-47

{5-[2-(2,6-Dichloro-phenyl)-3H-benzoimidazol-5-yl]-[1,3,4]oxadiazol-2-yl}-(5-fluoro-pyridin-2-yl)-amine

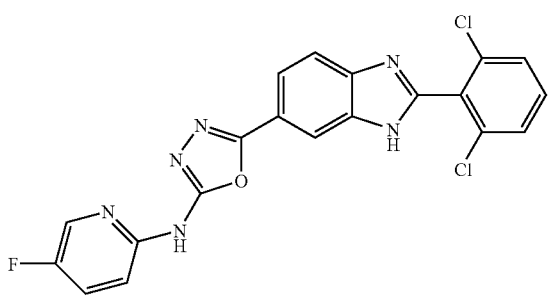

Dissolve 2-amino-5-fluoro-pyridine (68 mg, 0.606 mmol) in a biphasic solution of $CHCl_3$ (15 mL) and saturated $NaHCO_3$ (15 mL). Add thiophosgene (46 uL, 0.606 mmol) to the organic phase and stir the reaction vigorously for 1 hr. Add 2-(2,6-dichloro-phenyl)-3H-benzoimidazole-5-carboxylic acid hydrazide (146 mg, 0.455 mmol) and stir for 7 hr. Add additional 2-amino-5-fluoro-pyridine (68 mg, 0.606 mmol) and stir overnight. Filter the reaction and wash the collected solid with DCM. Concentrate the organic phase of the filtrate and combine with the solid. Add DMF (3 mL) and EDCI (174 mg, 0.910 mmol) and heat the reaction to 80° C. for 1 hr. Allow the reaction to cool to room temp. Dilute with EtOAc (75 mL) and extract with water (15 mL). Dry the organic phase over $Na_2SO_4$ and concentrate. Purify the concentrate by silica gel chromatography (3-6% MeOH/DCM) followed by reversed phase HPLC (20-60% ACN/$H_2O$+5 mM $NH_4OH$) to afford the title compound as a white solid: 1H NMR (400 MHz, DMSO-d6) δ ppm 7.62-7.68 (m, 1H) 7.70 (s, 1H) 7.72 (d, J=1.77 Hz, 1H) 7.74-7.94 (m, 3H) 8.01 (dd, J=9.22, 3.66 Hz, 1H) 8.05 (tautomer, s, 1H) 8.19 (tautomer, s, 1H) 8.35 (d, J=3.03 Hz, 1H) 11.37 (br. s., 1H) 13.29 (s, 1H); MS m/z=441.7 (M+1).

Example 1-48

{5-[2-(2,6-Dichloro-phenyl)-3H-benzoimidazol-5-yl]-[1,3,4]oxadiazol-2-yl}-(4-methyl-pyridin-3-yl)-amine

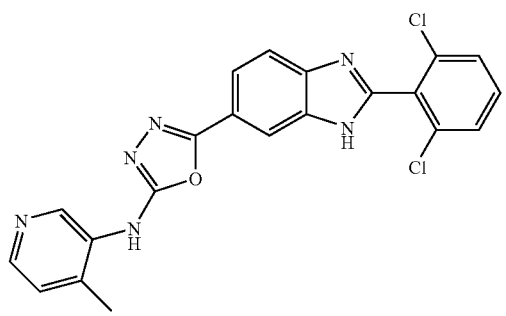

Combine 3-amino-4-methyl-pyridine (66 mg, 0.606 mmol) and di-imidazol-1-yl-methanethione (108 mg, 0.606 mmol) in DMF (1.5 mL) and stir for 7.5 hr. Add 2-(2,6-dichloro-phenyl)-3H-benzoimidazole-5-carboxylic acid hydrazide (150 mg, 0.466 mmol) and DMF (1 mL). Stir for 3 days. Add EDCI (179 mg, 0.932 mmol) and heat to 80° C. for 1 hr. Upon cooling, dilute the reaction with EtOAc (75 mL) and extract with water (15 mL). Dry the organic phase over $Na_2SO_4$ and evaporate the solvent. Purify the residue by reverse phase HPLC (30-45% ACN/$H_2O$+5 mM $NH_4OH$) to afford the title compound as a light yellow solid: 1H NMR (400 MHz, DMSO-d6) δ ppm 2.35 (s, 3H) 7.30 (d, J=4.80 Hz, 1H) 7.62-7.68 (m, 1H) 7.72 (d, J=2.02 Hz, 1H) 7.70 (s, 1H) 7.83 (br. s., 2H) 7.98-8.19 (m, 1H) 8.24 (d, J=4.80 Hz, 1H) 8.98 (s, 1H) 9.95 (br. s., 1H) 13.28 (br. s., 1H); MS m/z=436.9 (M+1).

Example 1-49

{5-[2-(2,6-Dichloro-phenyl)-3H-benzoimidazol-5-yl]-[1,3,4]oxadiazol-2-yl}-(2-methoxy-pyridin-3-yl)-amine

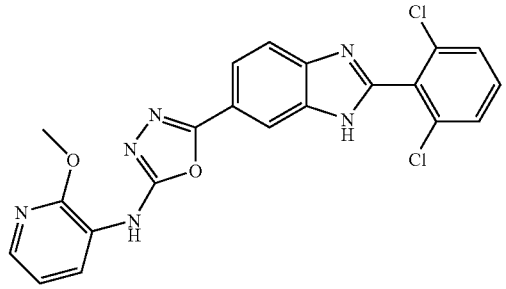

Combine 2-methoxy-3-amino-pyridine (75 mg, 0.606 mmol) and di-imidazol-1-yl-methanethione (108 mg, 0.606 mmol) in DMF (1.5 mL) and stir for 7.5 hr. Add 2-(2,6-dichloro-phenyl)-3H-benzoimidazole-5-carboxylic acid hydrazide (150 mg, 0.466 mmol) and DMF (1 mL). Stir for 3 days. Add EDCI (179 mg, 0.932 mmol) and heat to 80° C. for 1 hr. Upon cooling, dilute the reaction with EtOAc (75 mL) and extract with water (15 mL). Dry the organic phase over $Na_2SO_4$ and evaporate the solvent. Purify the residue by reverse phase HPLC (35-50% ACN/H₂O+5 mM NH₄OH) to afford the title compound as a light tan solid: 1H NMR (400 MHz, DMSO-d6) δ ppm 3.98 (s, 3H) 7.07 (dd, J=7.77, 4.99 Hz, 1H) 7.62-7.68 (m, 1H) 7.72 (d, J=1.89 Hz, 1H) 7.70 (s, 1H) 7.74-7.92 (m, 3H) 8.00-8.23 (m, 1H) 8.42 (dd, J=7.83, 1.64 Hz, 1H) 10.12 (br. s., 1H) 13.30 (br. s., 1H); MS m/z=452.9 (M+1).

Example 1-50

{5-[2-(2,6-Dichloro-phenyl)-3H-benzoimidazol-5-yl]-[1,3,4]oxadiazol-2-yl}-(5-trifluoromethyl-pyridin-2-yl)-amine

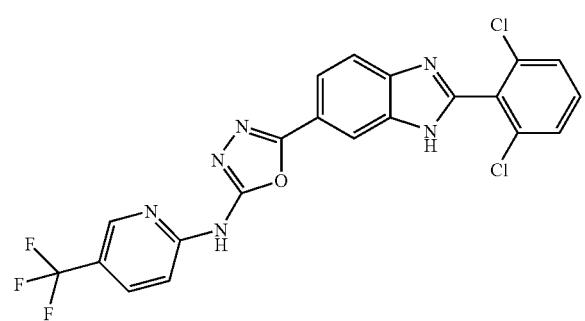

Dissolve 2-amino-5-trifluoromethyl-pyridine (164 mg, 1.01 mmol) in a biphasic solution of CHCl₃ (25 mL) and saturated NaHCO₃ (25 mL). Add thiophosgene (78 uL, 1.01 mmol) to the organic phase and stir the reaction vigorously for 2.5 hr. Separate the phases and extract the aqueous phase with CHCl₃ (25 mL). Concentrate the combined organics and take the concentrate up in DMF (3 mL). Add 2-(2,6-dichloro-phenyl)-3H-benzoimidazole-5-carboxylic acid hydrazide (250 mg, 0.778 mmol) and stir overnight. Add EDCI (298 mg, 1.56 mmol) and heat to 80° C. for 4 hr. Upon cooling to room temp dilute the reaction with EtOAc (75 mL) and extract with water (15 mL). Dry the organic phase over Na₂SO₄ and concentrate. Purify the concentrate by reverse phase HPLC (35-50% ACN/H₂O+5 mM NH₄OH) to afford the title compound as a cream colored solid: 1H NMR (400 MHz, DMSO-d6) δ ppm 7.63-7.68 (m, 1H) 7.70 (s, 1H) 7.72 (d, J=1.77 Hz, 1H) 7.76-7.87 (m, 1H) 7.88-7.94 (m, 1H) 8.04-8.30 (m, 3H) 8.72 (br. s., 1H) 11.87 (br. s., 1H) 13.31 (br. s., 1H); MS m/z=491.8 (M+1).

Example 1-51

3-{5-[2-(2,6-Dichloro-phenyl)-3H-benzoimidazol-5-yl]-[1,3,4]oxadiazol-2-ylamino}-benzonitrile

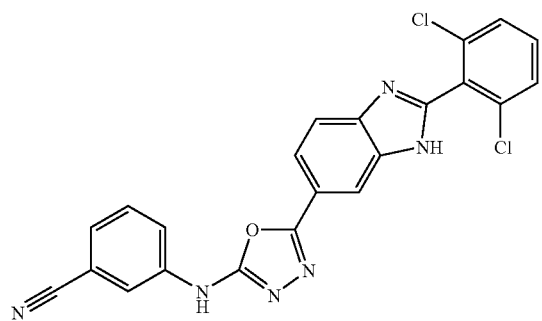

A. 3-[5-(3,4-Diamino-phenyl)-[1,3,4]oxadiazol-2-ylamino]-benzonitrile

The title compound was prepared analogous to step A of Example 1-45. MS (m/z) 293.0 M (+1), $t_R$=1.03, Meth 10

B. 3-{5-[2-(2,6-Dichloro-phenyl)-3H-benzoimidazol-5-yl]-[1,3,4]oxadiazol-2-ylamino}-benzonitrile The title compound was prepared analogous to step B of Intermediate 1. 1H NMR (400 MHz, DMSO-d6) δ ppm 7.61 (d, J=7.58 Hz, 1H) 7.70-7.79 (m, 2H) 7.81-7.85 (m, 2H) 7.89 (d, J=8.34 Hz, 0.5H) 7.94-8.05 (m, 2.5H) 8.16-8.24 (m, 1.5H) 8.31 (br. s., 0.5H) 11.28 (br. s., 1H) 13.43 (br. s., 1H). MS (m/z) 446.9 M (+1), $t_R$=1.28, Meth 10

Example 1-52

3,5-Dimethyl-4-{6-[5-(3-trifluoromethyl-phenylamino)-[1,3,4]oxadiazol-2-yl]-1H-benzoimidazol-2-yl}-phenol

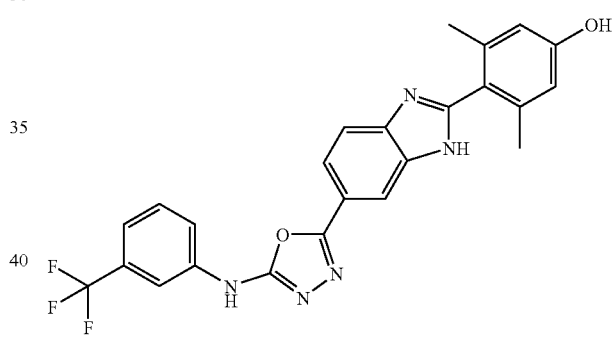

A. 4-[5-(3-Trifluoromethyl-phenylamino)-[1,3,4]oxadiazol-2-yl]-benzene-1,2-diamine The title compound was prepared analogous to step A of Example 1-45. MS (m/z) 336.0 M (+1), $t_R$=1.24, Meth 10

B. 3,5-Dimethyl-4-{6-[5-(3-trifluoromethyl-phenylamino)-[1,3,4]oxadiazol-2-yl]-1H-benzoimidazol-2-yl}-phenol The title compound was prepared analogous to step B of Intermediate 1. 1H NMR (400 MHz, DMSO-d6) δ ppm 1.98 (d, J=2.91 Hz, 6H) 6.53 (s, 2H) 7.31 (d, J=7.58 Hz, 1H) 7.53-7.62 (m, 1.5H) 7.67-7.72 (m, 0.5H) 7.77 (t, J=7.58 Hz, 2H) 7.91 (s, 0.5H) 8.05 (d, J=3.79 Hz, 1.5H) 9.56 (d, J=5.05 Hz, 1H) 11.02 (s, 1H) 12.74 (d, J=8.34 Hz, 1H). MS (m/z) 465.7 M (+1), $t_R$=1.35, Meth 10

Example 1-53

{5-[2-(2,6-Dichloro-phenyl)-3H-benzoimidazol-5-yl]-[1,3,4]oxadiazol-2-yl}-(6-morpholin-4-yl-pyridin-3-yl)-amine

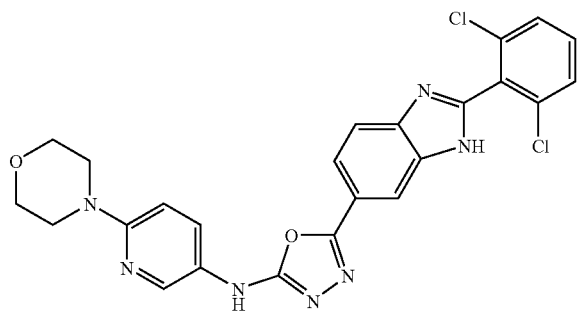

A. 4-[5-(6-Morpholin-4-yl-pyridin-3-ylamino)-[1,3,4]oxadiazol-2-yl]-benzene-1,2-diamine The title compound was prepared analogous to step A of Example 1-45. MS (m/z) 353.9 M (+1), $t_R$=0.77, Meth 10

B. {5-[2-(2,6-Dichloro-phenyl)-3H-benzoimidazol-5-yl]-[1,3,4]oxadiazol-2-yl}-(6-morpholin-4-yl-pyridin-3-yl)-amine The title compound was prepared analogous to step B of Intermediate 1. 1H NMR (400 MHz, DMSO-d6) δ ppm 3.34-3.39 (m, 4H) 3.67-3.74 (m, 4H) 6.92 (d, J=9.09 Hz, 1H) 7.61-7.66 (m, 1H) 7.68-7.80 (m, 3H) 7.83-7.91 (m, 2H) 8.01 (br. s., 0.5H) 8.13 (s, 0.5H) 8.39 (d, J=2.65 Hz, 1H) 10.43 (s, 1H) 13.26 (br. s., 1H). MS (m/z) 507.7 M (+1), $t_R$=1.12, Meth 10

Example 1-54

(5-Chloro-pyridin-2-yl)-{5-[2-(2,6-dichloro-phenyl)-3H-benzoimidazol-5-yl]-[1,3,4]oxadiazol-2-yl}-amine

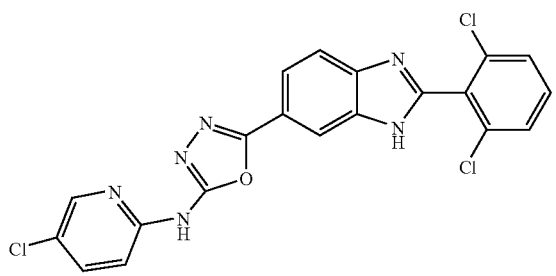

Dissolve 2-amino-5-chloro-pyridine (130 mg, 1.01 mmol) in a biphasic solution of CHCl$_3$ (25 mL) and saturated NaHCO$_3$ (25 mL). Add thiophosgene (46 uL, 0.606 mmol) to the organic phase and stir the reaction vigorously for 2 hr. Add 2-(2,6-dichloro-phenyl)-3H-benzoimidazole-5-carboxylic acid hydrazide (250 mg, 0.778 mmol) and stir overnight. Filter the reaction. Extract the aqueous phase with CHCl$_3$ (25 mL). Concentrate the combined organics and combine with the solid. Evaporate the solvent to yield a yellow solid. Add DMF (3 mL) and EDCI (307 mg, 1.60 mmol) and heat the reaction to 80° C. for 1.5 hr. Allow the reaction to cool to room temp. Dilute with EtOAc (75 mL) and extract with water (15 mL). Dry the organic phase over Na$_2$SO$_4$ and concentrate. Take the concentrate up in DMSO (2 mL) and dilute with water (50 mL). Cool the mixture to 4° C. and collect the precipitate. Recrystallize from toluene/ACN/MeOH to afford the title compound as a cream colored solid: 1H NMR (400 MHz, DMSO-d6) δ ppm 7.62-7.68 (m, 1H) 7.70 (s, 1H) 7.72 (d, J=2.02 Hz, 1H) 7.75-7.85 (m, 1H) 7.85-7.93 (m, 1H) 7.97-8.03 (m, 2H) 8.06 (tautomer, s, 1H) 8.19 (tautomer, s, 1H) 8.39 (dd, J=2.21, 0.95 Hz, 1H) 11.50 (br. s., 1H) 13.30 (br. s., 1H); MS m/z=456.9 (M+1).

Example 1-55

{5-[2-(2,6-Dichloro-phenyl)-3H-benzoimidazol-5-yl]-[1,3,4]oxadiazol-2-yl}-quinolin-2-yl-amine

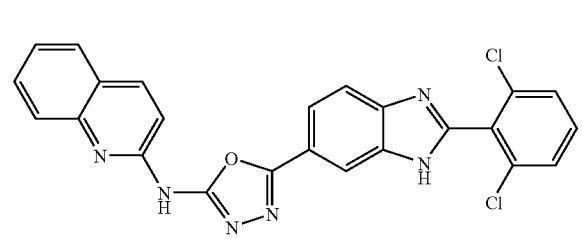

Dissolve 2-amino-quinoline (88 mg, 0.607 mmol) in a biphasic solution of CHCl$_3$ (15 mL) and saturated NaHCO$_3$ (15 mL). Add thiophosgene (47 uL, 0.607 mmol) to the organic phase and stir the reaction vigorously for 3 hr. Add 2-(2,6-dichloro-phenyl)-3H-benzoimidazole-5-carboxylic acid hydrazide (150 mg, 0.467 mmol) and stir overnight. Filter the reaction. Extract the aqueous phase with CHCl$_3$ (20 mL). Concentrate the combined organics and combine with the solid. Evaporate the solvent. Add EDCI (96 mg, 0.500 mmol) and DMF (3 mL). Heat to 80° C. for 1 hr. Upon cooling to room temp dilute the reaction with EtOAc (75 mL) and extract with water (15 mL). Dry the organic phase over Na$_2$SO$_4$ and concentrate. Purify the concentrate by reverse phase HPLC (35-65% ACN/H$_2$O+5 mM NH$_4$OH) to afford the title compound as a yellow solid: 1H NMR (400 MHz, MeOD) δ ppm 7.19 (br. s., 1H) 7.45 (m, 1H) 7.55-7.64 (m, 3H) 7.69-7.75 (m, 2H) 7.82 (d, J=7.83 Hz, 2H) 8.05 (dd, J=8.46, 1.52 Hz, 1H) 8.16 (d, J=9.35 Hz, 1H) 8.32 (br. s., 1H); MS m/z=473.0 (M+1).

Example 1-56

(4-{6-[5-(4-Chloro-phenyl)-[1,3,4]oxadiazol-2-yl]-1H-benzoimidazol-2-yl}-3,5-dimethyl-phenoxy)-acetic acid (16a)

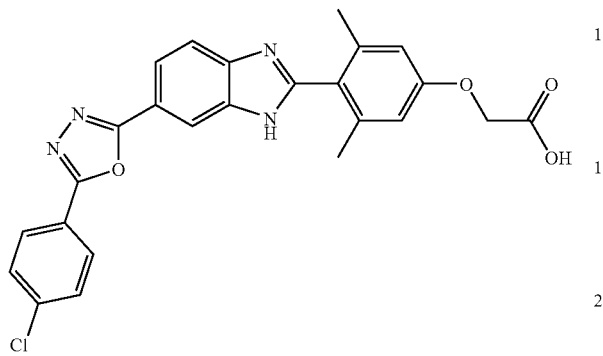

A. (4-{6-[N'-(4-Chloro-benzoyl)-hydrazinocarbonyl]-1H-benzoimidazol-2-yl}-3,5-dimethyl-phenoxy)-acetic acid methyl ester To a solution of 0.300 g (0.847 mmol) of 2-(4-Methoxycarbonylmethoxy-2,6-dimethyl-phenyl)-3H-benzoimidazole-5-carboxylic acid, and 6 mL of DMF was added 0.1338 ml (0.847 mmol) of t-butylaniline, 0.1953 g (1.02 mmol) of EDCI, and 0.1374 g (1.02 mmol) of HOBt. The brown solution was stirred at r.t. for 18 h. To the mixture was added EtOAc, and water, filtered off solid to give the title compound. Used directly in next reaction. MS (m/z) 507.1 M (+1), $t_R$=1.13, Meth 10

B. (4-{6-[5-(4-Chloro-phenyl)-[1,3,4]oxadiazol-2-yl]-1H-benzoimidazol-2-yl}-3,5-dimethyl-phenoxy)-acetic acid methyl ester To a 5 mL microwave vial was added 0.2010 g (0.369 mmol) of (4-{6-[N'-(4-Chloro-benzoyl)-hydrazinocarbonyl]-1H-benzoimidazol-2-yl}-3,5-dimethyl-phenoxy)-acetic acid methyl ester, 5 mL of THF, and 0.1890 g (0.793 mmol) of burgess reagent. The suspension was placed in the microwave at 150° C. for 20 min. The brownish solution was concentrated and the residue was purified by silica gel (ACN/DCM, 1:9 to 5:5) to give the title compound. 1H NMR (400 MHz, DMSO-d6) δ ppm 2.10 (s, 6H) 3.72 (s, 4H) 4.86 (s, 2H) 6.81 (s, 2H) 7.68-7.74 (m, 2.5H) 7.87 (d, J=8.46 Hz, 0.5H) 7.97-8.04 (m, 1H) 8.15-8.24 (m, 2.5H) 8.45 (s, 0.5H) 12.93 (d, J=15.66 Hz, 1H). MS (m/z) 489.1 M (+1), $t_R$=1.40, Meth 10

C. (4-{6-[5-(4-Chloro-phenyl)-[1,3,4]oxadiazol-2-yl]-1H-benzoimidazol-2-yl}-3,5-dimethyl-phenoxy)-acetic acid The title compound was prepared analogous to step B of Intermediate 2. LiOH was used instead. 1H NMR (400 MHz, DMSO-d6) δ ppm 2.10 (s, 6H) 4.72 (s, 2H) 6.78 (s, 2H) 7.71 (d, J=8.72 Hz, 2.5H) 7.82-7.91 (m, 0.5H) 8.00 (br. s., 1H) 8.14-8.27 (m, 2.5H) 8.45 (br. s., 0.5H) 12.97 (d, J=17.68 Hz, 1.7H). MS (m/z) 475.1 M (+1), $t_R$=1.06, Meth 10

Example 1-57

(3,5-Dichloro-4-{6-[5-(4-chloro-phenyl)-[1,3,4]oxadiazol-2-yl]-1H-benzoimidazol-2-yl}-phenoxy)-acetic acid

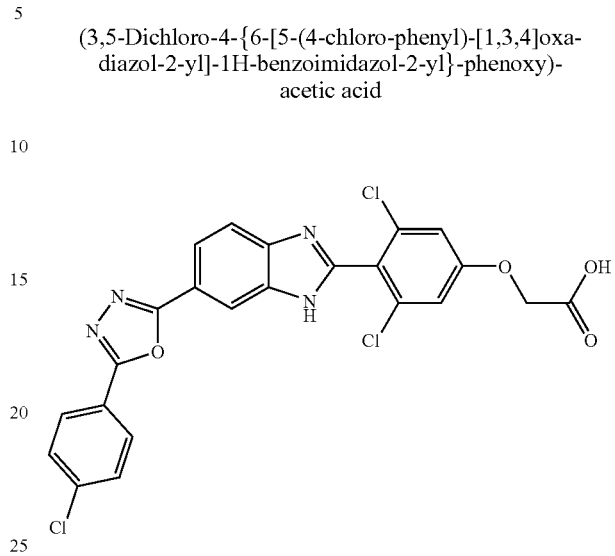

A. 4-(tert-Butyl-dimethyl-silanyloxy)-2,6-dichloro-benzaldehyde

To a 250 ml rbf at 0° C. was added 10.0 g (61.3 mmol) of 3,5-dichlorophenol, 120 mL of DMF, and allowed to stir 10 min. Then added 9.1887 g (135 mmol) of imidazole and the dark yellow solution allowed to stir at 0° C. for 10 min. Then added 10.1770 g (67.5 mmol) t-BDMS-Cl, from pale yellow to clear in 1 min, allowed to stir from 0° C. to r.t. over 18 h. Brought to 0° C., and added 120 mL of water, and stirred 10 min. Extracted with EtOAc, washed with water, brine, and dried with $Na_2SO_4$. Purified on silica gel (EtOAc/Hep, 0:10 to 1:9) to give the title compound. 1H NMR (400 MHz, DMSO-d6) δ ppm −0.00 (s, 6H) 0.73 (s, 9H) 6.70 (d, J=1.89 Hz, 2H) 6.99 (t, J=1.83 Hz, 1H).

B. 2,6-Dichloro-4-hydroxy-benzaldehyde

To a 500 mL rbf at −78° C. was added 80 mL THF, 15.5054 g (55.9 mmol) of 4-(tert-Butyl-dimethyl-silanyloxy)-2,6-dichloro-benzaldehyde, stirred 10 min. Then added 41.1423 mL (57.6 mmol) of sec-butyllithium drop-wise over 25 min, and allowed to stir at −78° C. for 1.5 h. To the mostly yellow suspension was added 6.4682 mL (83.9 mmol) of DMF. The yellow solution was allowed to stir at −78° C. for 5 h. To the reaction mixture was added 1 mL MeOH, and 60 mL of 1 N HCl and allowed to warm to r.t. for 18 h. The brown solution was brought to pH 4, extracted with EtOAc, washed with water, brine, and dried with $Na_2SO_4$. Solid drop out of organic, filtered and rinsed with DCM to give the title compound. 1H NMR (400 MHz, DMSO-d6) δ ppm 6.93 (s, 2H) 10.24 (s, 1H) 11.45 (s, 1H). MS (m/z) 191.0 M (+1), $t_R$=1.07, Meth 10

C. 3,5-Dichloro-4-formyl-phenoxy)-acetic acid methyl ester

To a solution of 1.0346 g (5.42 mmol) of 2,6-Dichloro-4-hydroxy-benzaldehyde, and 4 mL of DMSO was added 0.6176 mL (6.50 mmol) of methyl-bromo-acetate. Then 0.5315 g (0.710 mmol) of $K_2CO_3$ and 0.1235 g (0.0710 mmol) of $Cs_2CO_3$ was added. Allowed to stir at r.t. for 72 h. Added 50 mL water, filtered off solid, rinsed with 300 mL water to give the title compound. 1H NMR (400 MHz, DMSO-d6) δ ppm 3.71 (s, 3H) 5.03 (s, 2H) 7.27 (s, 2H) 10.27 (s, 1H). MS (m/z) 263.0 M (+1), $t_R$=1.21, Meth 10

D. 2-(2,6-Dichloro-4-methoxycarbonylmethoxyphenyl)-3H-benzoimidazole-5-carboxylic acid To a solution of 0.7854 g (5.16 mmol) of 1,2-diaminobenzoic acid, 1.3580 (5.16 mmol) of 3,5-Dichloro-4-formyl-phenoxy)-acetic acid methyl ester, in 10 mL DMSO was added 0.1255 g (0.774 mmol) of $FeCl_3$ portion-wise. The dark brown solution was allowed to stir open to air at r.t. for 6 h. The reaction mixture was extracted with EtOAc, then washed with water, brine, and solid filtered off both the organic and aqueous layer to give the title compound. 1H NMR (400 MHz, DMSO-d6) δ ppm 3.75 (s, 3H) 5.06 (s, 2H) 7.37 (s, 2H) 7.54-7.96 (m, 2H) 8.08-8.35 (m, 1H) 12.79 (br.s., 1H) 13.23 (d, J=16.42 Hz, 1H). MS (m/z) 395.0 M (+1), $t_R$=0.81, Meth 10

E. (3,5-Dichloro-4-{6-[N'-(4-chloro-benzoyl)-hydrazinocarbonyl]-1H-benzoimidazol-2-yl}-phenoxy)-acetic acid methyl ester The title compound was prepared analogous to step A of Example 1-56. MS (m/z) 549.0 M (+1), $t_R$=1.12, Meth 10

F. (3,5-Dichloro-4-{6-[5-(4-chloro-phenyl)-[1,3,4]oxadiazol-2-yl]-1H-benzoimidazol-2-yl}-phenoxy)-acetic acid methyl ester The title compound was prepared analogous to step B of Example 1-56. 1H NMR (400 MHz, DMSO-d6) δ ppm 3.73 (s, 3H) 5.04 (s, 2H) 7.37 (s, 2H) 7.72 (d, J=8.59 Hz, 2H) 7.77 (d, J=8.46 Hz, 0.5H) 7.92 (d, J=8.46 Hz, 0.5H) 8.00-8.09 (m, 1H) 8.17-8.22 (m, 2H) 8.31 (s, 0.5H) 8.49 (s, 0.5H) 13.28 (d, J=11.12 Hz, 1H). MS (m/z) 531.0 M (+1), $t_R$=1.43, Meth 10

G. (3,5-Dichloro-4-{6-[5-(4-chloro-phenyl)-[1,3,4]oxadiazol-2-yl]-1H-benzoimidazol-2-yl}-phenoxy)-acetic acid The title compound was prepared analogous to step C of Example 1-56. 1H NMR (400 MHz, DMSO-d6) δ ppm 5.01 (s, 2H) 7.43 (s, 2H) 7.83 (d, J=8.59 Hz, 2H) 7.90 (br. s., 1H) 8.04 (d, J=6.95 Hz, 1H) 8.17 (d, J=7.45 Hz, 1H) 8.31 (d, J=8.46 Hz, 2H) 8.43 (br. s., 1H) 8.61 (d, J=3.66 Hz, 1H) 13.45 (d, J=12.76 Hz, 1H). MS (m/z) 516.9 M (+1), $t_R$=1.08, Meth 10

Example 1-58

3-(4-{6-[5-(4-Methoxyphenyl)-[1,3,4]oxadiazol-2-yl]-1H-benzoimidazol-2-yl}-3,5-dimethylphenyl)-propionic acid

A. 4-Methoxy-benzoic acid N'-(4-amino-3-nitrobenzoyl)-hydrazide

To a solution of 4-amino-3-nitrobenzoic acid (3.64 g, 20 mmol) in DMF (50 mL) was added HOBT (2.70 g, 20 mmol) and EDCI (3.83 g, 20 mmol). After the addition, the solution was stirred at 25° C. for 10 min then 4-methoxybenzoic acid hydrazide (3.32 g, 20 mmol) was added and followed by the addition of $NEt_3$ (8.35 mL, 60 mmol). The solution was stirred at 25° C. overnight and water was added. The resulting suspension was filtered and the solid was washed with water. The yellow solid was dried under reduced pressure and was purified by flash chromatography (heptane/EtOAc=1:3) to give the title compound. MS: m/z 331 (M+1).

B. 4-[5-(4-Methoxyphenyl)-[1,3,4]oxadiazol-2-yl]-2-nitrophenylamine

A solution of 4-methoxybenzoic acid N'-(4-amino-3-nitrobenzoyl)-hydrazide (750 mg, 2.27 mmol) and Burgess reagent (1.62 g, 6.81 mmol) in THF (15 mL) was microwaved at 150° C. for 20 min. The solvent was removed under reduced pressure and the residue was purified by flash chromatography (heptane/EtOAc=1:3) to give the title compound as a yellow solid. MS: m/z 313 (M+1).

C. 4-[5-(4-Methoxyphenyl)-[1,3,4]oxadiazol-2-yl]-benzene-1,2-diamine

A solution of 4-[5-(4-methoxyphenyl)-[1,3,4]oxadiazol-2-yl]-2-nitrophenylamine (1.0 g, 3.21 mmol) in 80 mL of EtOH/THF (1:1) was hydrogenated over $PtO_2$ (100 mg) at one atm for 2-4 h. The catalyst was filtered through Celite and washed with EtOH and THF. The solvent was removed under reduced pressure to give the title compound as a yellow solid. MS: m/z 283 (M+1).

D. (E)-3-(4-{6-[5-(4-Methoxyphenyl)-[1,3,4]oxadiazol-2-yl]-1H-benzoimidazol-2-yl}-3,5-dimethylphenyl)-acrylic acid methyl ester To a solution of 4-[5-(4-methoxyphenyl)-[1,3,4]oxadiazol-2-yl]-benzene-1,2-diamine (564 mg, 2.0 mmol) and 3-(4-formyl-3,5-dimethylphenyl)-acrylic acid methyl ester (436 mg, 2.0 mmol) (Example 1-60, step C) in 10 mL of DMF and 1 mL of water was added oxone (824 mg, 1.34 mmol) and the mixture was stirred at RT for 20 min. Ethyl acetate was added and stirred for a while then water was added. The organic layer was separated and the aqueous layer was extracted with EtOAc. The combined organic layers were washed with water, brine, dried with MgSO$_4$ and filtered. The solvent was removed under reduced pressure to give the title compound. MS: m/z 481 (M+1).

E. 3-(4-{6-[5-(4-Methoxyphenyl)-[1,3,4]oxadiazol-2-yl]-1H-benzoimidazol-2-yl}-3,5-dimethylphenyl)-propionic acid methyl ester A solution of (E)-3-(4-{6-[5-(4-methoxyphenyl)-[1,3,4] oxadiazol-2-yl]-1H-benzoimidazol-2-yl}-3,5-dimethylphenyl)-acrylic acid methyl ester (1.0 g) in 40 mL EtOH/THF (1:1) was hydrogenated over 5% Pd/C (300 mg) at one atm for 3 h. The catalyst was filtered through Celite and was washed with EtOH and THF. The solvent was removed under reduced pressure and the residue was purified by flash chromatography (heptane/EtOAc=1:2) to give the title compound. MS: m/z 483 (M+1).

F. 3-(4-{6-[5-(4-Methoxyphenyl)-[1,3,4]oxadiazol-2-yl]-1H-benzoimidazol-2-yl}-3,5-dimethylphenyl)-propionic acid To a solution of 3-(4-{6-[5-(4-Methoxyphenyl)-[1,3,4] oxadiazol-2-yl]-1H-benzoimidazol-2-yl}-3,5-dimethylphenyl)-propionic acid methyl ester in MeOH (10 mL) was added 1N NaOH (10 mL). The mixture was stirred at RT for 2 h then the resulting solution was carefully acidified to pH 3-4 with 1N HCl. The resulting precipitate was filtered, washed with water and was dried under reduced pressure to give the title compound. MS: m/z 469.1 (M+1). H$^1$-NMR (MeOD): δ 8.40 (s, broad, 1H), 8.15-8.08 (m, 3H), 7.81 (s, broad, 1H), 7.16 (d, J=8.97 Hz, 2H), 7.10 (s, 2H), 3.91 (s, 3H), 2.93 (t, 2H), 2.55 (t, 2H), 2.15 (s, 6H).

Example 1-59

3-(4-{6-[5-(3-Chlorophenylamino)-[1,3,4]oxadiazol-2-yl]-1H-benzoimidazol-2-yl}-3,5-dimethylphenyl)-propionic acid

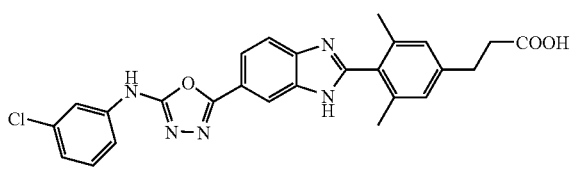

A. 2,2,2-Trifluoro-N-(4-formyl-3,5-dimethylphenyl)-acetamide

To a solution of N-(4-bromo-3,5-dimethylphenyl)-2,2,2-trifluoroacetamide (U.S. Pat. No. 6,391,865) (14.0 g. 47.3 mmol) in THF (200 mL) under nitrogen atmosphere at −78° C. was added slowly methyllithium/LiBr (44.1 mL of a 1.5 M solution in Et$_2$O, 66.2 mmol). After 5 min of stirring, sec-BuLi (47.3 mL of a 1.4 M solution in cyclohexane, 66.2 mmol) was added slowly to the reaction solution at −78° C. After 5 min, anhydrous DMF (25.5 mL, 331 mmol) was added slowly then the solution was warmed to 25° C. After 30 min the reaction mixture was quenched with water. The aqueous layer was extracted with CH$_2$Cl$_2$ and the combined organic layers were washed with water, brine, dried over MgSO$_4$ and filtered. The solvent was removed under reduced pressure to give the title compound as a yellow solid. MS: m/z 246 (M+1).

B. 4-Amino-2,6-dimethylbenzaldehyde

A mixture of the above 2,2,2-trifluoro-N-(4-formyl-3,5-dimethylphenyl)-acetamide in MeOH (30 mL) and 1 N NaOH (30 mL) was stirred at RT overnight. To the suspension was added 100 mL of water and the solid was filtered, washed with water, and dried. The aqueous layer was extracted with EtOAc and the organic layer was washed with water, brine, dried with MgSO$_4$, and filtered. The solvent was removed under reduced pressure and the residue was purified by flash chromatography (heptane/EtOAc=4:1) to give the title compound. MS: m/z 150 (M+1).

C. 3-(4-Formyl-3,5-dimethylphenyl)-acrylic acid methyl ester

To a suspension of 4-amino-2,6-dimethylbenzaldehyde (1.0 g., 6.71 mmol) in enough 42% HBF$_4$ to be stirred at 0° C. was added a solution of NaNO$_2$ (463 mg, 6.71 mmol) in water (5 mL) slowly. After 30 min at 0° C., MeOH (20 mL) was added followed by Pd(OAc)$_2$ (229 mg) and methyl acrylate (1155 mg, 13.42 mmol). The reaction mixture was heated at 80° C. for 30 min then the suspension was filtered through Celite and washed with CH$_2$Cl$_2$. The filtrate was extracted with CH$_2$Cl$_2$ and the organic layer was washed with water, brine, dried with MgSO$_4$, and filtered. The solvent was removed under reduced pressure and the residue was purified by flash chromatography (heptane/EtOAc=10:1 to 5:1) to give the title compound. MS: m/z 219 (M+1).

D. 3-(4-Formyl-3,5-dimethylphenyl)-propionic acid methyl ester

A mixture of 3-(4-formyl-3,5-dimethylphenyl)-acrylic acid methyl ester (900 mg, 4.1 mmol) and 10% Pd/C (90 mg) in CH$_2$Cl$_2$ (20 mL) was hydrogenated at one atm overnight. The catalyst was filtered through Celite and washed with CH$_2$Cl$_2$. The solvent was removed under reduced pressure and the residue was purified by flash chromatography (heptane/EtOAc=5:1) to give the title compound. MS: m/z 221 (M+1).

E. 4-Amino-3-nitrobenzoic acid hydrazide

To a suspension of 4-amino-3-nitrobenzoic acid (1.64 g, 9 mmol) in THF (25 mL) was added diisopropylcarbodiimide (1.13 g, 9 mmol). The mixture was stirred at RT for 15 min and to the resulting yellow solution was added hydrazine (600 mg, 18 mmol). The resulting orange suspension was stirred at RT for 2 h. The solid was filtered and washed twice with THF to give the title compound: MS: m/z 195.1 (M−1).

F. [5-(4-Amino-3-nitrophenyl)-[1,3,4]oxadiazol-2-yl]-(3-chlorophenyl)-amine

To a solution of 4-amino-3-nitrobenzoic acid hydrazide (320 mg, 1.63 mmol) in DMF (8 mL) was added 3-chloroisothiocyanate (277 mg, 1.63 mmol). The mixture was stirred at RT for 2 h then EDCI (627 mg, 3.26 mmol) was added and the mixture was stirred at 65° C. for 5 h. The mixture was allowed to cool then was poured into water. The precipitate was filtered, washed with water and dried under reduced pressure to give the title compound as an orange solid. MS: m/z 330.1 (M−1).

G. 4-[5-(3-Chlorophenylamino)-[1,3,4]oxadiazol-2-yl]-benzene-1,2-diamine

A suspension of [5-(4-amino-3-nitrophenyl)-[1,3,4]oxadiazol-2-yl]-(3-chlorophenyl)-amine (245 mg, 0.74 mmol) and PtO$_2$ (50 mg) in MeOH (30 mL) was hydrogenated at one atm for 4 h. The catalyst was filtered over Celite and the filtrate was evaporated under reduced pressure to give the title compound. This was used directly in the next reaction.

H. 3-(4-{6-[5-(3-Chlorophenylamino)-[1,3,4]oxadiazol-2-yl]-1H-benzoimidazol-2-yl}-3,5-dimethylphenyl)-propionic acid methyl ester To a solution of 4-[5-(3-chlorophenylamino)-[1,3,4]oxadiazol-2-yl]-benzene-1,2-diamine (210 mg, 0.7 mmol) and 3-(4-formyl-3,5-dimethylphenyl)-propionic acid methyl ester (169 mg, 0.77 mmol) (from step D) in DMSO (2.5 mL) was added Yb(OTf)$_3$ (86 mg, 0.14 mmol) and the mixture was stirred at RT for 72 h. The mixture was poured into water and the resulting precipitate was filtered and washed with water. The solid was purified by flash chromatography using 10% MeOH/CH$_2$Cl$_2$ as eluent to give the title compound as a tan solid. MS: m/z 502.0 (M+1). H$^1$-NMR (DMSO-d6): δ ppm 12.91 (m, 0.6H), 10.93 (s, 0.3H), 10.48 (dd, 0.3H), 8.33 (s, 0.4H), 8.13 (s, 0.6H), 7.89-7.73 (M, 2.3H), 7.68 (d, 0.3H), 7.59 (d, 0.4H), 7.52 (m, 1H), 7.46-7.35 (m, 1H), 7.08 (s, 3H), 3.61 (s, 3H), 2.87 (t, 2H), 2.69 (t, 2H), 2.10 (s, 3H), 2.09 (s, 3H).

I. 3-(4-{6-[5-(3-Chlorophenylamino)-[1,3,4]oxadiazol-2-yl]-1H-benzoimidazol-2-yl}-3,5-dimethylphenyl)-propionic acid To a solution of 3-(4-{6-[5-(3-chlorophenylamino)-[1,3,4]oxadiazol-2-yl]-1H-benzoimidazol-2-yl}-3,5-dimethylphenyl)-propionic acid methyl ester (190 mg, 0.38 mmol) in MeOH (10 mL) was added 1.0 N NaOH (1.14 mL, 1.14 mmol) and the mixture was stirred at RT for 24 h. The solvent was removed under reduced pressure and water was added. The resulting solution was washed with EtOAc and 1.0 N HCl (1.14 mL) was added to the aqueous phase. The mixture was extracted with EtOAc and the organic phase was dried over sodium sulfate. The solvent was removed under reduced pressure and the resulting gum was triturated with MeCN to give the title compound as a beige solid. MS: m/z 488.1 (M+1). H$^1$-NMR (DMSO-d6): δ ppm 12.91 (s, broad, 0.6H), 12.12 (s, broad, 0.7H), 10.93 (s, 0.6H), 8.17-7.95 (m, 1H), 7.90-7.65 (m, 3H), 7.53 (d, J=9.47 Hz, 1H), 7.41 (t, 1H), 7.12-7.05 (m, 3H), 2.84 (t, 2H), 2.59 (t, 2H), 2.10 (s, 6H).

Example 1-60

3-(4-{6-[5-(4-Methoxyphenylamino)-[1,3,4]oxadiazol-2-yl]-1H-benzoimidazol-2-yl}-3,5-dimethylphenyl)-propionic acid

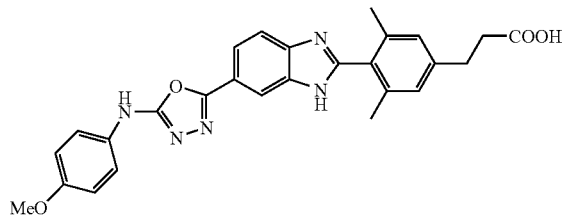

A. 4-[5-(4-Methoxyphenyl)-[1,3,4]oxadiazol-2-yl]-2-nitrophenylamine

The title compound was prepared analogous to Example 1-59, steps E, F and G using 4-methoxyphenylisothiocyanate in step F.

B. 3-(4-{6-[5-(4-Methoxy-phenylamino)-[1,3,4]oxadiazol-2-yl]-1H-benzoimidazol-2-yl}-3,5-dimethylphenyl)-propionic acid methyl ester To a mixture of 4-[5-(4-methoxyphenyl)-[1,3,4]oxadiazol-2-yl]-2-nitrophenylamine (320 mg, 0.98 mmol) and 3-(4-formyl-3,5-dimethylphenyl)-propionic acid methyl ester (215 mg, 0.98 mmol) (from Example 1-60, step D) in EtOH (10 mL) was added a solution of sodium dithionite (511 mg, 2.94 mmol) in water (4 mL) and the mixture was stirred at 70° C. for 5 h. After cooling the mixture to RT, ammonium hydroxide was added. The mixture was extracted with EtOAc (2×) and the combined organic layers were dried over magnesium sulfate. The solvent was removed under reduced pressure and the residue was purified by chromatography using a gradient of 80 to 100% EtOAc/heptane as eluent to give the title compound. MS: m/z 498.1 (M+1).

C. 3-(4-{6-[5-(4-Methoxyphenylamino)-[1,3,4]oxadiazol-2-yl]-1H-benzoimidazol-2-yl}-3,5-dimethylphenyl)-propionic acid The title compound was prepared analogous to Example 1-59, step I. MS: m/z 482.1 (M+1). H$^1$-NMR (DMSO-d6): δ ppm 13.00 (s, broad, 1H), 10.47 (s, 1H), 8.04 (s, 1H), 7.78 (m, 2H), 7.56 (d, J=8.97 Hz, 2H), 7.07 (s, 2H), 6.97 (d, J=8.97 Hz, 2H), 3.74 (s, 3H), 2.82 (t, 2H), 2.50 (t, 2H), 2.09 (s, 6H).

Example 1-61

3-(4-{6-[5-(4-Chlorophenyl)-[1,3,4]oxadiazol-2-yl]-1H-benzoimidazol-2-yl}-3,5-dimethylphenyl)-propionic acid

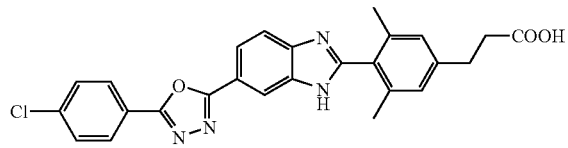

The title compound was prepared analogous to Example 1-58 using 4-chlorobenzoic acid hydrazide in step A and 3-(4-formyl-3,5-dimethylphenyl)-propionic acid methyl ester (Example 1-60, step D) in step D. MS: m/z 473.7 (M+1). $H^1$-NMR (MeOD): δ ppm 8.43 (s, 1H), 8.17 (d, J=8.72 Hz, 2H), 8.13 (d, J=8.46 Hz, 1H), 7.82 (d, J=8.46 Hz, 1H), 7.65 (d, J=8.84 Hz, 2H), 7.10 (s, 2H), 2.93 (t, 2H), 2.64 (t, 2H), 2.16 (s, 6H).

Example 1-62

3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid

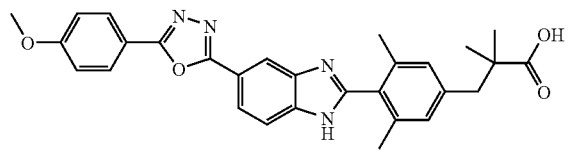

A. 3-(4-formyl-3,5-dimethyl-phenyl)-2,2-dimethyl-propionic acid methyl ester To a stirred solution of 3-(4-formyl-3,5-dimethylphenyl)-propionic acid methyl ester (prepared as described in Example 1-60, 2.2 g, 10 mmol) and ethane-1,2-diol (1.86 g, 30 mmol) in toluene (50 mL) was added p-TsOH.H$_2$O (38 mg, 0.2 mmol) and the solution was refluxed using a Dean-Stark apparatus overnight. The solvent was removed under reduced pressure and the residue was purified by flash chromatography using heptane/EtOAc (5:1) as eluent to give 3-(4-[1,3]dioxolan-2-yl-3,5-dimethylphenyl)-propionic acid methyl ester as a colorless oil.

To a solution of 3-(4-[1,3]dioxolan-2-yl-3,5-dimethylphenyl)-propionic acid methyl ester (2.0 g, 7.55 mmol) in THF (30 mL) cooled to −78° C. under N$_2$ protection, was added slowly LDA (16.8 mL of a 1.8 M solution in THF, 30.2 mmol). After 30 min, MeI (4.29 g, 30.2 mmol) was added slowly to the solution. The solution was stirred at −78° C. for 30 min then the reaction mixture was quenched with water. The aqueous layer was extracted with EtOAc and the organic layer was washed with water, brine, dried with MgSO$_4$ and filtered. The solvent was removed under reduced pressure and the residue was purified by flash chromatography using heptane/EtOAc (5:1) as eluent to give 3-(4-[1,3]dioxolan-2-yl-3,5-dimethylphenyl)-2,2-dimethylpropionic acid methyl ester as a colorless oil.

To a stirred solution of 3-(4-[1,3]dioxolan-2-yl-3,5-dimethylphenyl)-2,2-dimethylpropionic acid methyl ester (1.7 g, 5.8 mmol) in acetone (20 mL) and water (0.3 mL) was added Amberlyst-15 (233 mg). The suspension was stirred at ambient temperature overnight and the suspension was filtered and washed with acetone. The solvent was removed under reduced pressure and the residue was purified by flash chromatography using heptane/EtOAc (5:1) to give 3-(4-formyl-3,5-dimethylphenyl)-2,2-dimethylpropionic acid methyl ester as a pale-yellow oil.

An alternative synthesis of the title compound is as follows.

Zn—Cu couple was stirred vigorously in anhydrous toluene and dimethylacetamide (12.5:1 v/v) at room temperature with nitrogen gas bubbling through the mixture for 15 minutes. 3-iodo-2,2-dimethyl propionate methyl ester (1.35 equiv) was added by syringe and the reaction mixture was heated at 110° C. (oil bath temperature) for 5 h under nitrogen atmosphere. It was cooled to 70° C. and 1.0 equiv. of 4-formyl-3,5-dimethylphenyl trifluoromethanesulfonate was added followed by a subsequent addition of a solution of Pd(PPh$_3$)$_4$ (3 mol %) in anhydrous toluene. The reaction was stirred at the same temperature for 4 h until LCMS analysis indicated the complete consumption of the starting triflate. It was cooled to room temperature and the insolubles were removed by filtration. The filtrate was placed in a separation funnel and washed with 1 N HCl and brine. The organic layer was dried with MgSO$_4$ and concentrated in vacuo. The concentrate was purified by column chromatography (heptane/ethyl acetate) to provide the desired product. LCMS: Method 10, retention time=1.41 min, (M+H)+=249.2.

B. 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid methyl ester Oxone (420 mg, 0.683 mmol) was added to a mixture of 3-(4-formyl-3,5-dimethyl-phenyl)-2,2-dimethyl-propionic acid methyl ester (250 mg, 1.00 mmol) and 4-[5-(4-Methoxy-phenyl)-[1,3,4]oxadiazol-2-yl]-benzene-1,2-diamine (prepared as described in Example 1-59, 300 mg, 1.06 mmol) in DMF (8 mL) and water (0.8 mL), and the mixture was stirred at room temperature for 18 h. The mixture was partitioned between EtOAc and water. The EtOAc extract was washed with brine, dried over Na2SO4, concentrated and chromatographed to give the title compound. m/z 511.3 (MH+).

C. 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid A mixture of 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid methyl ester (340 mg, 0.667 mmol) and aqueous 1M NaOH (5 mL, 5 mmol) in MeOH (5 mL) was stirred at room temperature for 18 h and then heated at 50° C. for 1 h. After the mixture was cooled to room temperature, the mixture was slowly acidified to pH 2~3 by addition of 3M HCl. The product precipitated and was separated from the solution. The solid was dissolved in a small quantity of DMSO and purified by HPLC (basic) to give the title compound as a solid. 1H NMR (CD3OD, 400 MHz) δ ppm 8.55-8.45 (m, 1H), 8.23 (d, J=8 Hz, 2H), 8.22 (d, J=8 Hz, 1H), 7.95-7.85 (m, 1H), 7.26 (d, J=8 Hz, 2H), 7.15 (s, 2H), 4.02 (s, 3H), 2.99 (s, 2H), 2.26 (s, 6H), 1.30 (s, 6H). m/z 497.2 (MH+).

Example 1-63

[3-(4-{6-[5-(4-Chlorophenyl)-[1,3,4]oxadiazol-2-yl]-1H-benzoimidazol-2-yl}-3,5-dimethylphenyl)-propyl]-phosphonic acid

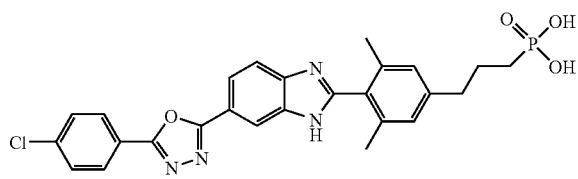

A. [(E)-3-(4-Formyl-3,5-dimethyl-phenyl)-allyl]-phosphonic acid diethyl ester

To a suspension of 4-amino-2,6-dimethylbenzaldehyde (3.0 g, 20.1 mmol) (Example 1-60, step B) in enough 42% HBF$_4$ to be stirred at 0° C. was added a solution of NaNO$_2$ (1.39 g, 20.1 mmol) in water (10 ml) slowly. After 30 min at 0° C., MeOH (50 mL) was added and followed by Pd(OAc)$_2$ (677 mg) and diethyl allylphosphonate (5.38 g, 30.2 mmol). The reaction mixture was heated at 80° C. for 30 min and the suspension was filtered through Celite, washed with CH$_2$Cl$_2$. The filtrate was extracted with CH$_2$Cl$_2$ and the combined organic layers were washed with water, brine, dried with MgSO$_4$, and filtered. The solvent was removed under reduced pressure and the residue was purified by flash chromatography using a gradient of heptane/EtOAc (10:1 to 5:1 then followed by 100% EtOAc) to give the title compound as a light yellow oil. MS: m/z 311 (M+1).

B. [(E)-3-(4-{6-[5-(4-Chlorophenyl)-[1,3,4]oxadiazol-2-yl]-1H-benzoimidazol-2-yl}-3,5-dimethyl-phenyl)-allyl]-phosphonic acid diethyl ester The title compound was prepared analogous to Example 1-59 (steps A-E) using 4-chlorobenzoic acid hydrazide in step A and [(E)-3-(4-formyl-3,5-dimethyl-phenyl)-allyl]-phosphonic acid diethyl ester in step D.

C. [3-(4-{6-[5-(4-Chlorophenyl)-[1,3,4]oxadiazol-2-yl]-1H-benzoimidazol-2-yl}-3,5-dimethylphenyl)-propyl]-phosphonic acid To a solution of [(E)-3-(4-{6-[5-(4-chlorophenyl)-[1,3,4] oxadiazol-2-yl]-1H-benzoimidazol-2-yl}-3,5-dimethylphenyl)-allyl]-phosphonic acid diethyl ester (1.44 g, 2.5 mmol) in CH$_2$Cl$_2$ (15 mL) was added trimethylsilylbromide (1.62 mL, 12.5 mmol) and the mixture was stirred at RT for 18 h. The solvent was removed under reduced pressure and the residue was purified by reverse phase HPLC using a gradient of 0-80% MeCN/water containing 0.7% NH$_4$OH to give the title compound. MS: m/z 523.1 (M+1). H$^1$-NMR (DMSO-d6): δ ppm 8.46 (s, 0.6H), 8.19 (d, J=8.59 Hz, 2H), 8.0 (d, J=8.21 Hz, 1H), 7.88 (s broad, 0.4H), 7.72 (d, J=8.59 Hz, 2H), 7.05 (s, 2H), 2.64 (t, 2H), 2.11 (s, 6H), 1.78 (m, 2H), 1.41 (m, 2H).

Example 1-64

(3-{3,5-Dimethyl-4-[6-(5-phenyl-[1,3,4]oxadiazol-2-yl)-1H-benzoimidazol-2-yl]-phenyl}-propyl)-phosphonic acid

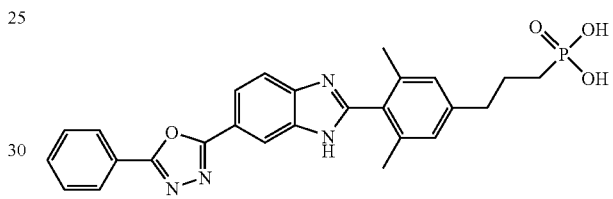

The title compound was isolated as a by-product of the hydrogenation and hydrolysis steps from Example 1-63 (steps B and C). MS: m/z 489.1 (M+1). H$^1$-NMR (DMSO-d6): δ ppm 13.06 (s, broad, 1H), 8.45 (s, broad, 0.6H), 8.28-8.15 (m, 2.4H), 8.01 (d, J=8.21 Hz, 1H), 7.94-7.62 (m, 4H), 7.05 (s, 2H), 2.65 (t, 2H), 2.11 (s, 6H), 1.78 (m, 2H), 1.42 (m, 2H).

Example 1-65

[3-(4-{6-[5-(4-Methoxyphenyl)-[1,3,4]oxadiazol-2-yl]-1H-benzoimidazol-2-yl}-3,5-dimethylphenyl)-propyl]-phosphonic acid

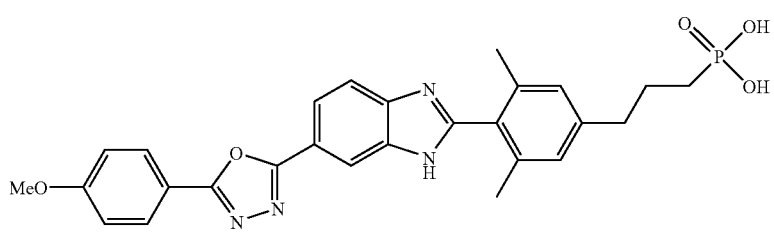

The title compound was prepared analogous to Example 1-58 using [(E)-3-(4-formyl-3,5-dimethylphenyl)-allyl]-phosphonic acid diethyl ester (Example 1-63, step A) in step D. MS: m/z 519.1 (M+1). H$^1$-NMR (MeOD): δ ppm 8.53 (s, 1H), 8.32 (d, J=10.23 Hz, 1H), 8.13 (d, J=8.97 Hz, 2H), 7.98 (d, J=7.96 Hz, 1H), 7.18 (s, 3H), 7.16 (s, 1H), 3.92 (s, 3H), 2.78 (t, 2H), 2.23 (s, 6H), 1.97 (m, 2H), 1.71 (m, 2H).

Example 1-66

3-(4-{6-[5-(4-Methoxyphenyl)-[1,3,4]oxadiazol-2-yl]-1H-indol-2-yl}-3,5-dimethylphenyl)-propionic acid

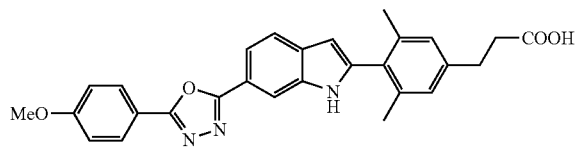

A. 4-Bromomethyl-3-nitrobenzoic acid benzyl ester

To a solution of 4-bromomethyl-3-nitrobenzoic acid (2.0 g, 7.69 mmol), benzyl alcohol (796 □L, 832 mg, 7.69 mmol) and 4-dimethylaminopyridine (9.4 mg, 77 µmol) in dichloromethane (5 mL) was added DCC (1.59 g, 7.71 mmol) and the mixture was at stirred RT for 3 h. The mixture was filtered and the filtrate concentrated. The residue was purified by chromatography using a 0-30% gradient of heptane/ethyl acetate to give the title compound as an oil.

B. Benzyl 4-{(E)-2-[4-((E)-2-methoxycarbonylvinyl)-2,6-dimethylphenyl]-vinyl}-3-nitrobenzoate A mixture of 4-bromomethyl-3-nitrobenzoic acid benzyl ester (2.06 g, 5.88 mmol) and triphenylphosphine (1.54 g, 5.87 mmol) in DMF (10 mL) was heated at 100° C. for 1 h. To this solution was then added 3-(4-formyl-3,5-dimethylphenyl)-acrylic acid methyl ester (1.28 g, 5.86 mmol) (Example 1-60, step C) and potassium carbonate (1.63 g, 11.8 mmol) and the mixture was stirred for at 100° C. 18 h. The mixture was poured into ethyl acetate and extracted with water once and brine five times. The organic layer was dried, filtered, and solvent removed under reduced pressure. The residue was purified by chromatography using a 0-40% gradient of heptane/ethyl acetate to give the title compound.

C. Benzyl 2-[4-((E)-2-methoxycarbonylvinyl)-2,6-dimethylphenyl]-1H-indole-6-carboxylate A mixture of benzyl 4-{(E)-2-[4-((E)-2-methoxycarbonylvinyl)-2,6-dimethylphenyl]-vinyl}-3-nitrobenzoate (1.87 g, 3.97 mmol) and trimethyl phosphite (5.0 mL, 5.26 g, 42 mmol) was heated at 110° C. for 3 h. The solvent was removed under reduced pressure and the residue chromatographed using a 10-50% gradient of heptane/ethyl acetate to give the title compound.

D. 2-[4-(2-Methoxycarbonylethyl)-2,6-dimethylphenyl]-1H-indole-6-carboxylic acid A mixture of benzyl 2-[4-((E)-2-methoxycarbonylvinyl)-2,6-dimethylphenyl]-1H-indole-6-carboxylate (950 mg, 2.16 mmol) and 10% palladium on carbon (95 mg) in 100 mL of 1:1 ethyl acetate/ethanol was stirred under a hydrogen balloon for 18 h. The catalyst was filtered through Celite and the filtrate was removed under reduced pressure to leave the title compound. MS: m/z 352.2 (M+1); Retention time=1.35 min (Method 10).

E. Methyl 3-(4-{6-[N'-(4-methoxybenzoyl)-hydrazinocarbonyl]-1H-indol-2-yl}-3,5-dimethyl-phenyl)-propionate To a mixture of 2-[4-(2-methoxycarbonylethyl)-2,6-dimethylphenyl]-1H-indole-6-carboxylic acid (200 mg, 570 µmol) and HOBT (85 mg, 630 µmol) in THF (10 mL) was added EDCI (164 mg, 860 µmol) and the solution was stirred at RT for 10 min. Then a solution of 4-methoxybenzoic acid hydrazide (104 mg, 630 µmols) in THF (5 mL) was added and the mixture was stirred at RT for 18 h. The solvent was removed under reduced pressure and the residual material was chromatographed using a 50-90% gradient of heptane/ethyl acetate to give the title compound.

F. Methyl 3-(4-{6-[5-(4-methoxyphenyl)-[1,3,4]oxadiazol-2-yl]-1H-indol-2-yl}-3,5-dimethylphenyl)-propionate A mixture of methyl 3-(4-{6-[N'-(4-methoxybenzoyl)-hydrazinocarbonyl]-1H-indol-2-yl}-3,5-dimethyl-phenyl)-propionate (220 mg, 440 µmol) and Burgess reagent (210 mg, 880 µmol) in THF (10 mL) was heated in a microwave apparatus at 150° C. for 30 min. The solvent was removed under reduced pressure, and the residue chromatographed using a 30-70% gradient of heptane/ethyl acetate to afford the title compound.

G. 3-(4-{6-[5-(4-Methoxyphenyl)-[1,3,4]oxadiazol-2-yl]-1H-indol-2-yl}-3,5-dimethylphenyl)-propionic acid A mixture of methyl 3-(4-{6-[5-(4-methoxyphenyl)-[1,3,4]oxadiazol-2-yl]-1H-indol-2-yl}-3,5-dimethylphenyl)-propionate (35 mg, 73 µmol) and 1N NaOH (174 µL, 174 µmol) in 5 mL of 2:1 water/methanol and 5 mL THF was heated at 50° C. for 4 h. The solvent was removed under reduced pressure and the residue was stirred with water, and neutralized with 174 µL of 1 N HCl. The precipitate was filtered, washed with water, and dried to the title compound. $H^1$-NMR (DMSO-d6): δ ppm 12.17 (s, broad, 1H), 11.62 (s, 1H), 8.08 (m, 3H), 7.76 (m, 2H), 7.19 (d, J=8.8 Hz, 2H), 7.06 (s, 2H), 6.46 (s, 1H), 3.88 (s, 3H), 2.82 (t, J=7.4 Hz, 2H), 2.58 (t, J=7.6 Hz, 2H), 2.12 (s, 6H). MS: m/z 468.2 (M+1); Retention time=1.33 min (Method 10). High Res MS (M+H): theory 468.1923, measured 468.1918.

Example 1-67

3-(3,5-Dichloro-4-{6-[5-(4-chloro-phenyl)-[1,3,4]oxadiazol-2-yl]-1H-benzoimidazol-2-yl}-phenyl)-propionic acid

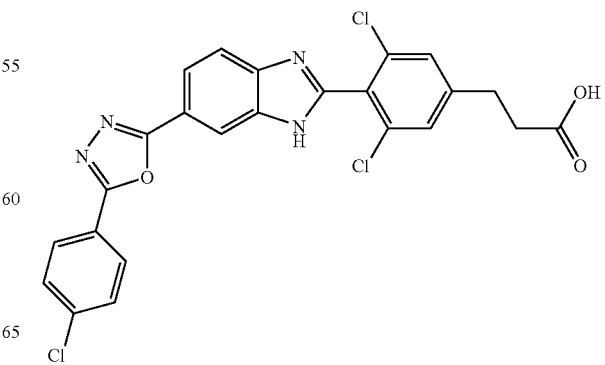

A. 3-(3,5-Dichloro-4-formyl-phenyl)-propionic acid tert-butyl ester 3,5-dichloro-iodo-benzene (5 g, 18 mmol) was stirred at room temperature as a solution in DMF (50 mL) containing tert butyl acrylate (6.5 mL, 2.5 eq), tetrabutyl ammonium chloride hydrate (5.1 g, 1 eq), potassium acetate (5.4 g, 3 eq) and palladium (II) acetate (~200 mg, 30 mol %) for 5 hours. Reaction mixture was reduced in vacuo, partitioned between water and ethyl acetate. Ethyl acetate fractions were dried over magnesium sulfate, filtered over a small plug of silica gel. Silica gel plug washed with 10% Ethyl acetate/n-heptanes to afford 3-(3,5-Dichloro-phenyl)-acrylic acid tert butyl ester after evaporation as a white solid. 1H NMR (400 MHz, DMSO-D6) δ ppm 1.46 (s, 9H) 6.69 (d, J=16.04 Hz, 1H) 7.49 (d, J=16.04 Hz, 1H) 7.59 (t, J=1.89 Hz, 1H) 7.81 (d, J=1.77 Hz, 2H). A solution of 3-(3,5-Dichloro-phenyl)-acrylic acid tert butyl ester (4 g, 14 mmol) in ethanol (100 mL) was charged with platinum oxide (800 mg), after purging reaction mixture with nitrogen. Attached balloon of hydrogen and stirred vigorously at room temperature over night. After removal of excess hydrogen, catalyst was removed by filtering mixture over a pad of celite and the resulting solution was evaporated to afford 3-(3,5-dichloro-phenyl)-propionic acid tert-butyl ester as an oil (3.8 g; 94% isolated yield). 1H NMR (400 MHz, CHLOROFORM-D) δ ppm 1.41 (s, 9H) 2.52 (s, 2H) 2.85 (s, 2H) 7.08 (s, 2H) 7.18 (s, 1H).

To a solution of 3-(3,5-Dichloro-phenyl)-propionic acid tert butyl ester (1 g, 3.6 mmol) in THF (50 mL) at −78 C was added dropwise s-butyl lithium (1.4 M cyclohexanes; 5.7 mL, 2.2 eq). The resulting red colored homogeneous solution was stirred under nitrogen at −78 C for one hour, at which time DMF (560 mL, 2 eq) was added. After 30 minutes, quenched reaction with saturated ammonium chloride solution at −78 C. Removed ice bath and allowed reaction to reach room temperature. Evaporation of volatiles in vacuo, partitioned between water and ethyl acetate. Combined ethyl acetate fractions were dried over magnesium sulfate and appropriately loaded onto a silica gel column. Isolated 600 mg of titled compound after chromatography (isocratic 20% ethyl acetate/n-heptanes). 1H NMR (400 MHz, CHLOROFORM-D) δ ppm 1.35-1.44 (m, 10H) 2.55 (t, J=7.45 Hz, 2H) 2.90 (t, J=7.45 Hz, 2H) 7.23 (s, 2H) 10.45 (s, 1H).

B. 4-[5-(4-Chloro-phenyl)-[1,3,4]oxadiazol-2-yl]-2-nitro-phenylamine

To a 20 mL microwave vial was added 1.00 g (2.99 mmol) of 4-Chloro-benzoic acid N'-(4-amino-3-nitro-benzoyl)-hydrazide (A in Example 1-28), 12 mL of THF, and 1.9934 g (8.36 mmol) of burgess reagent. The suspension was placed in the microwave at 150° C. for 30 min. To the orange/yellow suspension was added 5 mL of MeOH and the precipitates were collected by filtration to yield the title compound. 1H NMR (400 MHz, DMSO-d6) δ ppm 7.31 (d, J=8.97 Hz, 1H) 7.80 (d, J=8.59 Hz, 2H) 8.12-8.19 (m, 2.7H) 8.25 (d, J=8.59 Hz, 2H) 8.77 (d, J=2.02 Hz, 1H). MS (m/z) 317.0 M (+1), $t_R$=1.33, Meth 10

B. 4-[5-(4-Chloro-phenyl)-[1,3,4]oxadiazol-2-yl]-benzene-1,2-diamine

To a 25 mL rbf was added 0.4137 g (1.31 mmol) of 4-[5-(4-Chloro-phenyl)-[1,3,4]oxadiazol-2-yl]-2-nitro-phenylamine, 4 mL of THF/EtOH (1:1). Vacuum flushed 3×, then added 0.1655 g of PtO$_2$ (40% by weight) as a slurry in 2 mL of THF/EtOH (1:1). Flushed with H$_2$ 3×. Allowed to stir at r.t. for 18 h. Added 10 ml DCM, and Celite let stir 1 h, then filtered over Celite pad, and rinsed with 20 mL DCM. Reduced in vacuo to give the title compound. 1H NMR (400 MHz, DMSO-d6) δ ppm 4.85 (br. s., 1.7H) 5.31 (br. s., 1.7H) 6.62 (d, J=8.08 Hz, 1H) 7.19 (dd, J=8.08, 1.89 Hz, 1H) 7.26 (d, J=2.02 Hz, 1H) 7.66-7.70 (m, 2H) 8.02-8.06 (m, 2H). MS (m/z) 287.2 M (+1), $t_R$=1.18, Meth 10

C. 3-(3,5-Dichloro-4-{6-[5-(4-chloro-phenyl)-[1,3,4]oxadiazol-2-yl]-1H-benzoimidazol-2-yl}-phenyl)-propionic acid tert-butyl ester To a 20 ml scint. vial was added 0.3783 g (1.32 mmol) 4-[5-(4-Chloro-phenyl)-[1,3,4]oxadiazol-2-yl]-benzene-1,2-diamine, 0.4000 g (1.32 mmol) of 3-(3,5-Dichloro-4-formyl-phenyl)-propionic acid tert-butyl ester (step A), and 6 mL of DMSO. To this dark brown solution was added 0.0321 g (0.198 mmol) of FeCl$_3$. Allowed to stir open to air for 72 h. Extracted with EtOAc, and washed with water, brine and dried with Na$_2$SO$_4$. Purified on silica gel (ACN/DCM, 1:9 to 4:6) to give the title compound. 1H NMR (400 MHz, DMSO-d6) δ ppm 1.39 (9H) 2.64 (t, J=7.33 Hz, 2H) 2.92 (t, J=7.26 Hz, 2H) 7.60 (s, 2H) 7.72 (d, 2H) 7.78 (d, J=8.59 Hz, 0.5H) 7.92 (d, J=8.46 Hz, 0.5H) 8.00-8.09 (m, 1H) 8.17-8.22 (m, 2H) 8.31 (s, 0.5H) 8.50 (s, 0.5H) 13.32 (d, J=11.24 Hz, 1H). MS (m/z) 571.1 M (+1), $t_R$=1.59, Meth 10

D. 3-(3,5-Dichloro-4-{6-[5-(4-chloro-phenyl)-[1,3,4]oxadiazol-2-yl]-1H-benzoimidazol-2-yl}-phenyl)-propionic acid To a 100 ml rbf was added 0.090 g (0.157 mmol) of 3-(3,5-Dichloro-4-{6-[5-(4-chloro-phenyl)-[1,3,4]oxadiazol-2-yl]-1H-benzoimidazol-2-yl}-phenyl)-propionic acid tert-butyl ester, a few drops of anisole, and 3 mL 4M HCl in 1,4-dioxane. The purple solution was allowed to stir at r.t. for 72 h. The reaction mixture was concentrated and the residue purified by basic HPLC (ACN/0.005 mM H$_2$O—NH$_4$OH, 2.5:7.5 to 8:2) to give the title compound. 1H NMR (400 MHz, DMSO-d6) δ ppm 2.78 (t, J=7.45 Hz, 2H) 3.07 (t, J=7.33 Hz, 2H) 7.75 (s, 2H) 7.84-7.89 (m, 2H) 7.99 (d, J=7.45 Hz, 1H) 8.20 (dd, J=8.46, 1.39 Hz, 1H) 8.32-8.37 (m, 2H) 8.56 (br. s., 1H). MS (m/z) 515.0 M (+1), $t_R$=1.19, Meth 10

Example 1-68

3-{3,5-Dimethyl-4-[6-(5-o-tolyl-[1,3,4]oxadiazol-2-yl)-1H-benzoimidazol-2-yl]-phenyl}-2,2-dimethyl-propionic acid

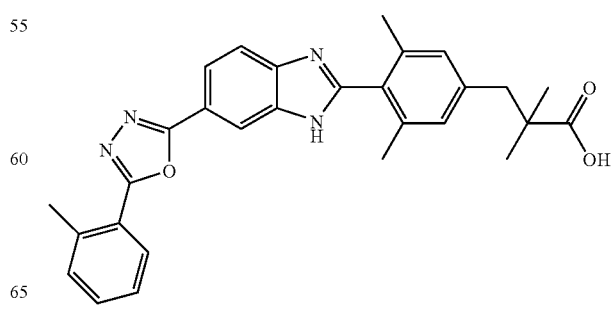

A. 2-[4-(2-Methoxycarbonyl-2-methyl-propyl)-2,6-dimethyl-phenyl]-3H-benzoimidazole-5-carboxylic acid 7.6 g of 3,4-diaminobenzenoic acid was stirred in 120 ml of DMF at room temperature. It was treated with 12.4 g of 3-(4-formyl-3,5-dimethyl-phenyl)-2,2-dimethyl-propionic acid methyl ester (the intermediate A in Example 1-62) followed by an addition of a slurry of 15 g of Oxone in 60 ml of DMF. The reaction was stirred at room temperature for 3 h and 60 mL of water was added and the pH was adjusted to 6. Additional 150 mL of water was added and the resulting precipitates were collected by filtration. The collected precipitates were washed with water and dried under vacuum to afford the title compound.

B. 3-{3,5-Dimethyl-4-[6-(5-o-tolyl-[1,3,4]oxadiazol-2-yl)-1H-benzoimidazol-2-yl]-phenyl}-2,2-dimethyl-propionic acid methyl ester Add EDC (380 mg, 1.98 mmol) and HOBt (268 mg, 1.98 mmol) to a stirring solution of 2-[4-(2-methoxycarbonyl-2-methyl-propyl)-2,6-dimethyl-phenyl]-3H-benzoimidazole-5-carboxylic acid (626 mg, 1.65 mmol) and 2-methyl-benzoic acid hydrazide (248 mg, 1.65 mmol) in DMF (6 mL) under N₂. Upon disappearance of the carboxylic acid by LC/MS, dilute the reaction with EtOAc (60 mL) and extract with water (20 mL) followed by brine (10 mL). Dry the organic phase over Na₂SO₄ and evaporate the solvent. Dissolve the residue in DMF (6 mL) and add Burgess reagent (1.18 g, 4.95 mmol). Heat the mixture my microwave irradiation to 150° C. for 15 min. Dilute the reaction with EtOAc (100 mL) and extract with water (25 mL). Extract the organic phase with saturated NaHCO₃ (2×25 mL) followed by brine (20 mL). Dry the organic phase over Na₂SO₄ and evaporate the solvent. Purify the residue by silica gel chromatography (10-45% ACN/DCM) to afford the title compound as a yellow oil: (M+H)+ 495.3.

C. 3-{3,5-Dimethyl-4-[6-(5-o-tolyl-[1,3,4]oxadiazol-2-yl)-1H-benzoimidazol-2-yl]-phenyl}-2,2-dimethyl-propionic acid Dissolve 3-{3,5-dimethyl-4-[6-(5-o-tolyl-[1,3,4]oxadiazol-2-yl)-1H-benzoimidazol-2-yl]-phenyl}-2,2-dimethyl-propionic acid methyl ester (286 mg, 0.578 mmol) in THF (2.9 mL)/MeOH (2.9 mL). Add 1 N NaOH (2.9 mL) and stir for 4 h. Add NaOH (102 mg, 2.55 mmol) in water (1 mL). Upon disappearance of the ester by LC/MS, concentrate the reaction. Acidify to pH 1.5 by addition of 1 N HCl (5.4 mL). Collect the solid by filtration and dry at 40° C. in a vacuum oven. Triturate the solid with DCM to afford the title compound as a white solid: (M+H)+ 481.0.

D. Sodium salt of 3-{3,5-Dimethyl-4-[6-(5-o-tolyl-[1,3,4]oxadiazol-2-yl)-1H-benzoimidazol-2-yl]-phenyl}-2,2-dimethyl-propionic acid Suspend 3-{3,5-dimethyl-4-[6-(5-o-tolyl-[1,3,4]oxadiazol-2-yl)-1H-benzoimidazol-2-yl]-phenyl}-2,2-dimethyl-propionic acid (162 mg, 0.337 mmol) in EtOH (2 mL) and add 1 N NaOH (337 uL). Add EtOH (2 mL) and heat to 50° C. for 1.5 h. Concentrate the suspension under reduced pressure. Re-suspend the residue in water and evaporate the solvent. Dry the solid at 40° C. in a vacuum oven to afford the title compound as a tan powder: 1H NMR (400 MHz, MeOD) δ ppm 1.12 (s, 6H) 2.15 (s, 6H) 2.77 (s, 3H) 2.86 (s, 2H) 7.08 (s, 2H) 7.40-7.55 (m, 3H) 7.82 (br. s., 1H) 8.07-8.15 (m, 2H) 8.41 (br. s., 1H); (M+H)+ 481.3.

Example 1-69

3-(4-{6-[5-(4-Chloro-phenyl)-[1,3,4]oxadiazol-2-yl]-1H-indol-2-yl}-3,5-dimethyl-phenyl)-2,2-dimethyl-propionic acid

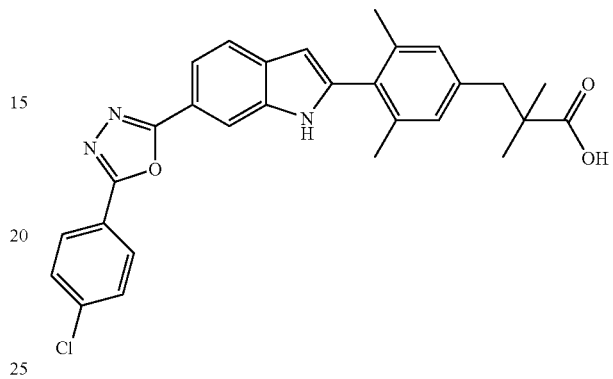

A. 2-(4-Bromomethyl-3-nitro-phenyl)-5-(4-chloro-phenyl)-[1,3,4]oxadiazole

To a 100 mL round-bottom flask was added 2.1 g (12.3 mmol) of 4-chlorobenzoic acid hydrazide, 3.20 g (12.3 mmol) of 4-bromomethyl-3-nitro benzoic acid, 3.54 g (18.5 mmol) of EDC, and 200 mL of DCM. Allowed to stir at room temperature for 18 h. Removed ⅔ of DCM, added water and filtered off white solid and washed with Et₂O to give 3-nitro-4-bromomethyl-benzoic acid N'-(4-chloro-benzoyl)-hydrazide as white solid. 1H NMR (400 MHz, DMSO-d6) δ ppm 4.99 (s, 1H) 5.12 (s, 1H) 7.59-7.64 (m, 2H) 7.91-7.95 (m, 2H) 7.96 (d, J=8.21 Hz, 1H) 8.22-8.29 (m, 1H) 8.57 (dd, J=6.57, 1.77 Hz, 1H) 10.76 (s, 1H) 10.94 (dd, J=5.18, 0.88 Hz, 1H). MS (m/z) 413.9 M (+1), $t_R$=1.28, Meth 10. To a 500 mL round-bottom flask was added 4.95 g (12.0 mmol) of 3-nitro-4-bromomethyl-benzoic acid N'-(4-chloro-benzoyl)-hydrazide, 6.09 g (36.0 mmol) DMC, and 100 mL of DCE. To this pale yellow solution was added 6.70 mL (48.0 mmol) of Et₃N, slowly over 5 min. The dark green solution was allowed to stir at 40° C. for 30 min. then cooled to room temperature stirred for 18 h. Removed solvent and purified over a silica plug 10-30% EtOAc/Hep to give the title compound as yellow solid. MS (m/z) 350.0 M (+1), retention time=1.51, Method 10.

B. 3-[4-((E)-2-{4-[5-(4-Chloro-phenyl)-[1,3,4]oxadiazol-2-yl]-2-nitro-phenyl}-vinyl)-3,5-dimethyl-phenyl]-2,2-dimethyl-propionic acid methyl ester Combine 2-(4-bromomethyl-3-nitro-phenyl)-5-(4-chloro-phenyl)-[1,3,4]oxadiazole (894 mg, 2.27 mmol) and PPh₃ (656 mg, 2.50 mmol) in DMF (13 mL) and heat to 95° C. under N₂ for 4.5 h. Add 3-(4-formyl-3,5-dimethyl-phenyl)-2,2-dimethyl-propionic acid methyl ester (intermediate A in Example 1-62, 675 mg, 2.72 mmol) and K₂CO₃ (627 mg, 4.54 mmol), continue heating at 95° C. for 6.5 h. Allow the reaction to cool to room temperature. Dilute the cooled reaction with EtOAc (150 mL) and extract with water (50 mL). Dry the organic layer over Na₂SO₄ and evaporate the solvent. Purify the resulting oil by silica gel chromatography (10-45% EtOAc/HEP) to afford a yellow solid: (M+H)+ 546.1.

C. 3-(4-{6-[5-(4-Chloro-phenyl)-[1,3,4]oxadiazol-2-yl]-1H-indol-2-yl}-3,5-dimethyl-phenyl)-2,2-dimethyl-propionic acid methyl ester Slurry 3-[4-((E)-2-{4-[5-(4-chloro-phenyl)-[1,3,4]oxadiazol-2-yl]-2-nitro-phenyl}-vinyl)-3,5-dimethyl-phenyl]-2,2-dimethyl-propionic acid methyl ester (245 mg, 0.449 mmol) in triethyl phosphite (6 mL) and heat to 160° C. for 2 h under $N_2$. Concentrate the reaction under reduced pressure. Purify the concentrate by silica gel chromatography (5-35% EtOAc/HEP) to afford 3-(4-{6-[5-(4-Chloro-phenyl)-[1,3,4]oxadiazol-2-yl]-1H-indol-2-yl}-3,5-dimethyl-phenyl)-2,2-dimethyl-propionic acid methyl ester as a yellow solid: (M+H)+ 514.3.

D. 3-(4-{6-[5-(4-Chloro-phenyl)-[1,3,4]oxadiazol-2-yl]-1H-indol-2-yl}-3,5-dimethyl-phenyl)-2,2-dimethyl-propionic acid Suspend 3-(4-{6-[5-(4-chloro-phenyl)-[1,3,4]oxadiazol-2-yl]-1H-indol-2-yl}-3,5-dimethyl-phenyl)-2,2-dimethyl-propionic acid methyl ester (262 mg, 0.510 mmol) in MeOH (2.6 mL)/1 N NaOH (2.6 mL) and heat to 50° C. for 3 h. Add THF (2.6 mL) and heat to 50° C. for 15 h. Add 1 N NaOH (2.6 mL), THF (2.6 mL), and NaOH (225 mg, 5.63 mmol) in water (1 mL). Heat the reaction at 50° C. until the ester is not observed by LC/MS. Concentrate the reaction under reduced pressure. Adjust the pH to 2 with 1 N HCl. Collect the resulting precipitate by filtration and rinse the solid with $Et_2O$ to afford a light yellow solid: (M+H)+ 500.2.

E. Sodium salt of 3-(4-{6-[5-(4-Chloro-phenyl)-[1,3,4]oxadiazol-2-yl]-1H-indol-2-yl}-3,5-dimethyl-phenyl)-2,2-dimethyl-propionic acid Suspend 3-(4-{6-[5-(4-chloro-phenyl)-[1,3,4]oxadiazol-2-yl]-1H-indol-2-yl}-3,5-dimethyl-phenyl)-2,2-dimethyl-propionic acid (183 mg, 366 umol) in EtOH (2 mL) and slowly add 1 N NaOH (336 uL). Stir for 2 h before evaporating the solvent under a stream of $N_2$. Re-suspend the residue in $Et_2O$/DCM and evaporate the solvent under a stream of $N_2$. Dry the resulting solid overnight in a vacuum oven at 40° C. to afford the sodium salt of 3-(4-{6-[5-(4-chloro-phenyl)-[1,3,4]oxadiazol-2-yl]-1H-indol-2-yl}-3,5-dimethyl-phenyl)-2,2-dimethyl-propionic acid as a tan solid: 1H NMR (400 MHz, DMSO-d6) δ ppm 0.93 (s, 6H) 2.08 (s, 6H) 2.67 (s, 2H) 6.45 (br. s., 1H) 6.98 (s, 2H) 7.64-7.87 (m, 4H) 8.08 (s, 1H) 8.13-8.24 (m, 2H) 11.69 (br. s., 1H); (M+H)+ 500.1.

Example 1-70

3-{4-[6-(5-Cyclohexyl-[1,3,4]oxadiazol-2-yl)-1H-benzoimidazol-2-yl]-3,5-dimethyl-phenyl}-2,2-dimethyl-propionic acid

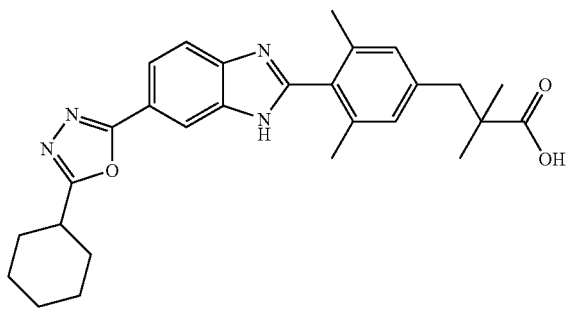

Preparation of the title compound is analogous to the preparation of Example 1-68. Cyclohexanecarboxylic acid hydrazide was used. Spectral data for sodium salt of 3-{4-[6-(5-cyclohexyl-[1,3,4]oxadiazol-2-yl)-1H-benzoimidazol-2-yl]-3,5-dimethyl-phenyl}-2,2-dimethyl-propionic acid; 1H NMR (400 MHz, MeOD) δ ppm 1.11 (s, 6H) 1.32-1.61 (m, 3H) 1.66-1.83 (m, 3H) 1.90 (dt, J=13.04, 3.33 Hz, 2H) 2.14 (s, 6H) 2.16-2.26 (m, 2H) 2.86 (s, 2H) 3.03-3.12 (m, 1H) 7.08 (s, 2H) 7.77 (d, J=8.46 Hz, 1H) 7.99 (dd, J=8.46, 1.52 Hz, 1H) 8.29 (s, 1H); (M+H)+ 473.3.

Example 1-71

3-(4-{6-[5-(2-Methoxy-phenyl)-[1,3,4]oxadiazol-2-yl]-1H-benzoimidazol-2-yl}-3,5-dimethyl-phenyl)-2,2-dimethyl-propionic acid

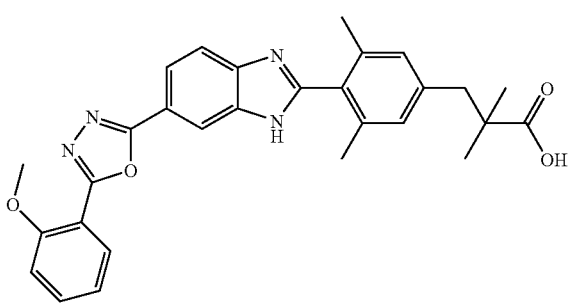

Preparation of the title compound is analogous to the preparation of Example 1-68. 2-Methoxybenzoic acid hydrazide was used. Spectral data for sodium salt of 3-(4-{6-[5-(2-methoxy-phenyl)-[1,3,4]oxadiazol-2-yl]-1H-benzoimidazol-2-yl}-3,5-dimethyl-phenyl)-2,2-dimethyl-propionic acid; 1H NMR (400 MHz, DMSO-d6) δ ppm 0.96 (s, 6H) 2.07 (s, 6H) 2.72 (s, 2H) 3.97 (s, 3H) 6.99 (s, 2H) 7.17 (td, J=7.55, 0.95 Hz, 1H) 7.31 (d, J=8.08 Hz, 1H) 7.63 (ddd, J=8.65, 7.26, 1.77 Hz, 1H) 7.74 (br. s., 1H) 7.89 (d, J=8.34 Hz, 1H) 7.99 (dd, J=7.70, 1.77 Hz, 1H) 8.23 (br. s., 1H) 13.20 (br. s., 1H); (M+H)+ 497.0.

Example 1-72

3-(4-{6-[5-(4-Methoxy-2-methyl-phenyl)-[1,3,4] oxadiazol-2-yl]-1H-benzoimidazol-2-yl}-3,5-dimethyl-phenyl)-2,2-dimethyl-propionic acid

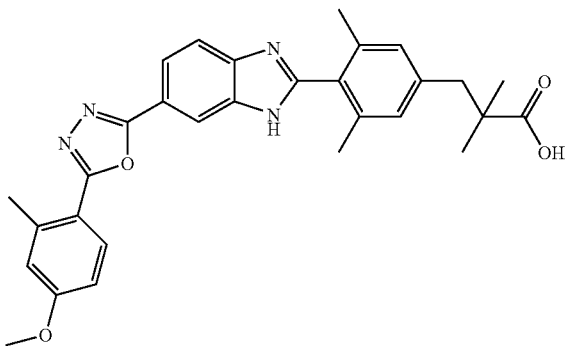

Preparation of the title compound is analogous to the preparation of Example 1-68. 4-Methoxy-2-methyl-benzoic acid hydrazide was used. Spectral data for sodium salt of 3-(4-{6-[5-(4-methoxy-2-methyl-phenyl)-[1,3,4]oxadiazol-2-yl]-1H-benzoimidazol-2-yl}-3,5-dimethyl-phenyl)-2,2-dimethyl-propionic acid; 1H NMR (400 MHz, DMSO-d6) δ ppm 0.96 (s, 6H) 2.07 (s, 6H) 2.71 (s, 5H) 3.86 (s, 3H) 6.95-7.08 (m, 4H) 7.74 (br.s., 1H) 7.93 (d, J=8.84 Hz, 1H) 8.07 (d, J=8.72 Hz, 1H) 8.28 (br. s., 1H) 13.13 (br. s., 1H); (M+H)+ 511.2.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:
1. A compound having the following structure

A-Q-B-C-D wherein

A is an aryl, or a monocyclic or bicyclic heterocyclyl, wherein the aryl or heterocyclyl may be optionally substituted with one or more substituents independently selected from the group consisting of halogen, alkyl, phenyl, cycloalkyl, cyano, trifluoromethyl, alkoxy, hydroxyl, optionally substituted amino, acyl, alkanoyloxy, aryloxy, alkylthio, arylthio, oxo, nitro, carboxy, alkoxycarbonyl, carbamoyl, alkylthiono, sulfonyl, sulfonamido, and heterocyclyl;

Q is a divalent or trivalent five membered heterocycle or heteroaryl selected from the group consisting of:

B is a divalent heteroaryl group selected from the group consisting of:

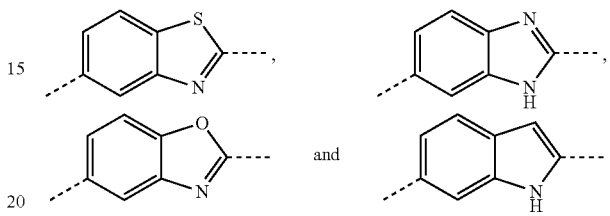

C is

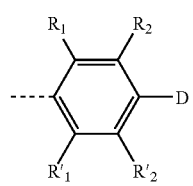

wherein $R_1$ is selected from hydrogen, cyano, lower alkylsulfonylamino, alkanoylamino, halogen, lower alkyl, trifluoromethyl, lower alkoxy, lower alkylamino, lower dialkylamino, and $NO_2$, $R'_1$, $R_2$ and $R'_2$ are independently selected from hydrogen, halogen, trifluoromethyl, aryloxy, lower alkyl, lower alkoxy, lower alkylamino, lower dialkylamino, and $NO_2$, or D is selected from hydrogen, halogen, hydroxyl, cyano, alkanoylamino, carboxy, carbamoyl, —O-$L_2$-E, —S-$L_2$-E', —C(O)—O-$L_2$-E, -$L_2$-E'', and —N$R_6$-$L_2$-E', $L_2$ is —$(CH_2)_{n'}$—$(CR_5R_{5'})_{p'}$—$(CH_2)_{m'}$—

E is alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —$SO_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido, E' is alkyl, acyl, alkoxycarbonyl, cycloalkoxycarbonyl, aryloxycarbonyl, heterocyclyloxycarbony, carboxy, carbamoyl, sulfonylcarbamoyl, sulfonyl, —$SO_2$—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E″ is alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, —SO$_2$—OH, sulfonylcarbamoyl, —C(O)—O—R—PRO, substituted or unsubstituted aryl, substituted or unsubstituted heterocyclyl, or substituted or unsubstituted heteroaryl, m′, n′ and p′ are, independently from each other, an integer from 0 to 4, m′+n′+p′ is between 0 and 12, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

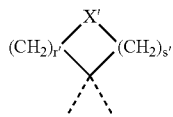

wherein

X′ is $NR_x$, O, S or $CR_{x'}R_{x''}$ r′ and s′ are, independently from each other, zero or an integer from 1 to 3, $R_x$ is hydrogen or lower alkyl, $R_{x'}$ is hydrogen, halogen, hydroxyl, alkoxy, or lower alkyl, $R_{x''}$ is hydrogen or lower alkyl; or a stereoisomer, enantiomer or tautomer thereof, a pharmaceutically acceptable salt thereof, or a prodrug thereof.

2. The compound according to claim 1, or a stereoisomer, enantiomer or tautomer thereof, a pharmaceutically acceptable salt thereof, or a prodrug thereof, wherein A is selected from the group consisting of:

$C_{1-4}$alkyl, a substituted or unsubstituted $C_6$ monocyclic aryl group, a substituted or unsubstituted 6-membered monocyclic heteroaryl group, a substituted or unsubstituted 9 or 10-membered bicyclic aryl group, a substituted or unsubstituted biphenyl, a substituted or unsubstituted 5 or 6-membered monocyclic heterocyclyl, and a 9 or 10-membered bicyclic heterocyclyl group.

3. The compound according to claim 1, or a stereoisomer, enantiomer or tautomer thereof, a pharmaceutically acceptable salt thereof, or a prodrug thereof, wherein A is selected from the group consisting of a substituted or unsubstituted phenyl, a substituted or unsubstituted naphthyl, and a substituted or unsubstituted biphenyl.

4. The compound according to claim 1, or a stereoisomer, enantiomer or tautomer thereof, a pharmaceutically acceptable salt thereof, or a prodrug thereof, wherein A is a substituted or unsubstituted monocyclic heteroaryl selected from the group consisting of a substituted or unsubstituted imidazole, substituted or unsubstituted pyrazole, substituted or unsubstituted triazole substituted or unsubstituted thiazole, substituted or unsubstituted pyridine, substituted or unsubstituted pyridine N-oxide substituted or unsubstituted pyridazine, substituted or unsubstituted pyrimidine, substituted or unsubstituted triazine and substituted or unsubstituted pyrazine residue.

5. The compound according to claim 1, or a stereoisomer, enantiomer or tautomer thereof, a pharmaceutically acceptable salt thereof, or a prodrug thereof, wherein A is a substituted or unsubstituted phenyl.

6. The compound according to claim 1, or a stereoisomer, enantiomer or tautomer thereof, a pharmaceutically acceptable salt thereof, or a prodrug thereof, wherein A is selected from the group consisting of:

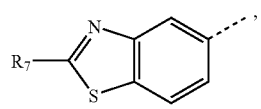

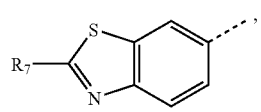 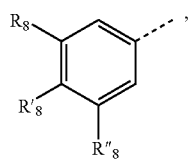

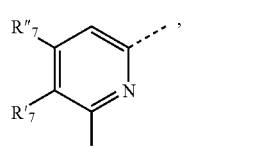 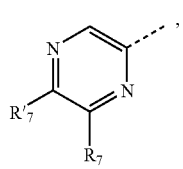

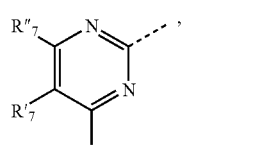 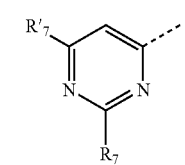

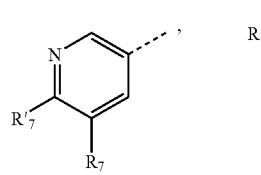 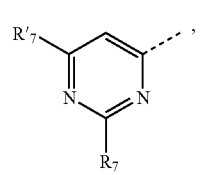

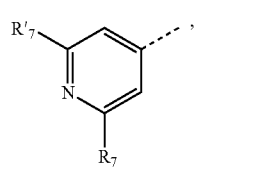 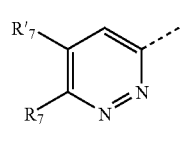

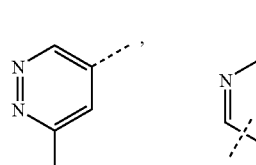 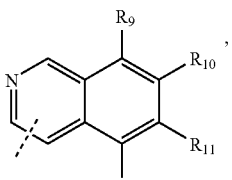

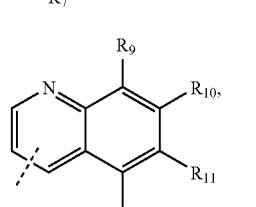 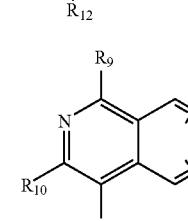

-continued

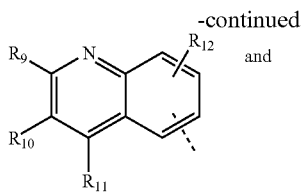

and

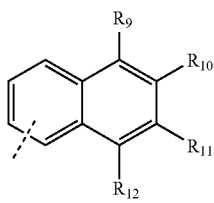

wherein,
R₇, R'₇ and R"₇ are independently selected from the group consisting of hydrogen, optionally substituted alkyl; hydroxyl, protected hydroxyl; halo; oxo; optionally substituted amino; optionally substituted alkoxy; cycloalkyl; carboxy; heterocyclooxy; alkoxycarbonyl; mercapto; nitro; cyano; sulfamoyl; alkanoyloxy; aroyloxy; arylthio; optionally substituted aryloxy; alkylthio; formyl; carbamoyl; optionally substituted aralkyl; optionally substituted aryl, and optionally substituted phenyl, R₈, R'₈ and R"₈ are independently selected from the group consisting of hydrogen, optionally substituted alkyl, trifluoromethyl, trifluoromethoxy, cycloalkyl, halo, hydroxy, optionally substituted alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, and optionally substituted heterocyclyl, and R₉, R₁₀, R₁₁ and R₁₂ are independently selected from the group consisting of hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, and optionally substituted heterocyclyl.

7. The compound according to claim 6, or a stereoisomer, enantiomer or tautomer thereof, a pharmaceutically acceptable salt thereof, or a prodrug thereof, wherein one or two of the substituents R₇, R'₇ and R"₇ is not hydrogen, and one or two of the substituents R₈, R'₈ and R"₈ is not hydrogen.

8. The compound according to claim 1, or a stereoisomer, enantiomer or tautomer thereof, a pharmaceutically acceptable salt thereof, or a prodrug thereof, wherein the moiety C is

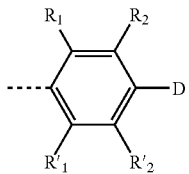

wherein
R₁ is selected from halogen, cyano, lower alkylsulfonylamino, alkanoylamino, lower alkyl, trifluoromethyl, lower alkoxy, lower alkylamino, lower dialkylamino, and NO₂,
R'₁ is selected from hydrogen, halogen, lower alkyl, trifluoromethyl, lower alkoxy, lower alkylamino, lower dialkylamino, and NO₂, and
R₂ and R'₂ are hydrogen.

9. The compound according to claim 1, or a stereoisomer, enantiomer or tautomer thereof, a pharmaceutically acceptable salt thereof, or a prodrug thereof, wherein the moiety C is

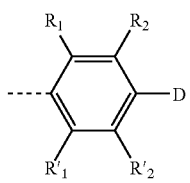

wherein
R₁ is selected from halogen, and lower alkyl,
R'₁ is selected from hydrogen, nitro, halogen, and lower alkyl, and
R₂ and R'₂ are hydrogen.

10. The compound according to claim 1, or a stereoisomer, enantiomer or tautomer thereof, a pharmaceutically acceptable salt thereof, or a prodrug thereof, wherein the moiety D is selected from the group consisting of hydrogen, halogen, hydroxyl, cyano, alkanoylamino, carboxy, —O-L₂-E, -L₂-E", —C(O)—O-L₂-E and —NR₆-L₂-E',
wherein,
L₂ is —(CH₂)ₙ'—(CR₅R₅')ₚ'—(CH₂)ₘ'—
E is; alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —SO₂—OH, —C(O)—O—R—PRO, substituted or unsubstituted aryl, substituted or unsubstituted heterocyclyl, or substituted or unsubstituted heteroaryl,
E' is; alkyl, acyl, alkoxycarbonyl, cycloalkoxycarbonyl, aryloxycarbonyl, heterocyclyloxycarbony, carboxy, carbamoyl, sulfonyl, —SO₂—OH, —C(O)—O—R—PRO, substituted or unsubstituted aryl, substituted or unsubstituted heterocyclyl, or substituted or unsubstituted heteroaryl,
E" is alkyl, acyl, alkoxycarbonyl, phosphonic acid, phosphonate, cycloalkoxycarbonyl, aryloxycarbonyl, heterocyclyloxycarbony, carboxy, sulfonyloxy, substituted or unsubstituted aryl, substituted or unsubstituted heterocyclyl, or substituted or unsubstituted heteroaryl,
m', n' and p' are, independently from each other, an integer from 0 to 4,
m'+n'+p' is between 0 and 12,
R₅ and R₅' are, independently from each other, hydrogen, halogen, hydroxyl, lower alkoxy, or lower alkyl, and
R₆ is hydrogen or lower alkyl.

11. The compound according to claim 1, or a stereoisomer, enantiomer or tautomer thereof, a pharmaceutically acceptable salt thereof, or a prodrug thereof, wherein the moiety D is selected from the group consisting of hydrogen, halogen, hydroxyl, cyano, alkanoylamino, carboxy, carbamoyl, -L₂-

(substituted or unsubstituted lower alkyl), -L₂-alkoxycarbonyl, -L₂-acyl, -L₂-(substituted or unsubstituted heteroaryl) and —O-L₂-E, wherein;

L₂ is —(CH₂)ₙ'—(CR₅R₅')ₚ'—(CH₂)ₘ'—

E is a substituted or unsubstituted lower alkyl, acyl, a substituted or unsubstituted lower alkoxycarbonyl, phosphonic acid, phosphonate, cycloalkoxycarbonyl, aryloxycarbonyl, heterocyclyloxycarbony, carboxy, carbamoyl, sulfonyl, substituted or unsubstituted heterocyclyl, or substituted or unsubstituted heteroaryl, m', n' and p' are, independently from each other, an integer from 0 to 4, m'+n'+p' is between 0 and 12, and R₅ and R₅' are, independently from each other, hydrogen.

12. The compound according to claim 1, or a stereoisomer, enantiomer or tautomer thereof, a pharmaceutically acceptable salt thereof, or a prodrug thereof, wherein the divalent residue -L₂- has the following orientation:

—O—(CH₂)ₙ'—(CR₅R₅')ₚ'—(CH₂)ₘ'→E, —S—(CH₂)ₙ'—(CR₅R₅')ₚ'—(CH₂)ₘ'→E', —C(O)—O—(CH₂)ₙ'—(CR₅R₅')ₚ'—(CH₂)ₘ'→E', —(CH₂)ₙ'—(CR₅R₅')ₚ'—(CH₂)ₘ'→E'', or —NR₆—(CH₂)ₙ'—(CR₅R₅')ₚ'—(CH₂)ₘ'→E''.

13. The compound according to claim 1, or a stereoisomer, enantiomer or tautomer thereof, a pharmaceutically acceptable salt thereof, or a prodrug thereof, wherein the moiety D is -L₂-E'', wherein;

L₂ is —(CH₂)ₙ'—(CR₅R₅')ₚ'—(CH₂)ₘ'— m', n' and p' are, independently from each other, an integer from 0 to 4, m'+n'+p' is between 0 and 12, and R₅ and R₅' are, independently from each other, hydrogen or $C_{1-4}$alkyl.

14. The compound according to claim 1, or a stereoisomer, enantiomer or tautomer thereof, a pharmaceutically acceptable salt thereof, or a prodrug thereof, wherein the moiety E is phosphonic acid, —P(O₂)-(substituted or unsubstituted lower alkyl), —P(O₂)-(substituted or unsubstituted phenyl), carboxy, —S(O)₂—OH, —S(O)₂-(substituted or unsubstituted lower alkyl), —S(O)₂-(substituted or unsubstituted phenyl), —S(O)₂-trifluoromethyl, a substituted or unsubstituted lower alkyl, a substituted or unsubstituted heterocyclolyl, a substituted or unsubstituted alkanoyl, a substituted or unsubstituted alkoxycarbonyl, a substituted or unsubstituted phenyloxycarbonyl, —C(O)—NH-(substituted or unsubstituted lower alkyl), —C(O)—N(substituted or unsubstituted lower alkyl)₂, —C(O)—NH₂, a substituted or unsubstituted 5-membered monocyclic heterocyclyl.

15. The compound according to claim 1, or a stereoisomer, enantiomer or tautomer thereof, a pharmaceutically acceptable salt thereof, or a prodrug thereof, wherein the moiety D is hydrogen, lower alkanoylamino, or carboxy.

16. The compound according to claim 1 selected from
6-[5-(4-Chloro-phenyl)-[1,3,4]oxadiazol-2-yl]-2-(2,6-dichloro-phenyl)-1H-benzoimidazole;
2-(2,6-Dichloro-phenyl)-6-(5-m-tolyl-[1,3,4]oxadiazol-2-yl)-1H-benzoimidazole;
2-(2,6-Dichloro-phenyl)-6-[5-(3-fluoro-phenyl)-[1,3,4]oxadiazol-2-yl]-1H-benzoimidazole;
2-(2,6-Dichloro-phenyl)-6-[5-(4-methoxy-phenyl)-[1,3,4]oxadiazol-2-yl]-1H-benzoimidazole;
6-[5-(4-Bromo-phenyl)-[1,3,4]oxadiazol-2-yl]-2-(2,6-dichloro-phenyl)-1H-benzoimidazole;
2-(2,6-Dichloro-phenyl)-6-(5-p-tolyl-[1,3,4]oxadiazol-2-yl)-1H-benzoimidazole;
2-(2,6-Dichloro-phenyl)-6-[5-(4-fluoro-phenyl)-[1,3,4]oxadiazol-2-yl]-1H-benzoimidazole;
2-(2,6-Dichloro-phenyl)-6-[5-(5-methyl-pyridin-3-yl)-[1,3,4]oxadiazol-2-yl]-1H-benzoimidazole;
2-(2,6-Dimethyl-phenyl)-6-[5-(4-methoxy-phenyl)-[1,3,4]oxadiazol-2-yl]-1H-benzoimidazole;
2-(2,6-Dichloro-phenyl)-6-[5-(2-methoxy-pyridin-3-yl)-[1,3,4]oxadiazol-2-yl]-1H-benzoimidazole;
2-(2,6-Dichloro-phenyl)-6-[5-(2-methoxy-pyridin-3-yl)-[1,3,4]oxadiazol-2-yl]-1H-benzoimidazole;
2-(2,6-Dichloro-phenyl)-6-[5-(6-trifluoromethyl-pyridin-3-yl)-[1,3,4]oxadiazol-2-yl]-1H-benzoimidazole;
4-{(5-[2-(2,6-Dichloro-phenyl)-3H-benzoimidazol-5-yl]-[1,3,4]oxadiazol-2-yl}-benzonitrile;
6-[5-(4-Chloro-phenyl)-[1,3,4]oxadiazol-2-yl]-2-(2,6-dimethyl-4-morpholin-4-yl-phenyl)-1H-benzoimidazole;
6-[5-(4-Chloro-phenyl)-[1,3,4]oxadiazol-2-yl]-2-(3,5-dichloro-pyridin-4-yl)-1H-benzoimidazole;
6-[5-(4-Chloro-phenyl)-[1,3,4]oxadiazol-2-yl]-2-(2,6-dimethyl-phenyl)-1H-benzoimidazole;
2-(2,6-Dichloro-phenyl)-6-(4,5-diphenyl-oxazol-2-yl)-1H-benzoimidazole;
6-[5-(4-chlorophenyl)-4-methyloxazol-2-yl]-2-(2,6-dichlorophenyl)-1H-benzimidazole;
6-[5-(4-chlorophenyl)-oxazol-2-yl]-2-(2,6-dichlorophenyl)-1H-benzoimidazole;
6-[5-(4-Chloro-phenyl)-[1,3,4]oxadiazol-2-yl]-2-(2,6-dichloro-4-morpholin-4-yl-phenyl)-1H-benzoimidazole;
2-(2,6-Dichloro-phenyl)-6-(5-morpholin-4-yl-[1,3,4]oxadiazol-2-yl)-1H-benzoimidazole;
2-(2,6-Dichloro-phenyl)-6-(5-piperidin-1-yl-[1,3,4]oxadiazol-2-yl)-1H-benzoimidazole;
2-(2,6-Dichloro-phenyl)-6-(5-pyrrolidin-1-yl-[1,3,4]oxadiazol-2-yl)-1H-benzoimidazole;
(4-{6-[5-(4-Chloro-phenyl)-[1,3,4]oxadiazol-2-yl]-1H-benzoimidazol-2-yl}-3,5-dimethyl-phenoxy)-acetic acid;
(3,5-Dichloro-4-{6-[5-(4-chloro-phenyl)-[1,3,4]oxadiazol-2-yl]-1H-benzoimidazol-2-yl}-phenoxy)-acetic acid;
3-(4-{6-[5-(4-Methoxy-phenyl)-[1,3,4]oxadiazol-2-yl]-1H-benzoimidazol-2-yl}-3,5-dimethyl-phenyl)-propionic acid;
3-(4-{6-[5-(4-Chloro-phenyl)-[1,3,4]oxadiazol-2-yl]-1H-benzoimidazol-2-yl}-3,5-dimethyl-phenyl)-propionic acid;
3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid;
[3-(4-{6-[5-(4-Chloro-phenyl)-[1,3,4]oxadiazol-2-yl]-1H-benzoimidazol-2-yl}-3,5-dimethyl-phenyl)-propyl]-phosphonic acid;
(3-{3,5-Dimethyl-4-[6-(5-phenyl-[1,3,4]oxadiazol-2-yl)-1H-benzoimidazol-2-yl]-phenyl}-propyl)-phosphonic acid;
[3-(4-{6-[5-(4-Methoxy-phenyl)-[1,3,4]oxadiazol-2-yl]-1H-benzoimidazol-2-yl}-3,5-dimethyl-phenyl)-propyl]-phosphonic acid;
3-{4-[6-(5-methoxy-[1,3,4]oxadiazol-2-yl)-1H-indol-2-yl]-3,5-dimethylphenyl}-propionic acid;
3-(3,5-Dichloro-4-{6-[5-(4-chloro-phenyl)-[1,3,4]oxadiazol-2-yl]-1H-benzoimidazol-2-yl}-phenyl)-propionic acid;

3-{3,5-Dimethyl-4-[6-(5-o-tolyl-[1,3,4]oxadiazol-2-yl)-1H-benzoimidazol-2-yl]-phenyl}-2,2-dimethyl-propionic acid;

3-(4-{6-[5-(4-Chloro-phenyl)-[1,3,4]oxadiazol-2-yl]-1H-indol-2-yl}-3,5-dimethyl-phenyl)-2,2-dimethyl-propionic acid;

3-(4-{6-[5-(2-Methoxy-phenyl)-[1,3,4]oxadiazol-2-yl]-1H-benzoimidazol-2-yl}-3,5-dimethyl-phenyl)-2,2-dimethyl-propionic acid;

3-(4-{6-[5-(4-Methoxy-2-methyl-phenyl)-[1,3,4]oxadiazol-2-yl]-1H-benzoimidazol-2-yl}-3,5-dimethyl-phenyl)-2,2-dimethyl-propionic acid;

or any pharmaceutically acceptable salt or prodrug thereof.

17. A pharmaceutical composition, comprising:
the compound according to claim 1, or a stereoisomer, enantiomer or tautomer thereof, a pharmaceutically acceptable salt thereof, or a prodrug thereof, and
a pharmaceutical acceptable carrier or excipient.

18. A method of treating a DGAT1 mediated disorder, wherein the DGAT mediated disorder is impaired glucose tolerance, Type 2 diabetes or obesity, comprising:
administering to a subject in need thereof a therapeutic amount of the compound according to claim 1, or a stereoisomer, enantiomer or tautomer thereof, a pharmaceutically acceptable salt thereof, or a prodrug thereof.

* * * * *